(12) United States Patent
Brownstein et al.

(10) Patent No.: US 11,590,223 B2
(45) Date of Patent: Feb. 28, 2023

(54) DOSING STRATEGY THAT MITIGATES CYTOKINE RELEASE SYNDROME FOR THERAPEUTIC ANTIBODIES

(71) Applicant: Regeneron Pharmaceuticals, Inc., Tarrytown, NY (US)

(72) Inventors: Carrie Brownstein, New York, NY (US); Israel Lowy, Dobbs Ferry, NY (US); Lieve Lucille Adriaens, Westfield, NJ (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 557 days.

(21) Appl. No.: 16/556,885

(22) Filed: Aug. 30, 2019

(65) Prior Publication Data

US 2020/0129617 A1    Apr. 30, 2020

Related U.S. Application Data

(60) Provisional application No. 62/726,137, filed on Aug. 31, 2018, provisional application No. 62/774,019, filed on Nov. 30, 2018, provisional application No. 62/861,100, filed on Jun. 13, 2019.

(51) Int. Cl.
| | | |
|---|---|---|
| *A61K 39/395* | (2006.01) | |
| *C07K 16/28* | (2006.01) | |
| *A61P 35/00* | (2006.01) | |
| *A61K 31/405* | (2006.01) | |
| *A61K 31/573* | (2006.01) | |
| *A61K 45/06* | (2006.01) | |
| *C07K 16/24* | (2006.01) | |
| *A61K 39/00* | (2006.01) | |

(52) U.S. Cl.
CPC ........ *A61K 39/3955* (2013.01); *A61K 31/405* (2013.01); *A61K 31/573* (2013.01); *A61K 45/06* (2013.01); *A61P 35/00* (2018.01); *C07K 16/248* (2013.01); *C07K 16/2809* (2013.01); *C07K 16/2818* (2013.01); *C07K 16/2866* (2013.01); *C07K 16/2887* (2013.01); *A61K 2039/507* (2013.01); *A61K 2039/545* (2013.01); *C07K 2317/31* (2013.01)

(58) Field of Classification Search
None
See application file for complete search history.

(56) References Cited

U.S. PATENT DOCUMENTS

| | | | |
|---|---|---|---|
| 5,500,362 A | 3/1996 | Robinson et al. | |
| 5,624,821 A | 4/1997 | Winter et al. | |
| 5,648,260 A | 7/1997 | Winter et al. | |
| 5,658,570 A | 8/1997 | Newman et al. | |
| 5,677,180 A | 10/1997 | Robinson et al. | |
| 5,721,108 A | 2/1998 | Robinson et al. | |
| 5,736,137 A | 4/1998 | Anderson et al. | |
| 5,776,456 A | 7/1998 | Anderson et al. | |
| 5,843,439 A | 12/1998 | Anderson et al. | |
| 6,120,767 A | 9/2000 | Robinson et al. | |
| 6,180,377 B1 | 1/2001 | Morgan et al. | |
| 6,224,866 B1 | 5/2001 | Barbera-Guillem | |
| 6,399,061 B1 | 6/2002 | Anderson et al. | |
| 6,455,043 B1 | 9/2002 | Grillo-Lopez | |
| 6,528,624 B1 | 3/2003 | Idusogie et al. | |
| 6,551,592 B2 | 4/2003 | Lindhofer et al. | |
| 6,652,852 B1 | 11/2003 | Robinson et al. | |
| 6,682,734 B1 | 1/2004 | Anderson et al. | |
| 6,893,625 B1 | 5/2005 | Robinson et al. | |
| 7,151,164 B2 | 12/2006 | Hansen et al. | |
| 7,214,775 B2 | 5/2007 | Hanai et al. | |
| 7,396,917 B2 | 7/2008 | Bowdish et al. | |
| 7,563,441 B2 | 7/2009 | Graus et al. | |
| 7,597,889 B1 | 10/2009 | Armour et al. | |
| 7,608,260 B2 | 10/2009 | Schenerman et al. | |
| 7,700,097 B2 | 4/2010 | Braslawsky et al. | |
| 7,700,099 B2 | 4/2010 | Strohl | |
| 7,728,114 B2 | 6/2010 | Mach et al. | |
| 7,820,166 B2 | 10/2010 | Lanzavecchia et al. | |
| 7,824,684 B2 | 11/2010 | Graus | |
| 7,867,491 B2 | 1/2011 | Yang et al. | |
| 7,879,984 B2 | 2/2011 | Martin et al. | |
| 7,960,512 B2 | 6/2011 | Stavenhagen et al. | |
| 8,075,884 B2 | 12/2011 | Bowdish et al. | |
| 8,076,459 B2 | 12/2011 | Hofmeister et al. | |

(Continued)

FOREIGN PATENT DOCUMENTS

| | | |
|---|---|---|
| EP | 0327378 B1 | 12/1996 |
| EP | 1400534 A1 | 3/2004 |

(Continued)

OTHER PUBLICATIONS

Bannerji et al, Blood, 2016, vol. 128, No. 22, pp. 621.*
Varghese et al, Blood, 2014 vol. 124, No. 21.*
"IgG-Fc Engineering for Therapeutic Use," InvivoGen Insight, 1 page, (2006). [Author Unknown] [Retrieved from the Internet Apr. 4, 2014: <URL: http://www.invivogen.comiclocs/Insight200605-pdf >].
"IgG-Fe engineering for therapeutic use," Invivogen, 2 pages, (2007). [Author Unknown] [Retrieved from the Internet Jan. 12, 2011: <URL: http://www.invivogen.com/ressource.php?ID=22>].
Aalberse et al., "IgG4 breaking the rules," Immunology, 105(1):9-19, (2002).

(Continued)

*Primary Examiner* — Bridget E Bunner
*Assistant Examiner* — Fozia M Hamud
(74) *Attorney, Agent, or Firm* — Schwabe, Williamson & Wyatt PC; Aparna Patankar

(57) ABSTRACT

Administration regimens for therapeutic proteins (e.g., T cell-activating bispecific antibodies) that mitigate cytokine release syndrome and infusion-related reaction are disclosed. The methods employ initial fractional dosing with optional administration of additional agents such as steroids or cytokine antagonists that are discontinued with maximal weekly dosing over the course of the dosing regimen.

53 Claims, 1 Drawing Sheet
Specification includes a Sequence Listing.

(56) References Cited

U.S. PATENT DOCUMENTS

| | | |
|---|---|---|
| 8,084,026 B2 | 12/2011 | Glaser et al. |
| 8,097,713 B2 | 1/2012 | Martin et al. |
| 8,153,583 B2 | 4/2012 | Carton et al. |
| 8,236,314 B2 | 8/2012 | Kai et al. |
| 8,268,972 B2 | 9/2012 | Whitfield et al. |
| 8,329,181 B2 | 12/2012 | Martin et al. |
| 8,383,109 B2 | 2/2013 | Lazar et al. |
| 8,409,568 B2 | 4/2013 | Gao et al. |
| 8,961,967 B2 | 2/2015 | Strohl et al. |
| 9,359,437 B2 | 6/2016 | Davis et al. |
| 9,657,102 B2 | 5/2017 | Smith et al. |
| 10,106,610 B2 | 10/2018 | Davis et al. |
| 10,179,819 B2 | 1/2019 | Kirshner et al. |
| 10,421,804 B2 | 9/2019 | Kyratsous et al. |
| 10,550,193 B2 | 2/2020 | Smith et al. |
| 10,556,952 B2 | 2/2020 | Davis et al. |
| 10,662,244 B2 | 5/2020 | Smith et al. |
| 10,738,130 B2 | 8/2020 | Haber et al. |
| 10,772,972 B2 | 9/2020 | Rudge et al. |
| 10,988,537 B2 | 4/2021 | Davis et al. |
| 11,072,656 B2 | 7/2021 | Smith et al. |
| 11,117,955 B2 | 9/2021 | Kyratsous et al. |
| 11,155,621 B2 | 10/2021 | Smith et al. |
| 2003/0026804 A1 | 2/2003 | Grillo-Lopez |
| 2004/0093621 A1 | 5/2004 | Shitara |
| 2004/0167319 A1 | 8/2004 | Teeling et al. |
| 2004/0171123 A1 | 9/2004 | Rosen et al. |
| 2005/0025764 A1 | 2/2005 | Watkins |
| 2005/0037000 A1 | 2/2005 | Stavenhagen et al. |
| 2005/0053602 A1 | 3/2005 | Brunetta |
| 2005/0191297 A1 | 9/2005 | Brunetta |
| 2005/0226876 A1 | 10/2005 | Graus et al. |
| 2005/0244403 A1 | 11/2005 | Lazar et al. |
| 2005/0271658 A1 | 12/2005 | Brunetta |
| 2006/0024295 A1 | 2/2006 | Brunetta |
| 2006/0110387 A1 | 6/2006 | Dahiyat et al. |
| 2006/0121032 A1 | 6/2006 | Dahiyat et al. |
| 2006/0134709 A1 | 6/2006 | Stavenhagen et al. |
| 2006/0193852 A1 | 8/2006 | Dorken et al. |
| 2006/0233797 A1 | 10/2006 | Gujrathi |
| 2006/0240007 A1 | 10/2006 | Sanders |
| 2006/0263355 A1 | 11/2006 | Quan et al. |
| 2007/0009523 A1 | 1/2007 | Presta |
| 2007/0014720 A1 | 1/2007 | Gazit-Bornstein et al. |
| 2007/0020259 A1 | 1/2007 | Hansen et al. |
| 2007/0041972 A1 | 2/2007 | Rother et al. |
| 2007/0081993 A1 | 4/2007 | Kufer et al. |
| 2009/0022738 A1 | 1/2009 | Hofmeister et al. |
| 2009/0035322 A1 | 2/2009 | Martin et al. |
| 2009/0117133 A1 | 5/2009 | Arnason et al. |
| 2009/0162901 A1 | 6/2009 | Chen et al. |
| 2009/0252729 A1 | 10/2009 | Farrington et al. |
| 2010/0105874 A1 | 4/2010 | Schuurman et al. |
| 2010/0166749 A1 | 7/2010 | Presta |
| 2010/0178298 A1 | 7/2010 | Lindhofer |
| 2010/0183554 A1 | 7/2010 | Mach et al. |
| 2010/0183615 A1 | 7/2010 | Kufer et al. |
| 2010/0267934 A1 | 10/2010 | Winkel et al. |
| 2010/0298542 A1 | 11/2010 | Igawa et al. |
| 2010/0325744 A1 | 12/2010 | Schuurman et al. |
| 2010/0331527 A1 | 12/2010 | Davis et al. |
| 2011/0077383 A1 | 3/2011 | Dall'Acqua et al. |
| 2011/0212087 A1 | 9/2011 | Strohl et al. |
| 2011/0245473 A1 | 10/2011 | Igawa et al. |
| 2011/0263830 A1 | 10/2011 | Goetsch et al. |
| 2011/0293607 A1 | 12/2011 | Labrijn et al. |
| 2012/0065379 A1 | 3/2012 | Igawa et al. |
| 2012/0071634 A1 | 3/2012 | Igawa et al. |
| 2012/0100140 A1 | 4/2012 | Reyes et al. |
| 2012/0189643 A1 | 7/2012 | Carton et al. |
| 2012/0225058 A1 | 9/2012 | Lazar et al. |
| 2012/0237515 A1 | 9/2012 | Bell et al. |
| 2012/0238729 A1 | 9/2012 | Kuramochi et al. |
| 2012/0251531 A1 | 10/2012 | Baehner et al. |
| 2012/0276096 A1 | 11/2012 | Yang et al. |
| 2012/0276097 A1 | 11/2012 | Yang et al. |
| 2013/0011386 A1 | 1/2013 | Brerski et al. |
| 2013/0101581 A1 | 4/2013 | Kuramochi et al. |
| 2013/0108623 A1 | 5/2013 | D'Angelo et al. |
| 2013/0129723 A1 | 5/2013 | Blankenship et al. |
| 2013/0251707 A1 | 9/2013 | Kontermann et al. |
| 2014/0088295 A1 | 3/2014 | Smith et al. |
| 2014/0112914 A1 | 4/2014 | Nezu et al. |
| 2014/0120581 A1 | 5/2014 | Niwa et al. |
| 2015/0166661 A1 | 6/2015 | Chen et al. |
| 2015/0203579 A1 | 7/2015 | Papadopoulos et al. |
| 2015/0266966 A1 | 9/2015 | Smith et al. |
| 2016/0130347 A1 | 5/2016 | Bruenker et al. |
| 2016/0168247 A1 | 6/2016 | Van Den Brink et al. |
| 2016/0347839 A1 | 12/2016 | Davis et al. |
| 2017/0008951 A1 | 1/2017 | Block et al. |
| 2017/0051074 A1 | 2/2017 | Kirshner et al. |
| 2018/0104357 A1 | 4/2018 | Rudge et al. |
| 2018/0112001 A1 | 4/2018 | Haber et al. |
| 2018/0118848 A1 | 5/2018 | Haber et al. |
| 2018/0303953 A1 | 10/2018 | Van Berkel et al. |
| 2019/0127480 A1 | 5/2019 | Kirshner et al. |
| 2019/0389966 A1 | 12/2019 | Crawford |
| 2020/0317810 A1 | 10/2020 | Haber et al. |

FOREIGN PATENT DOCUMENTS

| | | |
|---|---|---|
| EP | 1176981 B1 | 11/2005 |
| EP | 1185299 B1 | 1/2007 |
| EP | 2447372 A2 | 5/2012 |
| EP | 2500353 A2 | 9/2012 |
| EP | 2918604 A1 | 9/2015 |
| WO | 97/028267 A1 | 8/1997 |
| WO | 99/043713 A1 | 9/1999 |
| WO | 99/058572 A1 | 11/1999 |
| WO | 00/042072 A2 | 7/2000 |
| WO | 03/026490 A2 | 4/2003 |
| WO | 04/106380 A2 | 9/2004 |
| WO | 04/106383 A1 | 12/2004 |
| WO | 05/000901 A2 | 1/2005 |
| WO | 05/040220 A1 | 5/2005 |
| WO | 2005/118635 A3 | 12/2005 |
| WO | 06/130458 A2 | 12/2006 |
| WO | 07/024715 A2 | 3/2007 |
| WO | 07/042261 A2 | 4/2007 |
| WO | 07/093630 A1 | 8/2007 |
| WO | 08/076379 A3 | 6/2008 |
| WO | 08/119567 A2 | 10/2008 |
| WO | 2008/147143 A2 | 12/2008 |
| WO | 09/018411 A1 | 2/2009 |
| WO | 09/023540 A1 | 2/2009 |
| WO | 2009/030368 A1 | 3/2009 |
| WO | 2009/106096 A1 | 9/2009 |
| WO | 10/054212 A1 | 5/2010 |
| WO | 10/063785 A2 | 6/2010 |
| WO | 10/085682 A2 | 7/2010 |
| WO | 2010/151792 A1 | 12/2010 |
| WO | 11/090762 A1 | 7/2011 |
| WO | 11/137362 A1 | 11/2011 |
| WO | 12/022982 A2 | 2/2012 |
| WO | 12/035141 A1 | 3/2012 |
| WO | 12/073985 A1 | 6/2012 |
| WO | 12/087746 A1 | 6/2012 |
| WO | 12/109285 A2 | 8/2012 |
| WO | 2012/162067 A2 | 11/2012 |
| WO | 13/012733 A1 | 1/2013 |
| WO | 13/026839 A1 | 2/2013 |
| WO | 2013/072406 A1 | 5/2013 |
| WO | 2013/072415 A1 | 5/2013 |
| WO | 13/112986 A1 | 8/2013 |
| WO | 2013/157105 A1 | 10/2013 |
| WO | 13/184761 A1 | 12/2013 |
| WO | 14/012085 A2 | 1/2014 |
| WO | 14/022540 A1 | 2/2014 |
| WO | 14/047231 A1 | 3/2014 |
| WO | 14/051433 A1 | 4/2014 |
| WO | 14/056783 A1 | 4/2014 |
| WO | 14/121087 A1 | 8/2014 |
| WO | 15/006749 A2 | 1/2015 |

(56) References Cited

FOREIGN PATENT DOCUMENTS

| WO | 15/091738 | A1 | 6/2015 |
|---|---|---|---|
| WO | 15/143079 | A1 | 9/2015 |
| WO | 16/081490 | A1 | 5/2016 |
| WO | 16/161010 | A2 | 10/2016 |
| WO | 17/053856 | A1 | 3/2017 |
| WO | 17/112762 | A1 | 6/2017 |
| WO | 18/093821 | A1 | 5/2018 |
| WO | 2021/021469 | A1 | 2/2021 |

OTHER PUBLICATIONS

Advani et al., "New immune strategies for the treatment of acute pymphoblastic leukemia: antiobodies and chimeric antigen receptors," Hematology, vol. 2013 (No. 1): (Dec. 1, 2013).

Alegre et al., "Effect of a Single Amino Acid Mutation on the Activating and Immunosuppressive Properties of a Humanized OKT3 Monoclonal Antibody", J Immunol, 148(11):3461-3468, ISSN: 0022-1767, (1992).

Almagro et al., "Humanization of antibodies," Front Biosci, vol. 13, pp. 1619-163, (2008).

An et al., "IgG2m4, an engineered antibody isotype with reduced Fc function," Landes Bioscience, 1(6):572-579, (2009).

Anonymous, "Clinical Trails Register: A Phase I Study to Assess Safety and Tolerability of REGN1979, an anti-CD20 x anti-CD3 bispecific monoclonal antibody, and REGN2810, and anti-programmed death-1 (PD-1) monoclonal antibody, in Patients with B-cell Malignancies," p. 1, section A.3; p. 3, section E.1 [Retrieved from the Internet Mar. 14, 2017: <URL: https://www.clinicaltrailsregister.eu/ctr-search/trial/2015-001697-17/ES>].

Anonymous, "Study of REGN2810 and REGN1979 in Patients with Lymphoma or Acute Lymphoblastic Leukemia." [Retrieved from the Internet Mar. 15, 2017: <URL: https://www.api.liveclinicaltrials.com/trialpage?dcn=10963&city=Baltimore&country=UnitedStates&start=20&state=Maryland&conditions=lymphoma&id=207048402254>].

Armour et al., "Differential binding to human FcγRlla and FcγRllb receptors by human IgG wildtype and mutant antibodies," Molecular Immunology, 40:585-593, (2003).

Armour et al., "Recombinant human IgG molecules lacking Fcγ receptor I binding and monocyte triggering activities", J. Immunol., 29: 2613-2624, (1999).

Baeuerle et al., "Bispecific T-cell engaging antibodies for cancer therapy," Cancer Res, 69(12):4941-4944, doi: 10.1158/0008-5472.CAN-09-0547, (2009).

Bargou et al., "Tumor egression in Cancer Patients by Very Low Doses of a T Cell-Engaging Antibody," Science Magazine, vol. 321: 974-977, (2008).

Becker et al., "Evaluation of a combinatorial cell engineering approach to overcome apoptotic effects in XBP-1(s) expressing cells," Journal of Biotechnology, vol. 164:198-206, (2010).

Blincyto (blinatumomab) for injection, for intravenous use Initial U.S. Approval: 2014, "Highlights of Prescribing Information," package insert.

Bloom et al., "Intrachain disulfide bond in the core hinge region of human IgG4," Protein Science, 6:407-415, (1997).

Boehrer et al., "Cytotoxic effects of the trifunctional bispecific antibody FBTACl5 in ex-vivo cells of chronic lymphocytic leukemia depend on immune-mediated mechanisms," Anti-Cancer Drugs, 22:519-530, (2011).

Brekke et al., "The structural requirements for complement activation by IgG: does it hinge on the hinge?" Today, 16(2):85-90, (1995).

Brownstein et al., "First-in-human study assessing safety and tolerability of REGN1979, a novel CD20×CD3 bispecific antibody, in patients with CD20+ B-cell malignancies previously treated with anti-CD20 therapy," American Society of Clinical Oncology 51st Annual Scientific Meeting, May 29-Jun. 2, 2015; Chicago, IL; 1 page.

Buhmann et al., "Immunotherapy of recurrent B-cell malignancies after allo-SCT with Bi20 (FBTA05), a trifunctional anti-CD3×anti-CD20 antibody and donor lymphocyte infusion," Bone Marrow Transplantation, 43:383-397, (2009).

Buhmann et al., "Immunotherapy with FBTA05 (Bi20), a trifunctional bispecific anti-CD3×anti-CD20 antibody and donor lymphocyte infusion (DLI) in relapsed or refractory B-cell lymphoma after allogeneic stem cell transplantation: study protocol of an investigator-driven, open-label, non-randomized, uncontrolled, dose-escalating Phase I/II-trial," Journal of Translation Medicine, vol. 11:160, (2013); 9 pages. [Retrieved from the Internet at: <http://www.translational-medicine.eom/content/11/1/1160>].

Canfield et al., "The Binding Affinity of Human Igg for Its High Affinity FC Receptor is Determined by Multiple Amino Acids in the Ch2 Domain and is Modulated by the Hinge Region," J. Exp. Med., 173(6):1483-1491, (1991).

Cao et al., "Multiformat T-Cell-Engaging Bispecific Antibodies Targeting Human Breast Cancers," Angew Chern Int Ed Engl, 54(24):7022-7027, doi: 10.1002/anie.201500799, (2015).

Carter, "Potent Antibody Therapeutics by Design," Journal of Immunology, Nature Pub. Group, 6:343-357, (2006).

Chappel et al., "Identification of a Secondary FcγRI Binding Site within a Genetically Engineered Human IgG," Journal of Biological Chemistry, 268(33): 25124-25131, (1993).

Chappel et al., "Identification of the FC-Gamma Receptor Class 1 Binding Site in Human Igg Through the Use of Recombinant Igg1-Igg2 Hybrid and Point-Mutated Antibodies," Proc. Natl. Acad. Sci. USA, 88(20):9036-9040, (1991).

Clark, "IgG Effector Mechanisms," Chern Immunol. Basel, Karger, 65:88-110, (1997).

Conrad et al., "TCR and CD3 Antibody Cross-Reactivity in 44 Species," Cytometry Part A, 71A:925-933, (2007).

Dall'Acqua et al., "Modulation of the Effector Functions of a Human IgG1 through Engineering of Its Hinge Region," Journal of Immunology, 177:1129-1138, (2006).

Damschroder et al., "Analysis of human and primate CD2 molecules by protein sequence and epitope mapping with anti-human CD2 antibodies," Molecular Immunology, vol. 41:985-1000, (2004).

Dangl et al., "Segmental flexibility and complement fixation of genetically engineered chimeric human, rabbit and mouse antibodies," The EMBO Journal, 7(7):1989-1994, (1988).

Duncan et al., "Localization of the binding site for the human high-affinity Fc receptor on IgG", Nature, 332:563-564, (1988).

Fossati et al., "Immunological changes in the ascites of cancer patients after intraperitoneal administration of the bispecific antibody catumaxomab (anti-EpCAManti-CD3)," Gynecol Oncol, 138(2):343-351, doi: 10.1016/J.YGYNO.2015.06.003, (2015).

Gall et al., "T cells armed with anti-CD3×anti-CD20 bispecific antibody enhance killing of CD20+ malignant B cells and bypass complement-mediated rituximab resistance in vitro", Experimental Hematology, 33(4):452-459, (2005).

Gergely et al., "The two binding-site models of human IgG binding Fcγ receptors", The FASEB Journal, 4:3275-3283, (1990).

Greenwood et al., "Structural Motifs Involved In Human IGG Antibody Effector Functions," Eur. J. Immunology, 23(5):1098-1104, (1993).

Grubb, "Human Immunoglobulin Allotypes and Mendelian Polymorphisms of the Human Immunoglobulin Genes," in Oss CJ, Regenmortel MHV (eds); Immunochemistry, New York, Dekker (1994); pp. 47-68.

Harlow et al., Antibodies, A Laboratory Manual, Cold Spring Harbor Laboratory; (1998) pp. 37-47.

Haso et al., "Anti-CD22-chimeric antigen receptors targeting B-cell precursor acute lymophoblastic leukemia," Blood, vol. 121(No. 7):1165-1174, (2013).

Hezareh et al., "Effector function activities of a panel of mutants of a broadly neutralizing antibody against human immunodeficiency virus type 1," J Virol, 75(24):12161-12168, doi: 10.1128/JVI.75.24.12161-12168.2001, (2001).

Jacobsen et al., "Molecular and Functional Characterization of Cynomolgus Monkey IgG Subclasses," Journal Immunology, 186:341-349, (2011).

(56) References Cited

OTHER PUBLICATIONS

Jefferis et al., "Interaction sites on human IgG-Fc for FcγR: current models", Immunology Letters, 82:57-65, (2002).
Jefferis et al., "Recognition sites on human IgG for Fcγ receptors: the role of glycosylation," Immunology Letters, 44:111-117, (1995).
Jung et al., "Target Cell-Induced T Cell Activation with Bi- and Trispecific Antibody Fragments", Eur J Immunol, vol. 21, pp. 2431-2435, doi: 10.1002/EJI.1830211020, (1991).
Kapur et al., "IgG-effector functions: The Good, The Bad and The Ugly," El Sevier, vol. 160:139-144, (2014).
Kazutomo, Biochemical Encyclopedia, 1998, 3rd Edition, pp. 265 to 266.
Klein et al., "Progress in overcoming the chain association issue in bispecific heterodimeric IgG antibodies," mAbs, Landes Bioscience, 4(6):1-11, (2012).
Klinger et al., "Immunopharmacologic response of patients with B-lineage acute lymphoblastic leukemia to continuous infusion of T cell-engaging CD19/CD3-bispecific BiTE antibody blinatumomab," Blood, 119:6226-6233, (2012).
Kontermann, "Dual targeting strategies with bispecific antibodies," mAbs, Landes Bioscience, 4(2):182-197, (2012).
Köhnke et al., "Increase of PD-L1 expressing B-precursor ALL cells in a patient resistant to the CD19/CD3-bispecific T cell engager antibody blinatumomab," Journal of Hematoloty & Oncology, vol. 8 (No. 111):5 pages, (2015).
Kumar et al., "Expression of CD20 in B Cell Precursor Acute Lymphoblastic Leukemia," Indian J. Hematol Blood Transfus, vol. 30 (No. 1):16-18, (2014).
Kung et al., "Monoclonal Antibodies Defining Distinctive Human T Cell Surface Antigens," Science, 206:347-349, (1979).
Labrijn et al., "When binding is enough: nonactivating antibody formats", Current Opinion in Immunology, 20:479-485, (2008).
Lau et al., "Chimeric Anti-CD14 IGG2/4 Hybrid Antibodies for Therapeutic Intervention in Pig and Human Models of Inflammation," J Immunol, 191:4769-4777, doi: 10.4049/jimmunol.1301653, (2013).
Le Tourneau et al., "Dose Escalation Methods in Phase I Cancer Clinical Trials," National Cancer Institute, vol. 101 (Issue 10): 708-720, (2009).
Leonard et al., "Targeted Treatment and New Agents in Diffuse Large B-Cell Lymphoma," Semin Hematol, 45(suppl 2):S11-S16, (2008).
Li et al., "A Novel Bispecific Antibody, S-Fab, Induces Potent Cancer Cell Killing," J Immunother, 38(9):350-356, doi: 10.1097/CJI.0000000000000099, (2015).
Liu et al., "Improvement in soluble expression levels of a diabody by exchanging expression vectors", Protein Expression and Purification, 62:15-20, (2008).
Lum et al., "CD2O-Targeted T Cells after Stem Cell Transplantation for High Risk and Refractory Non-Hodgkin's Lymphoma," Pbiol Blood Marrow Transplant, 19(6):925-933, (2013).
Lum et al., "Multiple infusions of CD20-targeted T cells and low-dose IL-2 after SCT for high-risk non-Hodgkin's lymphoma: A pilot study," Bone Marrow Transplantation, 49:73-79, (2004). [Puplished online Sep. 23, 2013].
Lund et al., "Human FcγRI and FcγRII Interact with Distinct but Overlapping Sites on Human IgG", Journal of Immunology, 147(8):2657-2662, (1991).
Maude et al., "Managing Cytokine Release Syndrome Associated With Novel T Cell-Engaging Therapies," Cancer Journal, vol. 20(2): 119-122, (2014).
Michaelsen et al., "Antibody Dependent Cell-Mediated Cytotoxicity Induced by Chimeric Mouse-Human IgG Subclasses and IgG3 Antibodies with Altered Hinge Region," Molecular Immunology, 29(3):319-326, (1992).
Morgan et al., "The N-terminal end of the CH2 domain of chimeric human IgGl anti-HLA-DR is necessary for Gig, FcγRI and FcγRII binding," Immunology, 86:319-324, (1995).

Mueller et al., "Humanized Porcine VCAM-Specific Monoclonal Antibodies with Chimeric IgG2/G4 Constant Regions Block Human Leukocyte Binding to Porcine Endothelial Cells," Molecular Immunology, 34(6): 441-452, (1997).
Nagorsen et al., "Blinatumomab: A historical perspective," Pharmacology & Therapeutics, 136:334-342 (2012).
Natsume et al., "Engineered Antibodies of IgG1IgG3 Mixed Isotype with Enhanced Cytotoxic Activities," Cancer Research, 68:(10):3863-3872, (2008).
NCBI MedGen 44126 definition for "Pre-B Acute Lymphoblastic Leukemia" retrieved from the Internet on Dec. 11, 2018; pp. 1-4, available at <https://www.ncbi.nlm.nih.gov/medgen/44126> (2018).
Oganesyan et al., "Structural characterization of a human Fc fragment engineered for lack of effector functions," Acta Crystallographica Section D Biological Crystallography, D64:700-704, (2008).
Ontology Lookup Serviec, EFO 0000220, "acute lumphoblastic leukemia" retrieved from the Internet on Dec. 11, 2018, pp. 1-6; available at <httpx://www.ebi.ac.uk/ols/ontologies/efo/terms?short_form=EFO_0000220> (2018).
Patel et al., "IGG subclass variation of a monoclonal antibody binding to human Fc-gamma receptors", American Journal of Biochemistry and Biotechnology, 9(3):206-218, (2013).
Pessano et al., "The T3/T cell receptor complex: antigenic distinction between the two 20-kd T3 (T3-δ and T3-€) subunits," The EMBO Journal, 4(2):337-344, (1985).
Peters et al., "Engineering an Improved IgG4 Molecule with Reduced Disulfide Bond Heterogeneity and Increased Fab Domain Thermal Stability," Journal of Biological Chemistry, 287(29): 24525-24533, (2012).
Press Release: U.S. FDA Approves DARZALEX® (daratumumab) Split-Dosing Regimen, Feb. 12, 2019. (www.janssen.com).
Reddy et al., "Elimination of Fc Receptor-Dependent Effector Functions of a Modified IgG4 Monoclonal Antibody to Human CD4," Journal of Immunology, 164:1925-1933, (2000).
Rother et al., "Discovery and development of the complement inhibitor eculizumab for the treatment of paroxysmal nocturnal hemoglobinuna," Nature Biotechnology, 25(11):1256-1264, (2007).
Roux et al., "Comparisons of the ability of human IgG3 hinge mutants, IgM, IgE and IgA2, to form small immune complexes: Arole for flexibility and geometry," The Journal of Immunology, 161:4083-4090, (1998).
Roux et al., "Flexibility of Human IgG Subclasses," Journal of Immunology, 159:3372-3382, (1997).
Ruf et al., "Induction of a long-lasting antitumor immunity by a trifunctional bispecific antibody," Blood Journal, vol. 98, No. 9: 2526-2534, (2001).
Salfeld, "Isotype selection in antibody engineering," Nature Biotechnology, 25(12):1369-1372, (2007).
Sarmay et al., "Mapping and Comparison of the Interaction Sites on the Fc Region of IgG Responsible for Triggering Antibody Dependent Cellular Cytotoxicity (ADCC) through Different Types of Human Fcγ Receptor," Molecular Immunology, 29(5):633-639, (1992).
Sathish et al., "Challenges and approaches for the development of safer immunomodulatory biologies," Nature Reviews Drug Discovery, 12:306-324, (2013).
Schaefer et al., "Immunoglobulin domain crossover as a generic approach for the production of bispecific IgG antibodies," PNAS, 108(27):11187-11192, doi: 10.1073/pnas.1019002108, (2011).
Schuster et al., "Immunotherapy with the trifunctional anti-CD20×anti-CD3 antibody FBTA05 Lymphomun) in paediatric high-risk patients with recurrent CD20-positive B cell malignancies," British Journal of Haematolgy, vol. 69 (No. 1): (Apr. 11, 2015); pp. 90-102.
Segal et al., "Bispecific antibodies in cancer therapy," Current Opinion in Immunology, 11:558-562, (1999).
Sensel et al., "Amino Acid Differences in the N-Terminus of CH2 Influence the Relative Abilities of IgG2 and IgG3 to Activate Complement", Molecular Immunology, 34(14):1019-1029, (1997).
Shields et al., High resolution mapping of the binding site on human IgG1 for FcgammaRI, FcganmaRII, FcgammaRIII, and FcRn and design of IgG1 variants with improved binding to the FcgammaR, J Biol Chem, 276(9):6591-6604, doi: 10.1074/JBC.M009483200, (2001).

(56) References Cited

OTHER PUBLICATIONS

Siberil et al., "Molecular aspects of human FcyR interactions with IgG: Functional and therapeutic consequences," Immunology Letters, 106:111-118, (2006).
Siiman et al., "Cell Surface Receptor-Antibody Association Constants and Enumeration of Receptor Sites for Monoclonal Antibodies," Cytometry, 40:316-326, (2000).
Smith et al., "A novel, native-format bispecific antibody triggering T-cell killing of B-cell is Yobustly active in mouse tumor models and cynomolgus monkeys," Scientific Reports, vol. 5(No. 11):(Dec. 11, 2015); p. 17943.
Stanglmaier et al., "Bi20 (FBTA05), a novel trifunctional bispecific antibody (anti-CD20×anti-CD3), mediates efficient killing of B-cell lymphoma cells even with very low CD20 expression Tevels", Int. J. Cancer, 123(5):1181-1189, (2008).
Stel et al., "The role of B cell-mediated T cell costimulation in the efficacy of the T cell retargeting bispecific antibody BIS20x3," J Immunol, 173(10):6009-6016, (2004).
Stevenson, "Chemical Engineering at the Antibody Hinge," Chern Immunol. Basel, Karger, 65:57-72, (1997).
Strop et al., "Generating Bispecific Human IgGl and IgG2 Antibodies from Any Antibody Pair", J. Mol. Biol., 420(3):204-219, (2012).
Stubenrauch et al., "Impact of Molecular Processing in the Hinge Region of Therapeutic IgG4 Antibodies on Disposition Profiles in Cynomolgus Monkeys," Drug Metabolism and Disposition, vol. 38(No. 1):84-91, (2010).
Sun et al., "Anti-CD20/CD3 T cell-dependent bispecific antibody for the treatment of B cell malignancies," Science Translational Medicine, 7(287):287ra70, 10 pages, (2015).
Tan et al., "Influence of the hinge region on complement activation, C1q binding, and segmental flexibility in chimeric human immunoglobulins,", Proc. Natl. Acad. Sci. USA, 87:162-166, (1990).
Teeling et al., "Characterization of new human CD20 monoclonal antibodies with potent cytolytic activity against non-Hodgkin lymphomas," Blood, 104:1793-1800, (2004).
Thakur et al., "Activated T cells from umbilical cord blood armed with anti-CD3×anti-CD20 bispecific antibody mediate specific cytotoxicity against CD20+ targets with minimal allogeneic reactivity: a strategy for providing antitumor effects after cord blood transplants", Transfusion, 52:63-75, (2012).
Thomas et al., "Chemiommunotherapy with a modified hyper-CVAD and Rituximab Regiment improves outcome in De Novo Philadelphia Chromosome-Negative Precursor B-Lineage Acute Lymphoblastic Leukemia," Journal of Clinical Oncology, vol. 28 (No. 24):3880-3889, 2010.
Topp et al., "Safety and activity of blinatumomab for adult patients with relapsed or refractory B-precursor acute lymphoblastic leu,aemia: a multiventre, single-arm, phase 2 study," The Lancet, vol. 16:57-66, (2015).
Tsai et al., "Regulation of CD20 in Rituximab-Resistant Cell Lines and B-cell Non-Hodgkin Lymphoma," Clinical Cancer Research, vol. 18(No. 4):1039-1050, (2012).
U.S. Appl. No. 14/031,075, Final Office Action dated Sep. 14, 2016.
U.S. Appl. No. 14/031,075, Non-Final Office Action dated Apr. 15, 2016.
U.S. Appl. No. 14/031,075, Notice of Allowance dated Jan. 18, 2014.
U.S. Appl. No. 14/031,075, Requirement for Restriction/Election dated Nov. 19, 2015.
U.S. Appl. No. 14/170,166, Non-Final Office Action dated Dec. 21, 2015.
U.S. Appl. No. 14/170,166, Notice of Allowance dated Apr. 11, 2016.
U.S. Appl. No. 14/170,166, Requirement for Restriction/Election dated Jul. 27, 2015.
U.S. Appl. No. 14/661,334, Requirement for Restriction/Election dated Mar. 6, 2017.
U.S. Appl. No. 14/661,334, Requirement for Restriction/Election dated Sep. 11, 2017.
U.S. Appl. No. 14/661,334, Non-Final Office Action dated Dec. 18, 2018.
U.S. Appl. No. 14/661,334, Final Office Action dated Jun. 27, 2019.
U.S. Appl. No. 14/661,334, Notice of Allowance dated Sep. 17, 2019.
U.S. Appl. No. 15/147,791, Non-Final Office Action dated Sep. 27, 2017.
U.S. Appl. No. 15/147,791, Notice of Allowance dated Mar. 1, 2018.
U.S. Appl. No. 15/147,791, Notice of Allowance dated Jun. 12, 2018.
U.S. Appl. No. 15/386,443, Requirement for Restriction/Election dated Apr. 20, 2018.
U.S. Appl. No. 15/386,443, Requirement for Restriction/Election dated Sep. 19, 2018.
U.S. Appl. No. 15/386,443, Non-Final Office Action dated Dec. 18, 2018.
U.S. Appl. No. 15/934,447, Requirement for Restriction/Election dated Oct. 17, 2019.
U.S. Appl. No. 15/489,666, Requirement for Restriction/Election dated Jun. 18, 2019.
U.S. Appl. No. 15/527,002, Requirement for Restriction/Election dated Aug. 24, 2018.
U.S. Appl. No. 15/527,002, Non-Final Office Action dated Mar. 8, 2019.
U.S. Appl. No. 15/562,881, Notice of Allowance dated Jun. 12, 2019.
U.S. Appl. No. 15/562,881, Notice of Allowance dated Sep. 25, 2019.
Vafa, et al., "An engineered Fc variant of an IgG eliminates all immune effector functions via structural perturbations", 65:114-126, (2014). (Published online Jul. 17, 2013).
Van Meerten et al., "CD20-Targeted Therapy: The Next Generation of Antibodies," Semin Hematol, 47:199-210, (2010).
Venclexta (venetoclax) tablets, for oral use Initial U.S. Approval: 2016; "Highlights of Prescribing Information.," package insert.
Vidarsson et al., "IgG Subclasses and Allotypes: From Structure to Effector Functions," Frontiers in Immunology, vol. 5, Article 520, 18 pages, doi: 10.3389/fimmu.2014.00520, (2014).
Ward et al., "The effector functions of immunoglobulins: implications for therapy," Therapeutic Immunology, 2:77-94, (1995).
Wark et al., "Latest technologies for the enhancement of antibody affinity", Advanced Drug Delivery Reviews, 58(5-6):657-670, (2006).
Wang et al., "Treatment of CD33-directed Chimeric Antigen Receptor-modified T Cells in One Patient With Relapsed and Refractory Acute Myeloid Leukemia," The American Society of Gene & Cell Therapy, vol. 23 (No. 1), 184-191 (2015).
Winkler et al., "Changing the Antigen Binding Specificity by Single Point Mutations of an Anti-p24 (HIV-1) Antibody," J. Immunol., 165:4505-4514, (2000).
WIPO Application No. PCT/US2013/060511, PCT International Search Report and Written Opinion of the International Searching Authority dated Feb. 20, 2014.
WIPO Application No. PCT/US2014/014175, PCT International Preliminary Report on Patentability dated Aug. 13, 2015.
WIPO Application No. PCT/US2014/014175, PCT International Search Report and Written Opinion of the International Searching Authority dated Jul. 9, 2014.
WIPO Application No. PCT/US2015/021322, PCT International Search Report and Written Opinion of the International Searching Authority dated Jul. 2, 2015.
WIPO Application No. PCT/US2015/061139, PCT International Search Report and Written Opinion of the International Searching Authority dated Feb. 18, 2016.
WIPO Application No. PCT/US2016/025051, PCT International Search Report and Written Opinion of the International Searching Authority dated Oct. 12, 2016.
WIPO Application No. PCT/US2016/053525, PCT International Search Report and Written Opinion of the International Searching Authority dated Mar. 8, 2017.
WIPO Application No. PCT/US2016/068003, PCT International Search Report dated Mar. 31, 2017.

(56) References Cited

OTHER PUBLICATIONS

WIPO Application No. PCT/US2016/068003, PCT Written Opinion of the International Searching Authority dated Mar. 31, 2017.
WIPO Application No. PCT/US2019/049027, PCT International Search Report and Written Opinion of the International Searching Authority dated Nov. 28, 2019.
Wolach et al., "Blinatumomab for the Treatment of Philadelphia Chromosome-Negative, Precursor B-cell Acute Lymphoblastic Leukemia," Clinical Cancer Research, vol. 21 (No. 19):4262-4269, (2015).
Wu et al., "Fab-based bispecific antibody formats with robust biophysical properties and biological activity," MABS, pp. 470-482, ISSN: 1942-0870, (2015).
Wypych et al., "Human IgG2 Antibodies Display Disulfide-mediated Structural Isoforms," Journal of Biological Chemistry, 283(23):16194-16205, (2008).
Xiong et al., "Efficient inhibition of human B-cell lymphoma xenografts with an anti-CD20×anti-CD3 bispecific diabody", Cancer Letters, 177:29-39, (2002).
Xu et al., "Residue at Position 331 in the Igg1 and Igg4 Ch2 Domains Contributes to Their Differential Ability to Blind and Activate Complement," Journal of Biological Chemistry, 269(5):3469-3474, (1994).
Aklilu et al., "Depletion of normal B cells with rituximab as an adjunct to IL-2 therapy for renal cell carcinoma and melanoma," Annals of Oncology 15: 1109-1114; Chicago, IL (2004).
Bae et al., "Identification of the amino acid residues involved in human IgG transport into egg yolk of Japanese quail," Molucular Immunology, vol. 47:1404-1410, (2010).
Bortoletto et al., "Optimizing anti-CD3 affinity for effective T cell targeting against tumor cells," Eur. J. Immunol., vol. 32:3102-3107, (2002).
Chan et al., "Therapeutic antibodies for autoimmunity and inflammation," Macmillan Publishers Limited (Nature Reviews, Immunology), vol. (10):301-316, (2010).
Chen et al., "Strategies for Generating Diverse Antibody Reportoires Using Transgenic Animals Expressing Human Antibodies," Front. Immunol. vol. 9, Article 460; Mar. 2018; 7 pages, doi: 10.3389/fimmu.2018.00460.
Richards et al., "Optimization of antibody binding to FcγRIIa enhances macrophage phagocytosis of tumor cells," Molecular Cancer Therapeutics (Xencor, Inc.), vol. (8):2517-2527, (2008). [Retrieved from the Internet Sep. 16, 2020: <URL: met.aacrjournals.org>].
Scott et al., "Antibody Therapy of Cancer," Nature, vol. 12:278-287, (Apr. 2012).
Sun, "Structural Recognition of Immunoglobulins by Fcγ Receptors," Elsevier Science & Technology, Ch. 7:131-144, (2013).
U.S. Appl. No. 15/527,002, Notice of Allowance dated Jan. 13, 2020.
U.S. Appl. No. 15/489,666, Non-Final Office Action dated Feb. 11, 2020.
U.S. Appl. No. 15/780,504, Requirement for Restriction/Election dated Apr. 7, 2020.
U.S. Appl. No. 15/934,447, Non-Final Office Action dated May 8, 2020.
U.S. Appl. No. 15/489,666, Final Office Action dated Sep. 10, 2020.
U.S. Appl. No. 16/128,907, Non-Final Office Action dated Sep. 22, 2020.
U.S. Appl. No. 15/780,504, Non-Final Office Action dated Oct. 20, 2020.
U.S. Appl. No. 15/934,447, Final Office Action dated Dec. 4, 2020.
U.S. Appl. No. 15/489,666, Notice of Allowance dated Mar. 24, 2021.
U.S. Appl. No. 15/934,447, Notice of Allowance dated Jun. 24, 2021.
Weinglass et al., "Engineering Conformational Flexibility in the Lactose Permease of *Escherichia coli*: Use of Glycine-Scanning Mutagenesis to Rescue Mutant Glu325—Asp," Biochemistry, vol. 40:769-776, (2001).
Yuen et al., "B lymphocytes and cancer: a love-hate relationship," Trends Cancer Dec. 2016; 2(12): 747-757.
U.S. Appl. No. 16/720,623, Non-Final Office Action dated Feb. 14, 2022.
Removab 10 microgram concentrate for solution for infusion package; Annex 1; Summary of Product Characteristics, 1-44, package insert.

\* cited by examiner

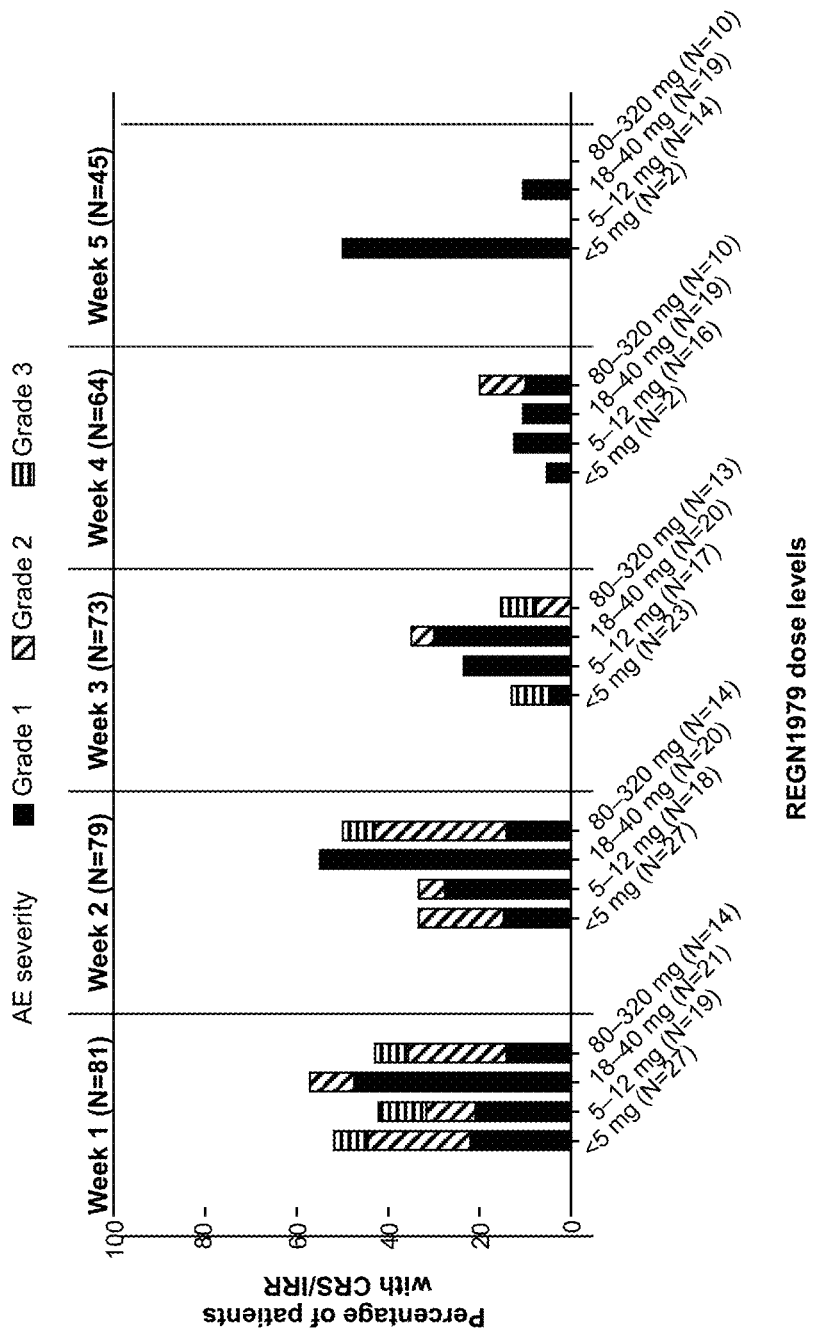

```
                         SEQUENCE LISTING

<160> NUMBER OF SEQ ID NOS: 24

<210> SEQ ID NO 1
<211> LENGTH: 207
<212> TYPE: PRT
<213> ORGANISM: Artificial Sequence
<220> FEATURE:
<223> OTHER INFORMATION: human CD3 Epsilon Protein (>NP_000724.1 T-cell
      surface glycoprotein CD3 epsilon chain precursor

<400> SEQUENCE: 1

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 2
<211> LENGTH: 171
<212> TYPE: PRT
<213> ORGANISM: Artificial Sequence
<220> FEATURE:
```

<223> OTHER INFORMATION: human CD3 Delta Protein (>NP_000723.1 T-cell
      surface glycoprotein CD3 delta chain isoform A
      precursor

<400> SEQUENCE: 2

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 3
<211> LENGTH: 164
<212> TYPE: PRT
<213> ORGANISM: Artificial Sequence
<220> FEATURE:
<223> OTHER INFORMATION: human CD3 Zeta Protein (>NP_932170.1 T-cell
      surface glycoprotein CD3 zeta chain isoform 1
      precursor

<400> SEQUENCE: 3

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

```
Leu Ser Thr Ala Thr Lys Asp Thr Tyr Asp Ala Leu His Met Gln Ala
145                 150                 155                 160

Leu Pro Pro Arg

<210> SEQ ID NO 4
<211> LENGTH: 182
<212> TYPE: PRT
<213> ORGANISM: Artificial Sequence
<220> FEATURE:
<223> OTHER INFORMATION: human CD3 Gamma Protein (>NP_000064.1 T-cell
      surface glycoprotein CD3 gamma chain precursor

<400> SEQUENCE: 4

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
                20                  25                  30

Val Tyr Asp Tyr Gln Glu Asp Gly Ser Val Leu Leu Thr Cys Asp Ala
            35                  40                  45

Glu Ala Lys Asn Ile Thr Trp Phe Lys Asp Gly Lys Met Ile Gly Phe
50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180

<210> SEQ ID NO 5
<211> LENGTH: 297
<212> TYPE: PRT
<213> ORGANISM: Artificial Sequence
<220> FEATURE:
<223> OTHER INFORMATION: human CD20 Protein

<400> SEQUENCE: 5

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
                20                  25                  30

Arg Met Ser Ser Leu Val Gly Pro Thr Gln Ser Phe Phe Met Arg Glu
            35                  40                  45

Ser Lys Thr Leu Gly Ala Val Gln Ile Met Asn Gly Leu Phe His Ile
        50                  55                  60

Ala Leu Gly Gly Leu Leu Met Ile Pro Ala Gly Ile Tyr Ala Pro Ile
65                  70                  75                  80
```

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
290                 295

<210> SEQ ID NO 6
<211> LENGTH: 184
<212> TYPE: PRT
<213> ORGANISM: Artificial Sequence
<220> FEATURE:
<223> OTHER INFORMATION: human BCMA (TNFRSF17) Protein NP_001183.2

<400> SEQUENCE: 6

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
        50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
130                 135                 140

-continued

```
Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180
```

<210> SEQ ID NO 7
<211> LENGTH: 750
<212> TYPE: PRT
<213> ORGANISM: Artificial Sequence
<220> FEATURE:
<223> OTHER INFORMATION: human PSMA (FOLH1) Protein

<400> SEQUENCE: 7

```
Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Asn Glu
            35                  40                  45

Ala Thr Asn Ile Thr Pro Lys His Asn Met Lys Ala Phe Leu Asp Glu
        50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
                100                 105                 110

Tyr Asp Val Leu Leu Ser Tyr Pro Asn Lys Thr His Pro Asn Tyr Ile
            115                 120                 125

Ser Ile Ile Asn Glu Asp Gly Asn Glu Ile Phe Asn Thr Ser Leu Phe
        130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320
```

-continued

Gly Ser Leu Lys Val Pro Tyr Asn Val Gly Pro Phe Thr Gly Asn
            325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
            355                 360                 365

Asp Arg Tyr Val Ile Leu Gly Gly His Arg Asp Ser Trp Val Phe Gly
370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
            405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
            450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
            485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
            530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
            565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
            610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
            645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
            725                 730                 735

-continued

Phe Thr Val Gln Ala Ala Ala Glu Thr Leu Ser Glu Val Ala
            740             745             750

<210> SEQ ID NO 8
<211> LENGTH: 14507
<212> TYPE: PRT
<213> ORGANISM: Artificial Sequence
<220> FEATURE:
<223> OTHER INFORMATION: human MUC16 (CA-125) Protein

<400> SEQUENCE: 8

Met Leu Lys Pro Ser Gly Leu Pro Gly Ser Ser Pro Thr Arg Ser
1               5               10              15

Leu Met Thr Gly Ser Arg Ser Thr Lys Ala Thr Pro Glu Met Asp Ser
            20              25              30

Gly Leu Thr Gly Ala Thr Leu Ser Pro Lys Thr Ser Thr Gly Ala Ile
            35              40              45

Val Val Thr Glu His Thr Leu Pro Phe Thr Ser Pro Asp Lys Thr Leu
    50              55              60

Ala Ser Pro Thr Ser Ser Val Val Gly Arg Thr Thr Gln Ser Leu Gly
65              70              75              80

Val Met Ser Ser Ala Leu Pro Glu Ser Thr Ser Arg Gly Met Thr His
                85              90              95

Ser Glu Gln Arg Thr Ser Pro Ser Leu Ser Pro Gln Val Asn Gly Thr
            100             105             110

Pro Ser Arg Asn Tyr Pro Ala Thr Ser Met Val Ser Gly Leu Ser Ser
        115             120             125

Pro Arg Thr Arg Thr Ser Ser Thr Glu Gly Asn Phe Thr Lys Glu Ala
    130             135             140

Ser Thr Tyr Thr Leu Thr Val Glu Thr Thr Ser Gly Pro Val Thr Glu
145             150             155             160

Lys Tyr Thr Val Pro Thr Glu Thr Ser Thr Thr Glu Gly Asp Ser Thr
                165             170             175

Glu Thr Pro Trp Asp Thr Arg Tyr Ile Pro Val Lys Ile Thr Ser Pro
            180             185             190

Met Lys Thr Phe Ala Asp Ser Thr Ala Ser Lys Glu Asn Ala Pro Val
        195             200             205

Ser Met Thr Pro Ala Glu Thr Thr Val Thr Asp Ser His Thr Pro Gly
    210             215             220

Arg Thr Asn Pro Ser Phe Gly Thr Leu Tyr Ser Ser Phe Leu Asp Leu
225             230             235             240

Ser Pro Lys Gly Thr Pro Asn Ser Arg Gly Glu Thr Ser Leu Glu Leu
                245             250             255

Ile Leu Ser Thr Thr Gly Tyr Pro Phe Ser Ser Pro Glu Pro Gly Ser
            260             265             270

Ala Gly His Ser Arg Ile Ser Thr Ser Ala Pro Leu Ser Ser Ser Ala
        275             280             285

Ser Val Leu Asp Asn Lys Ile Ser Glu Thr Ser Ile Phe Ser Gly Gln
    290             295             300

Ser Leu Thr Ser Pro Leu Ser Pro Gly Val Pro Glu Ala Arg Ala Ser
305             310             315             320

Thr Met Pro Asn Ser Ala Ile Pro Phe Ser Met Thr Leu Ser Asn Ala
                325             330             335

Glu Thr Ser Ala Glu Arg Val Arg Ser Thr Ile Ser Ser Leu Gly Thr
            340             345             350

-continued

Pro Ser Ile Ser Thr Lys Gln Thr Ala Glu Thr Ile Leu Thr Phe His
355                 360                 365

Ala Phe Ala Glu Thr Met Asp Ile Pro Ser Thr His Ile Ala Lys Thr
370                 375                 380

Leu Ala Ser Glu Trp Leu Gly Ser Pro Gly Thr Leu Gly Gly Thr Ser
385                 390                 395                 400

Thr Ser Ala Leu Thr Thr Thr Ser Pro Ser Thr Thr Leu Val Ser Glu
            405                 410                 415

Glu Thr Asn Thr His His Ser Thr Ser Gly Lys Glu Thr Glu Gly Thr
            420                 425                 430

Leu Asn Thr Ser Met Thr Pro Leu Glu Thr Ser Ala Pro Gly Glu Glu
            435                 440                 445

Ser Glu Met Thr Ala Thr Leu Val Pro Thr Leu Gly Phe Thr Thr Leu
450                 455                 460

Asp Ser Lys Ile Arg Ser Pro Ser Gln Val Ser Ser Ser His Pro Thr
465                 470                 475                 480

Arg Glu Leu Arg Thr Thr Gly Ser Thr Ser Gly Arg Gln Ser Ser Ser
            485                 490                 495

Thr Ala Ala His Gly Ser Ser Asp Ile Leu Arg Ala Thr Thr Ser Ser
            500                 505                 510

Thr Ser Lys Ala Ser Ser Trp Thr Ser Glu Ser Thr Ala Gln Gln Phe
            515                 520                 525

Ser Glu Pro Gln His Thr Gln Trp Val Glu Thr Ser Pro Ser Met Lys
530                 535                 540

Thr Glu Arg Pro Pro Ala Ser Thr Ser Val Ala Ala Pro Ile Thr Thr
545                 550                 555                 560

Ser Val Pro Ser Val Val Ser Gly Phe Thr Thr Leu Lys Thr Ser Ser
            565                 570                 575

Thr Lys Gly Ile Trp Leu Glu Glu Thr Ser Ala Asp Thr Leu Ile Gly
            580                 585                 590

Glu Ser Thr Ala Gly Pro Thr Thr His Gln Phe Ala Val Pro Thr Gly
            595                 600                 605

Ile Ser Met Thr Gly Gly Ser Thr Arg Gly Ser Gln Gly Thr Thr
            610                 615                 620

His Leu Leu Thr Arg Ala Thr Ala Ser Ser Glu Thr Ser Ala Asp Leu
625                 630                 635                 640

Thr Leu Ala Thr Asn Gly Val Pro Val Ser Val Ser Pro Ala Val Ser
            645                 650                 655

Lys Thr Ala Ala Gly Ser Ser Pro Pro Gly Gly Thr Lys Pro Ser Tyr
            660                 665                 670

Thr Met Val Ser Ser Val Ile Pro Glu Thr Ser Ser Leu Gln Ser Ser
            675                 680                 685

Ala Phe Arg Glu Gly Thr Ser Leu Gly Leu Thr Pro Leu Asn Thr Arg
            690                 695                 700

His Pro Phe Ser Ser Pro Glu Pro Asp Ser Ala Gly His Thr Lys Ile
705                 710                 715                 720

Ser Thr Ser Ile Pro Leu Leu Ser Ser Ala Ser Val Leu Glu Asp Lys
            725                 730                 735

Val Ser Ala Thr Ser Thr Phe Ser His His Lys Ala Thr Ser Ser Ile
            740                 745                 750

Thr Thr Gly Thr Pro Glu Ile Ser Thr Lys Thr Lys Pro Ser Ser Ala
            755                 760                 765

-continued

```
Val Leu Ser Ser Met Thr Leu Ser Asn Ala Ala Thr Ser Pro Glu Arg
    770                 775                 780

Val Arg Asn Ala Thr Ser Pro Leu Thr His Pro Ser Pro Ser Gly Glu
785                 790                 795                 800

Glu Thr Ala Gly Ser Val Leu Thr Leu Ser Thr Ser Ala Glu Thr Thr
                805                 810                 815

Asp Ser Pro Asn Ile His Pro Thr Gly Thr Leu Thr Ser Glu Ser Ser
                820                 825                 830

Glu Ser Pro Ser Thr Leu Ser Leu Pro Ser Val Ser Gly Val Lys Thr
            835                 840                 845

Thr Phe Ser Ser Ser Thr Pro Ser Thr His Leu Phe Thr Ser Gly Glu
    850                 855                 860

Glu Thr Glu Glu Thr Ser Asn Pro Ser Val Ser Gln Pro Glu Thr Ser
865                 870                 875                 880

Val Ser Arg Val Arg Thr Thr Leu Ala Ser Thr Ser Val Pro Thr Pro
                885                 890                 895

Val Phe Pro Thr Met Asp Thr Trp Pro Thr Arg Ser Ala Gln Phe Ser
                900                 905                 910

Ser Ser His Leu Val Ser Glu Leu Arg Ala Thr Ser Ser Thr Ser Val
            915                 920                 925

Thr Asn Ser Thr Gly Ser Ala Leu Pro Lys Ile Ser His Leu Thr Gly
    930                 935                 940

Thr Ala Thr Met Ser Gln Thr Asn Arg Asp Thr Phe Asn Asp Ser Ala
945                 950                 955                 960

Ala Pro Gln Ser Thr Thr Trp Pro Glu Thr Ser Pro Arg Phe Lys Thr
                965                 970                 975

Gly Leu Pro Ser Ala Thr Thr Thr Val Ser Thr Ser Ala Thr Ser Leu
            980                 985                 990

Ser Ala Thr Val Met Val Ser Lys  Phe Thr Ser Pro Ala  Thr Ser Ser
            995                 1000                1005

Met Glu  Ala Thr Ser Ile Arg  Glu Pro Ser Thr Thr  Ile Leu Thr
    1010                1015                1020

Thr Glu  Thr Thr Asn Gly Pro  Gly Ser Met Ala Val  Ala Ser Thr
    1025                1030                1035

Asn Ile  Pro Ile Gly Lys Gly  Tyr Ile Thr Glu Gly  Arg Leu Asp
    1040                1045                1050

Thr Ser  His Leu Pro Ile Gly  Thr Thr Ala Ser Ser  Glu Thr Ser
    1055                1060                1065

Met Asp  Phe Thr Met Ala Lys  Glu Ser Val Ser Met  Ser Val Ser
    1070                1075                1080

Pro Ser  Gln Ser Met Asp Ala  Ala Gly Ser Ser Thr  Pro Gly Arg
    1085                1090                1095

Thr Ser  Gln Phe Val Asp Thr  Phe Ser Asp Asp Val  Tyr His Leu
    1100                1105                1110

Thr Ser  Arg Glu Ile Thr Ile  Pro Arg Asp Gly Thr  Ser Ser Ala
    1115                1120                1125

Leu Thr  Pro Gln Met Thr Ala  Thr His Pro Pro Ser  Pro Asp Pro
    1130                1135                1140

Gly Ser  Ala Arg Ser Thr Trp  Leu Gly Ile Leu Ser  Ser Ser Pro
    1145                1150                1155

Ser Ser  Pro Thr Pro Lys Val  Thr Met Ser Ser Thr  Phe Ser Thr
    1160                1165                1170
```

-continued

```
Gln Arg Val Thr Thr Ser Met Ile Met Asp Thr Val Glu Thr Ser
1175                1180                1185

Arg Trp Asn Met Pro Asn Leu Pro Ser Thr Thr Ser Leu Thr Pro
1190                1195                1200

Ser Asn Ile Pro Thr Ser Gly Ala Ile Gly Lys Ser Thr Leu Val
1205                1210                1215

Pro Leu Asp Thr Pro Ser Pro Ala Thr Ser Leu Glu Ala Ser Glu
1220                1225                1230

Gly Gly Leu Pro Thr Leu Ser Thr Tyr Pro Glu Ser Thr Asn Thr
1235                1240                1245

Pro Ser Ile His Leu Gly Ala His Ala Ser Ser Glu Ser Pro Ser
1250                1255                1260

Thr Ile Lys Leu Thr Met Ala Ser Val Val Lys Pro Gly Ser Tyr
1265                1270                1275

Thr Pro Leu Thr Phe Pro Ser Ile Glu Thr His Ile His Val Ser
1280                1285                1290

Thr Ala Arg Met Ala Tyr Ser Ser Gly Ser Ser Pro Glu Met Thr
1295                1300                1305

Ala Pro Gly Glu Thr Asn Thr Gly Ser Thr Trp Asp Pro Thr Thr
1310                1315                1320

Tyr Ile Thr Thr Thr Asp Pro Lys Asp Thr Ser Ser Ala Gln Val
1325                1330                1335

Ser Thr Pro His Ser Val Arg Thr Leu Arg Thr Thr Glu Asn His
1340                1345                1350

Pro Lys Thr Glu Ser Ala Thr Pro Ala Ala Tyr Ser Gly Ser Pro
1355                1360                1365

Lys Ile Ser Ser Ser Pro Asn Leu Thr Ser Pro Ala Thr Lys Ala
1370                1375                1380

Trp Thr Ile Thr Asp Thr Thr Glu His Ser Thr Gln Leu His Tyr
1385                1390                1395

Thr Lys Leu Ala Glu Lys Ser Ser Gly Phe Glu Thr Gln Ser Ala
1400                1405                1410

Pro Gly Pro Val Ser Val Val Ile Pro Thr Ser Pro Thr Ile Gly
1415                1420                1425

Ser Ser Thr Leu Glu Leu Thr Ser Asp Val Pro Gly Glu Pro Leu
1430                1435                1440

Val Leu Ala Pro Ser Glu Gln Thr Thr Ile Thr Leu Pro Met Ala
1445                1450                1455

Thr Trp Leu Ser Thr Ser Leu Thr Glu Glu Met Ala Ser Thr Asp
1460                1465                1470

Leu Asp Ile Ser Ser Pro Ser Ser Pro Met Ser Thr Phe Ala Ile
1475                1480                1485

Phe Pro Pro Met Ser Thr Pro Ser His Glu Leu Ser Lys Ser Glu
1490                1495                1500

Ala Asp Thr Ser Ala Ile Arg Asn Thr Asp Ser Thr Thr Leu Asp
1505                1510                1515

Gln His Leu Gly Ile Arg Ser Leu Gly Arg Thr Gly Asp Leu Thr
1520                1525                1530

Thr Val Pro Ile Thr Pro Leu Thr Thr Thr Trp Thr Ser Val Ile
1535                1540                1545

Glu His Ser Thr Gln Ala Gln Asp Thr Leu Ser Ala Thr Met Ser
1550                1555                1560
```

```
Pro Thr His Val Thr Gln Ser  Leu Lys Asp Gln Thr  Ser Ile Pro
    1565             1570                  1575

Ala Ser Ala Ser Pro Ser His  Leu Thr Glu Val Tyr  Pro Glu Leu
    1580             1585                  1590

Gly Thr Gln Gly Arg Ser Ser  Ser Glu Ala Thr Thr  Phe Trp Lys
    1595             1600                  1605

Pro Ser Thr Asp Thr Leu Ser  Arg Glu Ile Glu Thr  Gly Pro Thr
    1610             1615                  1620

Asn Ile Gln Ser Thr Pro Pro  Met Asp Asn Thr Thr  Thr Gly Ser
    1625             1630                  1635

Ser Ser Ser Gly Val Thr Leu  Gly Ile Ala His Leu  Pro Ile Gly
    1640             1645                  1650

Thr Ser Ser Pro Ala Glu Thr  Ser Thr Asn Met Ala  Leu Glu Arg
    1655             1660                  1665

Arg Ser Ser Thr Ala Thr Val  Ser Met Ala Gly Thr  Met Gly Leu
    1670             1675                  1680

Leu Val Thr Ser Ala Pro Gly  Arg Ser Ile Ser Gln  Ser Leu Gly
    1685             1690                  1695

Arg Val Ser Ser Val Leu Ser  Glu Ser Thr Thr Glu  Gly Val Thr
    1700             1705                  1710

Asp Ser Ser Lys Gly Ser Ser  Pro Arg Leu Asn Thr  Gln Gly Asn
    1715             1720                  1725

Thr Ala Leu Ser Ser Ser Leu  Glu Pro Ser Tyr Ala  Glu Gly Ser
    1730             1735                  1740

Gln Met Ser Thr Ser Ile Pro  Leu Thr Ser Ser Pro  Thr Thr Pro
    1745             1750                  1755

Asp Val Glu Phe Ile Gly Gly  Ser Thr Phe Trp Thr  Lys Glu Val
    1760             1765                  1770

Thr Thr Val Met Thr Ser Asp  Ile Ser Lys Ser Ser  Ala Arg Thr
    1775             1780                  1785

Glu Ser Ser Ser Ala Thr Leu  Met Ser Thr Ala Leu  Gly Ser Thr
    1790             1795                  1800

Glu Asn Thr Gly Lys Glu Lys  Leu Arg Thr Ala Ser  Met Asp Leu
    1805             1810                  1815

Pro Ser Pro Thr Pro Ser Met  Glu Val Thr Pro Trp  Ile Ser Leu
    1820             1825                  1830

Thr Leu Ser Asn Ala Pro Asn  Thr Thr Asp Ser Leu  Asp Leu Ser
    1835             1840                  1845

His Gly Val His Thr Ser Ser  Ala Gly Thr Leu Ala  Thr Asp Arg
    1850             1855                  1860

Ser Leu Asn Thr Gly Val Thr  Arg Ala Ser Arg Leu  Glu Asn Gly
    1865             1870                  1875

Ser Asp Thr Ser Ser Lys Ser  Leu Ser Met Gly Asn  Ser Thr His
    1880             1885                  1890

Thr Ser Met Thr Tyr Thr Glu  Lys Ser Glu Val Ser  Ser Ser Ile
    1895             1900                  1905

His Pro Arg Pro Glu Thr Ser  Ala Pro Gly Ala Glu  Thr Thr Leu
    1910             1915                  1920

Thr Ser Thr Pro Gly Asn Arg  Ala Ile Ser Leu Thr  Leu Pro Phe
    1925             1930                  1935

Ser Ser Ile Pro Val Glu Glu  Val Ile Ser Thr Gly  Ile Thr Ser
    1940             1945                  1950
```

-continued

Gly Pro Asp Ile Asn Ser Ala Pro Met Thr His Ser Pro Ile Thr
1955              1960             1965

Pro Pro Thr Ile Val Trp Thr Ser Thr Gly Thr Ile Glu Gln Ser
1970              1975             1980

Thr Gln Pro Leu His Ala Val Ser Ser Glu Lys Val Ser Val Gln
1985              1990             1995

Thr Gln Ser Thr Pro Tyr Val Asn Ser Val Ala Val Ser Ala Ser
2000              2005             2010

Pro Thr His Glu Asn Ser Val Ser Ser Gly Ser Ser Thr Ser Ser
2015              2020             2025

Pro Tyr Ser Ser Ala Ser Leu Glu Ser Leu Asp Ser Thr Ile Ser
2030              2035             2040

Arg Arg Asn Ala Ile Thr Ser Trp Leu Trp Asp Leu Thr Thr Ser
2045              2050             2055

Leu Pro Thr Thr Thr Trp Pro Ser Thr Ser Leu Ser Glu Ala Leu
2060              2065             2070

Ser Ser Gly His Ser Gly Val Ser Asn Pro Ser Ser Thr Thr Thr
2075              2080             2085

Glu Phe Pro Leu Phe Ser Ala Ala Ser Thr Ser Ala Ala Lys Gln
2090              2095             2100

Arg Asn Pro Glu Thr Glu Thr His Gly Pro Gln Asn Thr Ala Ala
2105              2110             2115

Ser Thr Leu Asn Thr Asp Ala Ser Ser Val Thr Gly Leu Ser Glu
2120              2125             2130

Thr Pro Val Gly Ala Ser Ile Ser Ser Glu Val Pro Leu Pro Met
2135              2140             2145

Ala Ile Thr Ser Arg Ser Asp Val Ser Gly Leu Thr Ser Glu Ser
2150              2155             2160

Thr Ala Asn Pro Ser Leu Gly Thr Ala Ser Ser Ala Gly Thr Lys
2165              2170             2175

Leu Thr Arg Thr Ile Ser Leu Pro Thr Ser Glu Ser Leu Val Ser
2180              2185             2190

Phe Arg Met Asn Lys Asp Pro Trp Thr Val Ser Ile Pro Leu Gly
2195              2200             2205

Ser His Pro Thr Thr Asn Thr Glu Thr Ser Ile Pro Val Asn Ser
2210              2215             2220

Ala Gly Pro Pro Gly Leu Ser Thr Val Ala Ser Asp Val Ile Asp
2225              2230             2235

Thr Pro Ser Asp Gly Ala Glu Ser Ile Pro Thr Val Ser Phe Ser
2240              2245             2250

Pro Ser Pro Asp Thr Glu Val Thr Thr Ile Ser His Phe Pro Glu
2255              2260             2265

Lys Thr Thr His Ser Phe Arg Thr Ile Ser Ser Leu Thr His Glu
2270              2275             2280

Leu Thr Ser Arg Val Thr Pro Ile Pro Gly Asp Trp Met Ser Ser
2285              2290             2295

Ala Met Ser Thr Lys Pro Thr Gly Ala Ser Pro Ser Ile Thr Leu
2300              2305             2310

Gly Glu Arg Arg Thr Ile Thr Ser Ala Ala Pro Thr Thr Ser Pro
2315              2320             2325

Ile Val Leu Thr Ala Ser Phe Thr Glu Thr Ser Thr Val Ser Leu
2330              2335             2340

```
Asp Asn Glu Thr Thr Val Lys Thr Ser Asp Ile Leu Asp Ala Arg
2345                2350                2355

Lys Thr Asn Glu Leu Pro Ser Asp Ser Ser Ser Ser Asp Leu
2360                2365                2370

Ile Asn Thr Ser Ile Ala Ser Ser Thr Met Asp Val Thr Lys Thr
2375                2380                2385

Ala Ser Ile Ser Pro Thr Ser Ile Ser Gly Met Thr Ala Ser Ser
2390                2395                2400

Ser Pro Ser Leu Phe Ser Ser Asp Arg Pro Gln Val Pro Thr Ser
2405                2410                2415

Thr Thr Glu Thr Asn Thr Ala Thr Ser Pro Ser Val Ser Ser Asn
2420                2425                2430

Thr Tyr Ser Leu Asp Gly Gly Ser Asn Val Gly Thr Pro Ser
2435                2440                2445

Thr Leu Pro Pro Phe Thr Ile Thr His Pro Val Glu Thr Ser Ser
2450                2455                2460

Ala Leu Leu Ala Trp Ser Arg Pro Val Arg Thr Phe Ser Thr Met
2465                2470                2475

Val Ser Thr Asp Thr Ala Ser Gly Glu Asn Pro Thr Ser Ser Asn
2480                2485                2490

Ser Val Val Thr Ser Val Pro Ala Pro Gly Thr Trp Thr Ser Val
2495                2500                2505

Gly Ser Thr Thr Asp Leu Pro Ala Met Gly Phe Leu Lys Thr Ser
2510                2515                2520

Pro Ala Gly Glu Ala His Ser Leu Leu Ala Ser Thr Ile Glu Pro
2525                2530                2535

Ala Thr Ala Phe Thr Pro His Leu Ser Ala Ala Val Val Thr Gly
2540                2545                2550

Ser Ser Ala Thr Ser Glu Ala Ser Leu Leu Thr Thr Ser Glu Ser
2555                2560                2565

Lys Ala Ile His Ser Ser Pro Gln Thr Pro Thr Thr Pro Thr Ser
2570                2575                2580

Gly Ala Asn Trp Glu Thr Ser Ala Thr Pro Glu Ser Leu Leu Val
2585                2590                2595

Val Thr Glu Thr Ser Asp Thr Thr Leu Thr Ser Lys Ile Leu Val
2600                2605                2610

Thr Asp Thr Ile Leu Phe Ser Thr Val Ser Thr Pro Pro Ser Lys
2615                2620                2625

Phe Pro Ser Thr Gly Thr Leu Ser Gly Ala Ser Phe Pro Thr Leu
2630                2635                2640

Leu Pro Asp Thr Pro Ala Ile Pro Leu Thr Ala Thr Glu Pro Thr
2645                2650                2655

Ser Ser Leu Ala Thr Ser Phe Asp Ser Thr Pro Leu Val Thr Ile
2660                2665                2670

Ala Ser Asp Ser Leu Gly Thr Val Pro Glu Thr Thr Leu Thr Met
2675                2680                2685

Ser Glu Thr Ser Asn Gly Asp Ala Leu Val Leu Lys Thr Val Ser
2690                2695                2700

Asn Pro Asp Arg Ser Ile Pro Gly Ile Thr Ile Gln Gly Val Thr
2705                2710                2715

Glu Ser Pro Leu His Pro Ser Ser Thr Ser Pro Ser Lys Ile Val
2720                2725                2730
```

-continued

| | | | | | | | | | | |
|---|---|---|---|---|---|---|---|---|---|---|
|Ala|Pro|Arg|Asn|Thr|Thr|Tyr|Glu|Gly|Ser|Ile|Thr|Val|Ala|Leu|
| |2735| | | |2740| | | |2745| | | | | |
|Ser|Thr|Leu|Pro|Ala|Gly|Thr|Gly|Ser|Leu|Val|Phe|Ser|Gln|
| |2750| | | |2755| | | |2760| | | | | |
|Ser|Ser|Glu|Asn|Ser|Glu|Thr|Thr|Ala|Leu|Val|Asp|Ser|Ser|Ala|
| |2765| | | |2770| | | |2775| | | | | |
|Gly|Leu|Glu|Arg|Ala|Ser|Val|Met|Pro|Leu|Thr|Thr|Gly|Ser|Gln|
| |2780| | | |2785| | | |2790| | | | | |
|Gly|Met|Ala|Ser|Ser|Gly|Gly|Ile|Arg|Ser|Gly|Ser|Thr|His|Ser|
| |2795| | | |2800| | | |2805| | | | | |
|Thr|Gly|Thr|Lys|Thr|Phe|Ser|Ser|Leu|Pro|Leu|Thr|Met|Asn|Pro|
| |2810| | | |2815| | | |2820| | | | | |
|Gly|Glu|Val|Thr|Ala|Met|Ser|Glu|Ile|Thr|Thr|Asn|Arg|Leu|Thr|
| |2825| | | |2830| | | |2835| | | | | |
|Ala|Thr|Gln|Ser|Thr|Ala|Pro|Lys|Gly|Ile|Pro|Val|Lys|Pro|Thr|
| |2840| | | |2845| | | |2850| | | | | |
|Ser|Ala|Glu|Ser|Gly|Leu|Leu|Thr|Pro|Val|Ser|Ala|Ser|Ser|Ser|
| |2855| | | |2860| | | |2865| | | | | |
|Pro|Ser|Lys|Ala|Phe|Ala|Ser|Leu|Thr|Thr|Ala|Pro|Pro|Thr|Trp|
| |2870| | | |2875| | | |2880| | | | | |
|Gly|Ile|Pro|Gln|Ser|Thr|Leu|Thr|Phe|Glu|Phe|Ser|Glu|Val|Pro|
| |2885| | | |2890| | | |2895| | | | | |
|Ser|Leu|Asp|Thr|Lys|Ser|Ala|Ser|Leu|Pro|Thr|Pro|Gly|Gln|Ser|
| |2900| | | |2905| | | |2910| | | | | |
|Leu|Asn|Thr|Ile|Pro|Asp|Ser|Asp|Ala|Ser|Thr|Ala|Ser|Ser|Ser|
| |2915| | | |2920| | | |2925| | | | | |
|Leu|Ser|Lys|Ser|Pro|Glu|Lys|Asn|Pro|Arg|Ala|Arg|Met|Met|Thr|
| |2930| | | |2935| | | |2940| | | | | |
|Ser|Thr|Lys|Ala|Ile|Ser|Ala|Ser|Ser|Phe|Gln|Ser|Thr|Gly|Phe|
| |2945| | | |2950| | | |2955| | | | | |
|Thr|Glu|Thr|Pro|Glu|Gly|Ser|Ala|Ser|Pro|Ser|Met|Ala|Gly|His|
| |2960| | | |2965| | | |2970| | | | | |
|Glu|Pro|Arg|Val|Pro|Thr|Ser|Gly|Thr|Gly|Asp|Pro|Arg|Tyr|Ala|
| |2975| | | |2980| | | |2985| | | | | |
|Ser|Glu|Ser|Met|Ser|Tyr|Pro|Asp|Pro|Ser|Lys|Ala|Ser|Ser|Ala|
| |2990| | | |2995| | | |3000| | | | | |
|Met|Thr|Ser|Thr|Ser|Leu|Ala|Ser|Lys|Leu|Thr|Thr|Leu|Phe|Ser|
| |3005| | | |3010| | | |3015| | | | | |
|Thr|Gly|Gln|Ala|Ala|Arg|Ser|Gly|Ser|Ser|Ser|Pro|Ile|Ser|
| |3020| | | |3025| | | |3030| | | | | |
|Leu|Ser|Thr|Glu|Lys|Glu|Thr|Ser|Phe|Leu|Ser|Pro|Thr|Ala|Ser|
| |3035| | | |3040| | | |3045| | | | | |
|Thr|Ser|Arg|Lys|Thr|Ser|Leu|Phe|Leu|Gly|Pro|Ser|Met|Ala|Arg|
| |3050| | | |3055| | | |3060| | | | | |
|Gln|Pro|Asn|Ile|Leu|Val|His|Leu|Gln|Thr|Ser|Ala|Leu|Thr|Leu|
| |3065| | | |3070| | | |3075| | | | | |
|Ser|Pro|Thr|Ser|Thr|Leu|Asn|Met|Ser|Gln|Glu|Glu|Pro|Pro|Glu|
| |3080| | | |3085| | | |3090| | | | | |
|Leu|Thr|Ser|Ser|Gln|Thr|Ile|Ala|Glu|Glu|Glu|Gly|Thr|Thr|Ala|
| |3095| | | |3100| | | |3105| | | | | |
|Glu|Thr|Gln|Thr|Leu|Thr|Phe|Thr|Pro|Ser|Glu|Thr|Pro|Thr|Ser|
| |3110| | | |3115| | | |3120| | | | | |

-continued

```
Leu Leu Pro Val Ser Ser Pro Thr Glu Pro Thr Ala Arg Arg Lys
3125                3130                3135

Ser Ser Pro Glu Thr Trp Ala Ser Ser Ile Ser Val Pro Ala Lys
3140                3145                3150

Thr Ser Leu Val Glu Thr Thr Asp Gly Thr Leu Val Thr Thr Ile
3155                3160                3165

Lys Met Ser Ser Gln Ala Ala Gln Gly Asn Ser Thr Trp Pro Ala
3170                3175                3180

Pro Ala Glu Glu Thr Gly Ser Ser Pro Ala Gly Thr Ser Pro Gly
3185                3190                3195

Ser Pro Glu Met Ser Thr Thr Leu Lys Ile Met Ser Ser Lys Glu
3200                3205                3210

Pro Ser Ile Ser Pro Glu Ile Arg Ser Thr Val Arg Asn Ser Pro
3215                3220                3225

Trp Lys Thr Pro Glu Thr Thr Val Pro Met Glu Thr Thr Val Glu
3230                3235                3240

Pro Val Thr Leu Gln Ser Thr Ala Leu Gly Ser Gly Ser Thr Ser
3245                3250                3255

Ile Ser His Leu Pro Thr Gly Thr Thr Ser Pro Thr Lys Ser Pro
3260                3265                3270

Thr Glu Asn Met Leu Ala Thr Glu Arg Val Ser Leu Ser Pro Ser
3275                3280                3285

Pro Pro Glu Ala Trp Thr Asn Leu Tyr Ser Gly Thr Pro Gly Gly
3290                3295                3300

Thr Arg Gln Ser Leu Ala Thr Met Ser Ser Val Ser Leu Glu Ser
3305                3310                3315

Pro Thr Ala Arg Ser Ile Thr Gly Thr Gly Gln Gln Ser Ser Pro
3320                3325                3330

Glu Leu Val Ser Lys Thr Thr Gly Met Glu Phe Ser Met Trp His
3335                3340                3345

Gly Ser Thr Gly Gly Thr Thr Gly Asp Thr His Val Ser Leu Ser
3350                3355                3360

Thr Ser Ser Asn Ile Leu Glu Asp Pro Val Thr Ser Pro Asn Ser
3365                3370                3375

Val Ser Ser Leu Thr Asp Lys Ser Lys His Lys Thr Glu Thr Trp
3380                3385                3390

Val Ser Thr Thr Ala Ile Pro Ser Thr Val Leu Asn Asn Lys Ile
3395                3400                3405

Met Ala Ala Glu Gln Gln Thr Ser Arg Ser Val Asp Glu Ala Tyr
3410                3415                3420

Ser Ser Thr Ser Ser Trp Ser Asp Gln Thr Ser Gly Ser Asp Ile
3425                3430                3435

Thr Leu Gly Ala Ser Pro Asp Val Thr Asn Thr Leu Tyr Ile Thr
3440                3445                3450

Ser Thr Ala Gln Thr Thr Ser Leu Val Ser Leu Pro Ser Gly Asp
3455                3460                3465

Gln Gly Ile Thr Ser Leu Thr Asn Pro Ser Gly Gly Lys Thr Ser
3470                3475                3480

Ser Ala Ser Ser Val Thr Ser Pro Ser Ile Gly Leu Glu Thr Leu
3485                3490                3495

Arg Ala Asn Val Ser Ala Val Lys Ser Asp Ile Ala Pro Thr Ala
3500                3505                3510
```

```
Gly His Leu Ser Gln Thr Ser Ser Pro Ala Glu Val Ser Ile Leu
3515                3520                3525

Asp Val Thr Thr Ala Pro Pro Gly Ile Ser Thr Thr Ile Thr
3530                3535                3540

Thr Met Gly Thr Asn Ser Ile Ser Thr Thr Pro Asn Pro Glu
3545                3550                3555

Val Gly Met Ser Thr Met Asp Ser Thr Pro Ala Thr Glu Arg Arg
3560                3565                3570

Thr Thr Ser Thr Glu His Pro Ser Thr Trp Ser Ser Thr Ala Ala
3575                3580                3585

Ser Asp Ser Trp Thr Val Thr Asp Met Thr Ser Asn Leu Lys Val
3590                3595                3600

Ala Arg Ser Pro Gly Thr Ile Ser Thr Met His Thr Thr Ser Phe
3605                3610                3615

Leu Ala Ser Ser Thr Glu Leu Asp Ser Met Ser Thr Pro His Gly
3620                3625                3630

Arg Ile Thr Val Ile Gly Thr Ser Leu Val Thr Pro Ser Ser Asp
3635                3640                3645

Ala Ser Ala Val Lys Thr Glu Thr Ser Thr Ser Glu Arg Thr Leu
3650                3655                3660

Ser Pro Ser Asp Thr Thr Ala Ser Thr Pro Ile Ser Thr Phe Ser
3665                3670                3675

Arg Val Gln Arg Met Ser Ile Ser Val Pro Asp Ile Leu Ser Thr
3680                3685                3690

Ser Trp Thr Pro Ser Ser Thr Glu Ala Glu Asp Val Pro Val Ser
3695                3700                3705

Met Val Ser Thr Asp His Ala Ser Thr Lys Thr Asp Pro Asn Thr
3710                3715                3720

Pro Leu Ser Thr Phe Leu Phe Asp Ser Leu Ser Thr Leu Asp Trp
3725                3730                3735

Asp Thr Gly Arg Ser Leu Ser Ser Ala Thr Ala Thr Thr Ser Ala
3740                3745                3750

Pro Gln Gly Ala Thr Thr Pro Gln Glu Leu Thr Leu Glu Thr Met
3755                3760                3765

Ile Ser Pro Ala Thr Ser Gln Leu Pro Phe Ser Ile Gly His Ile
3770                3775                3780

Thr Ser Ala Val Thr Pro Ala Ala Met Ala Arg Ser Ser Gly Val
3785                3790                3795

Thr Phe Ser Arg Pro Asp Pro Thr Ser Lys Lys Ala Glu Gln Thr
3800                3805                3810

Ser Thr Gln Leu Pro Thr Thr Thr Ser Ala His Pro Gly Gln Val
3815                3820                3825

Pro Arg Ser Ala Ala Thr Thr Leu Asp Val Ile Pro His Thr Ala
3830                3835                3840

Lys Thr Pro Asp Ala Thr Phe Gln Arg Gln Gly Gln Thr Ala Leu
3845                3850                3855

Thr Thr Glu Ala Arg Ala Thr Ser Asp Ser Trp Asn Glu Lys Glu
3860                3865                3870

Lys Ser Thr Pro Ser Ala Pro Trp Ile Thr Glu Met Met Asn Ser
3875                3880                3885

Val Ser Glu Asp Thr Ile Lys Glu Val Thr Ser Ser Ser Ser Val
3890                3895                3900
```

```
Leu Arg Thr Leu Asn Thr Leu Asp Ile Asn Leu Glu Ser Gly Thr
    3905                3910                3915

Thr Ser Ser Pro Ser Trp Lys Ser Ser Pro Tyr Glu Arg Ile Ala
    3920                3925                3930

Pro Ser Glu Ser Thr Thr Asp Lys Glu Ala Ile His Pro Ser Thr
    3935                3940                3945

Asn Thr Val Glu Thr Thr Gly Trp Val Thr Ser Glu His Ala
    3950                3955                3960

Ser His Ser Thr Ile Pro Ala His Ser Ala Ser Lys Leu Thr
    3965                3970                3975

Ser Pro Val Val Thr Thr Ser Thr Arg Glu Gln Ala Ile Val Ser
    3980                3985                3990

Met Ser Thr Thr Thr Trp Pro Glu Ser Thr Arg Ala Arg Thr Glu
    3995                4000                4005

Pro Asn Ser Phe Leu Thr Ile Glu Leu Arg Asp Val Ser Pro Tyr
    4010                4015                4020

Met Asp Thr Ser Ser Thr Thr Gln Thr Ser Ile Ile Ser Ser Pro
    4025                4030                4035

Gly Ser Thr Ala Ile Thr Lys Gly Pro Arg Thr Glu Ile Thr Ser
    4040                4045                4050

Ser Lys Arg Ile Ser Ser Ser Phe Leu Ala Gln Ser Met Arg Ser
    4055                4060                4065

Ser Asp Ser Pro Ser Glu Ala Ile Thr Arg Leu Ser Asn Phe Pro
    4070                4075                4080

Ala Met Thr Glu Ser Gly Gly Met Ile Leu Ala Met Gln Thr Ser
    4085                4090                4095

Pro Pro Gly Ala Thr Ser Leu Ser Ala Pro Thr Leu Asp Thr Ser
    4100                4105                4110

Ala Thr Ala Ser Trp Thr Gly Thr Pro Leu Ala Thr Thr Gln Arg
    4115                4120                4125

Phe Thr Tyr Ser Glu Lys Thr Thr Leu Phe Ser Lys Gly Pro Glu
    4130                4135                4140

Asp Thr Ser Gln Pro Ser Pro Pro Ser Val Glu Glu Thr Ser Ser
    4145                4150                4155

Ser Ser Ser Leu Val Pro Ile His Ala Thr Thr Ser Pro Ser Asn
    4160                4165                4170

Ile Leu Leu Thr Ser Gln Gly His Ser Pro Ser Ser Thr Pro Pro
    4175                4180                4185

Val Thr Ser Val Phe Leu Ser Glu Thr Ser Gly Leu Gly Lys Thr
    4190                4195                4200

Thr Asp Met Ser Arg Ile Ser Leu Glu Pro Gly Thr Ser Leu Pro
    4205                4210                4215

Pro Asn Leu Ser Ser Thr Ala Gly Glu Ala Leu Ser Thr Tyr Glu
    4220                4225                4230

Ala Ser Arg Asp Thr Lys Ala Ile His His Ser Ala Asp Thr Ala
    4235                4240                4245

Val Thr Asn Met Glu Ala Thr Ser Ser Glu Tyr Ser Pro Ile Pro
    4250                4255                4260

Gly His Thr Lys Pro Ser Lys Ala Thr Ser Pro Leu Val Thr Ser
    4265                4270                4275

His Ile Met Gly Asp Ile Thr Ser Ser Thr Ser Val Phe Gly Ser
    4280                4285                4290
```

```
Ser Glu Thr Thr Glu Ile Glu Thr Val Ser Ser Val Asn Gln Gly
4295                4300                4305

Leu Gln Glu Arg Ser Thr Ser Gln Val Ala Ser Ser Ala Thr Glu
4310                4315                4320

Thr Ser Thr Val Ile Thr His Val Ser Ser Gly Asp Ala Thr Thr
4325                4330                4335

His Val Thr Lys Thr Gln Ala Thr Phe Ser Ser Gly Thr Ser Ile
4340                4345                4350

Ser Ser Pro His Gln Phe Ile Thr Ser Thr Asn Thr Phe Thr Asp
4355                4360                4365

Val Ser Thr Asn Pro Ser Thr Ser Leu Ile Met Thr Glu Ser Ser
4370                4375                4380

Gly Val Thr Ile Thr Thr Gln Thr Gly Pro Thr Gly Ala Ala Thr
4385                4390                4395

Gln Gly Pro Tyr Leu Leu Asp Thr Ser Thr Met Pro Tyr Leu Thr
4400                4405                4410

Glu Thr Pro Leu Ala Val Thr Pro Asp Phe Met Gln Ser Glu Lys
4415                4420                4425

Thr Thr Leu Ile Ser Lys Gly Pro Lys Asp Val Ser Trp Thr Ser
4430                4435                4440

Pro Pro Ser Val Ala Glu Thr Ser Tyr Pro Ser Ser Leu Thr Pro
4445                4450                4455

Phe Leu Val Thr Thr Ile Pro Pro Ala Thr Ser Thr Leu Gln Gly
4460                4465                4470

Gln His Thr Ser Ser Pro Val Ser Ala Thr Ser Val Leu Thr Ser
4475                4480                4485

Gly Leu Val Lys Thr Thr Asp Met Leu Asn Thr Ser Met Glu Pro
4490                4495                4500

Val Thr Asn Ser Pro Gln Asn Leu Asn Asn Pro Ser Asn Glu Ile
4505                4510                4515

Leu Ala Thr Leu Ala Ala Thr Thr Asp Ile Glu Thr Ile His Pro
4520                4525                4530

Ser Ile Asn Lys Ala Val Thr Asn Met Gly Thr Ala Ser Ser Ala
4535                4540                4545

His Val Leu His Ser Thr Leu Pro Val Ser Ser Glu Pro Ser Thr
4550                4555                4560

Ala Thr Ser Pro Met Val Pro Ala Ser Ser Met Gly Asp Ala Leu
4565                4570                4575

Ala Ser Ile Ser Ile Pro Gly Ser Glu Thr Thr Asp Ile Glu Gly
4580                4585                4590

Glu Pro Thr Ser Ser Leu Thr Ala Gly Arg Lys Glu Asn Ser Thr
4595                4600                4605

Leu Gln Glu Met Asn Ser Thr Thr Glu Ser Asn Ile Ile Leu Ser
4610                4615                4620

Asn Val Ser Val Gly Ala Ile Thr Glu Ala Thr Lys Met Glu Val
4625                4630                4635

Pro Ser Phe Asp Ala Thr Phe Ile Pro Thr Pro Ala Gln Ser Thr
4640                4645                4650

Lys Phe Pro Asp Ile Phe Ser Val Ala Ser Ser Arg Leu Ser Asn
4655                4660                4665

Ser Pro Pro Met Thr Ile Ser Thr His Met Thr Thr Thr Gln Thr
4670                4675                4680
```

-continued

Gly Ser Ser Gly Ala Thr Ser Lys Ile Pro Leu Ala Leu Asp Thr
4685                4690                4695

Ser Thr Leu Glu Thr Ser Ala Gly Thr Pro Ser Val Val Thr Glu
4700                4705                4710

Gly Phe Ala His Ser Lys Ile Thr Thr Ala Met Asn Asn Asp Val
4715                4720                4725

Lys Asp Val Ser Gln Thr Asn Pro Pro Phe Gln Asp Glu Ala Ser
4730                4735                4740

Ser Pro Ser Ser Gln Ala Pro Val Leu Val Thr Thr Leu Pro Ser
4745                4750                4755

Ser Val Ala Phe Thr Pro Gln Trp His Ser Thr Ser Ser Pro Val
4760                4765                4770

Ser Met Ser Ser Val Leu Thr Ser Ser Leu Val Lys Thr Ala Gly
4775                4780                4785

Lys Val Asp Thr Ser Leu Glu Thr Val Thr Ser Ser Pro Gln Ser
4790                4795                4800

Met Ser Asn Thr Leu Asp Asp Ile Ser Val Thr Ser Ala Ala Thr
4805                4810                4815

Thr Asp Ile Glu Thr Thr His Pro Ser Ile Asn Thr Val Val Thr
4820                4825                4830

Asn Val Gly Thr Thr Gly Ser Ala Phe Glu Ser His Ser Thr Val
4835                4840                4845

Ser Ala Tyr Pro Glu Pro Ser Lys Val Thr Ser Pro Asn Val Thr
4850                4855                4860

Thr Ser Thr Met Glu Asp Thr Thr Ile Ser Arg Ser Ile Pro Lys
4865                4870                4875

Ser Ser Lys Thr Thr Arg Thr Glu Thr Glu Thr Thr Ser Ser Leu
4880                4885                4890

Thr Pro Lys Leu Arg Glu Thr Ser Ile Ser Gln Glu Ile Thr Ser
4895                4900                4905

Ser Thr Glu Thr Ser Thr Val Pro Tyr Lys Glu Leu Thr Gly Ala
4910                4915                4920

Thr Thr Glu Val Ser Arg Thr Asp Val Thr Ser Ser Ser Ser Thr
4925                4930                4935

Ser Phe Pro Gly Pro Asp Gln Ser Thr Val Ser Leu Asp Ile Ser
4940                4945                4950

Thr Glu Thr Asn Thr Arg Leu Ser Thr Ser Pro Ile Met Thr Glu
4955                4960                4965

Ser Ala Glu Ile Thr Ile Thr Thr Gln Thr Gly Pro His Gly Ala
4970                4975                4980

Thr Ser Gln Asp Thr Phe Thr Met Asp Pro Ser Asn Thr Thr Pro
4985                4990                4995

Gln Ala Gly Ile His Ser Ala Met Thr His Gly Phe Ser Gln Leu
5000                5005                5010

Asp Val Thr Thr Leu Met Ser Arg Ile Pro Gln Asp Val Ser Trp
5015                5020                5025

Thr Ser Pro Pro Ser Val Asp Lys Thr Ser Ser Pro Ser Ser Phe
5030                5035                5040

Leu Ser Ser Pro Ala Met Thr Thr Pro Ser Leu Ile Ser Ser Thr
5045                5050                5055

Leu Pro Glu Asp Lys Leu Ser Ser Pro Met Thr Ser Leu Leu Thr
5060                5065                5070

```
Ser Gly Leu Val Lys Ile Thr Asp Ile Leu Arg Thr Arg Leu Glu
    5075                5080                5085

Pro Val Thr Ser Ser Leu Pro Asn Phe Ser Thr Ser Asp Lys
    5090                5095                5100

Ile Leu Ala Thr Ser Lys Asp Ser Lys Asp Thr Lys Glu Ile Phe
    5105                5110                5115

Pro Ser Ile Asn Thr Glu Glu Thr Asn Val Lys Ala Asn Asn Ser
    5120                5125                5130

Gly His Glu Ser His Ser Pro Ala Leu Ala Asp Ser Glu Thr Pro
    5135                5140                5145

Lys Ala Thr Thr Gln Met Val Ile Thr Thr Thr Val Gly Asp Pro
    5150                5155                5160

Ala Pro Ser Thr Ser Met Pro Val His Gly Ser Ser Glu Thr Thr
    5165                5170                5175

Asn Ile Lys Arg Glu Pro Thr Tyr Phe Leu Thr Pro Arg Leu Arg
    5180                5185                5190

Glu Thr Ser Thr Ser Gln Glu Ser Ser Phe Pro Thr Asp Thr Ser
    5195                5200                5205

Phe Leu Leu Ser Lys Val Pro Thr Gly Thr Ile Thr Glu Val Ser
    5210                5215                5220

Ser Thr Gly Val Asn Ser Ser Ser Lys Ile Ser Thr Pro Asp His
    5225                5230                5235

Asp Lys Ser Thr Val Pro Pro Asp Thr Phe Thr Gly Glu Ile Pro
    5240                5245                5250

Arg Val Phe Thr Ser Ser Ile Lys Thr Lys Ser Ala Glu Met Thr
    5255                5260                5265

Ile Thr Thr Gln Ala Ser Pro Pro Glu Ser Ala Ser His Ser Thr
    5270                5275                5280

Leu Pro Leu Asp Thr Ser Thr Leu Ser Gln Gly Gly Thr His
    5285                5290                5295

Ser Thr Val Thr Gln Gly Phe Pro Tyr Ser Glu Val Thr Thr Leu
    5300                5305                5310

Met Gly Met Gly Pro Gly Asn Val Ser Trp Met Thr Thr Pro Pro
    5315                5320                5325

Val Glu Glu Thr Ser Ser Val Ser Ser Leu Met Ser Ser Pro Ala
    5330                5335                5340

Met Thr Ser Pro Ser Pro Val Ser Ser Thr Ser Pro Gln Ser Ile
    5345                5350                5355

Pro Ser Ser Pro Leu Pro Val Thr Ala Leu Pro Thr Ser Val Leu
    5360                5365                5370

Val Thr Thr Thr Asp Val Leu Gly Thr Thr Ser Pro Glu Ser Val
    5375                5380                5385

Thr Ser Ser Pro Pro Asn Leu Ser Ser Ile Thr His Glu Arg Pro
    5390                5395                5400

Ala Thr Tyr Lys Asp Thr Ala His Thr Glu Ala Ala Met His His
    5405                5410                5415

Ser Thr Asn Thr Ala Val Thr Asn Val Gly Thr Ser Gly Ser Gly
    5420                5425                5430

His Lys Ser Gln Ser Ser Val Leu Ala Asp Ser Glu Thr Ser Lys
    5435                5440                5445

Ala Thr Pro Leu Met Ser Thr Thr Ser Thr Leu Gly Asp Thr Ser
    5450                5455                5460
```

Val Ser Thr Ser Thr Pro Asn Ile Ser Gln Thr Asn Gln Ile Gln
5465                 5470                5475

Thr Glu Pro Thr Ala Ser Leu Ser Pro Arg Leu Arg Glu Ser Ser
5480                5485                 5490

Thr Ser Glu Lys Thr Ser Ser Thr Thr Glu Thr Asn Thr Ala Phe
5495                5500                 5505

Ser Tyr Val Pro Thr Gly Ala Ile Thr Gln Ala Ser Arg Thr Glu
5510                5515                 5520

Ile Ser Ser Ser Arg Thr Ser Ile Ser Asp Leu Asp Arg Pro Thr
5525                5530                 5535

Ile Ala Pro Asp Ile Ser Thr Gly Met Ile Thr Arg Leu Phe Thr
5540                5545                 5550

Ser Pro Ile Met Thr Lys Ser Ala Glu Met Thr Val Thr Thr Gln
5555                5560                 5565

Thr Thr Thr Pro Gly Ala Thr Ser Gln Gly Ile Leu Pro Trp Asp
5570                5575                 5580

Thr Ser Thr Thr Leu Phe Gln Gly Gly Thr His Ser Thr Val Ser
5585                5590                 5595

Gln Gly Phe Pro His Ser Glu Ile Thr Thr Leu Arg Ser Arg Thr
5600                5605                 5610

Pro Gly Asp Val Ser Trp Met Thr Thr Pro Pro Val Glu Glu Thr
5615                5620                 5625

Ser Ser Gly Phe Ser Leu Met Ser Pro Ser Met Thr Ser Pro Ser
5630                5635                 5640

Pro Val Ser Ser Thr Ser Pro Glu Ser Ile Pro Ser Ser Pro Leu
5645                5650                 5655

Pro Val Thr Ala Leu Leu Thr Ser Val Leu Val Thr Thr Thr Asn
5660                5665                 5670

Val Leu Gly Thr Thr Ser Pro Glu Pro Val Thr Ser Ser Pro Pro
5675                5680                 5685

Asn Leu Ser Ser Pro Thr Gln Glu Arg Leu Thr Thr Tyr Lys Asp
5690                5695                 5700

Thr Ala His Thr Glu Ala Met His Ala Ser Met His Thr Asn Thr
5705                5710                 5715

Ala Val Ala Asn Val Gly Thr Ser Ile Ser Gly His Glu Ser Gln
5720                5725                 5730

Ser Ser Val Pro Ala Asp Ser His Thr Ser Lys Ala Thr Ser Pro
5735                5740                 5745

Met Gly Ile Thr Phe Ala Met Gly Asp Thr Ser Val Ser Thr Ser
5750                5755                 5760

Thr Pro Ala Phe Phe Glu Thr Arg Ile Gln Thr Glu Ser Thr Ser
5765                5770                 5775

Ser Leu Ile Pro Gly Leu Arg Asp Thr Arg Thr Ser Glu Glu Ile
5780                5785                 5790

Asn Thr Val Thr Glu Thr Ser Thr Val Leu Ser Glu Val Pro Thr
5795                5800                 5805

Thr Thr Thr Thr Glu Val Ser Arg Thr Glu Val Ile Thr Ser Ser
5810                5815                 5820

Arg Thr Thr Ile Ser Gly Pro Asp His Ser Lys Met Ser Pro Tyr
5825                5830                 5835

Ile Ser Thr Glu Thr Ile Thr Arg Leu Ser Thr Phe Pro Phe Val
5840                5845                 5850

```
Thr Gly Ser Thr Glu Met Ala Ile Thr Asn Gln Thr Gly Pro Ile
    5855            5860            5865

Gly Thr Ile Ser Gln Ala Thr Leu Thr Leu Asp Thr Ser Ser Thr
    5870            5875            5880

Ala Ser Trp Glu Gly Thr His Ser Pro Val Thr Gln Arg Phe Pro
    5885            5890            5895

His Ser Glu Glu Thr Thr Thr Met Ser Arg Ser Thr Lys Gly Val
    5900            5905            5910

Ser Trp Gln Ser Pro Pro Ser Val Glu Glu Thr Ser Ser Pro Ser
    5915            5920            5925

Ser Pro Val Pro Leu Pro Ala Ile Thr Ser His Ser Ser Leu Tyr
    5930            5935            5940

Ser Ala Val Ser Gly Ser Ser Pro Thr Ser Ala Leu Pro Val Thr
    5945            5950            5955

Ser Leu Leu Thr Ser Gly Arg Arg Lys Thr Ile Asp Met Leu Asp
    5960            5965            5970

Thr His Ser Glu Leu Val Thr Ser Ser Leu Pro Ser Ala Ser Ser
    5975            5980            5985

Phe Ser Gly Glu Ile Leu Thr Ser Glu Ala Ser Thr Asn Thr Glu
    5990            5995            6000

Thr Ile His Phe Ser Glu Asn Thr Ala Glu Thr Asn Met Gly Thr
    6005            6010            6015

Thr Asn Ser Met His Lys Leu His Ser Ser Val Ser Ile His Ser
    6020            6025            6030

Gln Pro Ser Gly His Thr Pro Pro Lys Val Thr Gly Ser Met Met
    6035            6040            6045

Glu Asp Ala Ile Val Ser Thr Ser Thr Pro Gly Ser Pro Glu Thr
    6050            6055            6060

Lys Asn Val Asp Arg Asp Ser Thr Ser Pro Leu Thr Pro Glu Leu
    6065            6070            6075

Lys Glu Asp Ser Thr Ala Leu Val Met Asn Ser Thr Thr Glu Ser
    6080            6085            6090

Asn Thr Val Phe Ser Ser Val Ser Leu Asp Ala Ala Thr Glu Val
    6095            6100            6105

Ser Arg Ala Glu Val Thr Tyr Tyr Asp Pro Thr Phe Met Pro Ala
    6110            6115            6120

Ser Ala Gln Ser Thr Lys Ser Pro Asp Ile Ser Pro Glu Ala Ser
    6125            6130            6135

Ser Ser His Ser Asn Ser Pro Pro Leu Thr Ile Ser Thr His Lys
    6140            6145            6150

Thr Ile Ala Thr Gln Thr Gly Pro Ser Gly Val Thr Ser Leu Gly
    6155            6160            6165

Gln Leu Thr Leu Asp Thr Ser Thr Ile Ala Thr Ser Ala Gly Thr
    6170            6175            6180

Pro Ser Ala Arg Thr Gln Asp Phe Val Asp Ser Glu Thr Thr Ser
    6185            6190            6195

Val Met Asn Asn Asp Leu Asn Asp Val Leu Lys Thr Ser Pro Phe
    6200            6205            6210

Ser Ala Glu Glu Ala Asn Ser Leu Ser Ser Gln Ala Pro Leu Leu
    6215            6220            6225

Val Thr Thr Ser Pro Ser Pro Val Thr Ser Thr Leu Gln Glu His
    6230            6235            6240
```

-continued

Ser Thr Ser Ser Leu Val Ser Val Thr Ser Val Pro Thr Pro Thr
6245                 6250                 6255

Leu Ala Lys Ile Thr Asp Met Asp Thr Asn Leu Glu Pro Val Thr
6260                 6265                 6270

Arg Ser Pro Gln Asn Leu Arg Asn Thr Leu Ala Thr Ser Glu Ala
6275                 6280                 6285

Thr Thr Asp Thr His Thr Met His Pro Ser Ile Asn Thr Ala Val
6290                 6295                 6300

Ala Asn Val Gly Thr Thr Ser Ser Pro Asn Glu Phe Tyr Phe Thr
6305                 6310                 6315

Val Ser Pro Asp Ser Asp Pro Tyr Lys Ala Thr Ser Ala Val Val
6320                 6325                 6330

Ile Thr Ser Thr Ser Gly Asp Ser Ile Val Ser Thr Ser Met Pro
6335                 6340                 6345

Arg Ser Ser Ala Met Lys Lys Ile Glu Ser Glu Thr Thr Phe Ser
6350                 6355                 6360

Leu Ile Phe Arg Leu Arg Glu Thr Ser Thr Ser Gln Lys Ile Gly
6365                 6370                 6375

Ser Ser Ser Asp Thr Ser Thr Val Phe Asp Lys Ala Phe Thr Ala
6380                 6385                 6390

Ala Thr Thr Glu Val Ser Arg Thr Glu Leu Thr Ser Ser Ser Arg
6395                 6400                 6405

Thr Ser Ile Gln Gly Thr Glu Lys Pro Thr Met Ser Pro Asp Thr
6410                 6415                 6420

Ser Thr Arg Ser Val Thr Met Leu Ser Thr Phe Ala Gly Leu Thr
6425                 6430                 6435

Lys Ser Glu Glu Arg Thr Ile Ala Thr Gln Thr Gly Pro His Arg
6440                 6445                 6450

Ala Thr Ser Gln Gly Thr Leu Thr Trp Asp Thr Ser Ile Thr Thr
6455                 6460                 6465

Ser Gln Ala Gly Thr His Ser Ala Met Thr His Gly Phe Ser Gln
6470                 6475                 6480

Leu Asp Leu Ser Thr Leu Thr Ser Arg Val Pro Glu Tyr Ile Ser
6485                 6490                 6495

Gly Thr Ser Pro Pro Ser Val Glu Lys Thr Ser Ser Ser Ser Ser
6500                 6505                 6510

Leu Leu Ser Leu Pro Ala Ile Thr Ser Pro Ser Pro Val Pro Thr
6515                 6520                 6525

Thr Leu Pro Glu Ser Arg Pro Ser Ser Pro Val His Leu Thr Ser
6530                 6535                 6540

Leu Pro Thr Ser Gly Leu Val Lys Thr Thr Asp Met Leu Ala Ser
6545                 6550                 6555

Val Ala Ser Leu Pro Pro Asn Leu Gly Ser Thr Ser His Lys Ile
6560                 6565                 6570

Pro Thr Thr Ser Glu Asp Ile Lys Asp Thr Glu Lys Met Tyr Pro
6575                 6580                 6585

Ser Thr Asn Ile Ala Val Thr Asn Val Gly Thr Thr Ser Glu
6590                 6595                 6600

Lys Glu Ser Tyr Ser Ser Val Pro Ala Tyr Ser Glu Pro Pro Lys
6605                 6610                 6615

Val Thr Ser Pro Met Val Thr Ser Phe Asn Ile Arg Asp Thr Ile
6620                 6625                 6630

```
Val Ser Thr Ser Met Pro Gly Ser Ser Glu Ile Thr Arg Ile Glu
6635                6640                6645

Met Glu Ser Thr Phe Ser Leu Ala His Gly Leu Lys Gly Thr Ser
6650                6655                6660

Thr Ser Gln Asp Pro Ile Val Ser Thr Glu Lys Ser Ala Val Leu
6665                6670                6675

His Lys Leu Thr Thr Gly Ala Thr Glu Thr Ser Arg Thr Glu Val
6680                6685                6690

Ala Ser Ser Arg Arg Thr Ser Ile Pro Gly Pro Asp His Ser Thr
6695                6700                6705

Glu Ser Pro Asp Ile Ser Thr Glu Val Ile Pro Ser Leu Pro Ile
6710                6715                6720

Ser Leu Gly Ile Thr Glu Ser Ser Asn Met Thr Ile Ile Thr Arg
6725                6730                6735

Thr Gly Pro Pro Leu Gly Ser Thr Ser Gln Gly Thr Phe Thr Leu
6740                6745                6750

Asp Thr Pro Thr Thr Ser Ser Arg Ala Gly Thr His Ser Met Ala
6755                6760                6765

Thr Gln Glu Phe Pro His Ser Glu Met Thr Thr Val Met Asn Lys
6770                6775                6780

Asp Pro Glu Ile Leu Ser Trp Thr Ile Pro Pro Ser Ile Glu Lys
6785                6790                6795

Thr Ser Phe Ser Ser Ser Leu Met Pro Ser Pro Ala Met Thr Ser
6800                6805                6810

Pro Pro Val Ser Ser Thr Leu Pro Lys Thr Ile His Thr Thr Pro
6815                6820                6825

Ser Pro Met Thr Ser Leu Leu Thr Pro Ser Leu Val Met Thr Thr
6830                6835                6840

Asp Thr Leu Gly Thr Ser Pro Glu Pro Thr Thr Ser Ser Pro Pro
6845                6850                6855

Asn Leu Ser Ser Thr Ser His Glu Ile Leu Thr Thr Asp Glu Asp
6860                6865                6870

Thr Thr Ala Ile Glu Ala Met His Pro Ser Thr Ser Thr Ala Ala
6875                6880                6885

Thr Asn Val Glu Thr Thr Ser Ser Gly His Gly Ser Gln Ser Ser
6890                6895                6900

Val Leu Ala Asp Ser Glu Lys Thr Lys Ala Thr Ala Pro Met Asp
6905                6910                6915

Thr Thr Ser Thr Met Gly His Thr Thr Val Ser Thr Ser Met Ser
6920                6925                6930

Val Ser Ser Glu Thr Thr Lys Ile Lys Arg Glu Ser Thr Tyr Ser
6935                6940                6945

Leu Thr Pro Gly Leu Arg Glu Thr Ser Ile Ser Gln Asn Ala Ser
6950                6955                6960

Phe Ser Thr Asp Thr Ser Ile Val Leu Ser Glu Val Pro Thr Gly
6965                6970                6975

Thr Thr Ala Glu Val Ser Arg Thr Glu Val Thr Ser Ser Gly Arg
6980                6985                6990

Thr Ser Ile Pro Gly Pro Ser Gln Ser Thr Val Leu Pro Glu Ile
6995                7000                7005

Ser Thr Arg Thr Met Thr Arg Leu Phe Ala Ser Pro Thr Met Thr
7010                7015                7020
```

```
Glu Ser Ala Glu Met Thr Ile Pro Thr Gln Thr Gly Pro Ser Gly
    7025                7030                7035

Ser Thr Ser Gln Asp Thr Leu Thr Leu Asp Thr Ser Thr Thr Lys
    7040                7045                7050

Ser Gln Ala Lys Thr His Ser Thr Leu Thr Gln Arg Phe Pro His
    7055                7060                7065

Ser Glu Met Thr Thr Leu Met Ser Arg Gly Pro Gly Asp Met Ser
    7070                7075                7080

Trp Gln Ser Ser Pro Ser Leu Glu Asn Pro Ser Ser Leu Pro Ser
    7085                7090                7095

Leu Leu Ser Leu Pro Ala Thr Thr Ser Pro Pro Pro Ile Ser Ser
    7100                7105                7110

Thr Leu Pro Val Thr Ile Ser Ser Ser Pro Leu Pro Val Thr Ser
    7115                7120                7125

Leu Leu Thr Ser Ser Pro Val Thr Thr Thr Asp Met Leu His Thr
    7130                7135                7140

Ser Pro Glu Leu Val Thr Ser Ser Pro Pro Lys Leu Ser His Thr
    7145                7150                7155

Ser Asp Glu Arg Leu Thr Thr Gly Lys Asp Thr Thr Asn Thr Glu
    7160                7165                7170

Ala Val His Pro Ser Thr Asn Thr Ala Ala Ser Asn Val Glu Ile
    7175                7180                7185

Pro Ser Ser Gly His Glu Ser Pro Ser Ser Ala Leu Ala Asp Ser
    7190                7195                7200

Glu Thr Ser Lys Ala Thr Ser Pro Met Phe Ile Thr Ser Thr Gln
    7205                7210                7215

Glu Asp Thr Thr Val Ala Ile Ser Thr Pro His Phe Leu Glu Thr
    7220                7225                7230

Ser Arg Ile Gln Lys Glu Ser Ile Ser Ser Leu Ser Pro Lys Leu
    7235                7240                7245

Arg Glu Thr Gly Ser Ser Val Glu Thr Ser Ser Ala Ile Glu Thr
    7250                7255                7260

Ser Ala Val Leu Ser Glu Val Ser Ile Gly Ala Thr Thr Glu Ile
    7265                7270                7275

Ser Arg Thr Glu Val Thr Ser Ser Ser Arg Thr Ser Ile Ser Gly
    7280                7285                7290

Ser Ala Glu Ser Thr Met Leu Pro Glu Ile Ser Thr Thr Arg Lys
    7295                7300                7305

Ile Ile Lys Phe Pro Thr Ser Pro Ile Leu Ala Glu Ser Ser Glu
    7310                7315                7320

Met Thr Ile Lys Thr Gln Thr Ser Pro Pro Gly Ser Thr Ser Glu
    7325                7330                7335

Ser Thr Phe Thr Leu Asp Thr Ser Thr Thr Pro Ser Leu Val Ile
    7340                7345                7350

Thr His Ser Thr Met Thr Gln Arg Leu Pro His Ser Glu Ile Thr
    7355                7360                7365

Thr Leu Val Ser Arg Gly Ala Gly Asp Val Pro Arg Pro Ser Ser
    7370                7375                7380

Leu Pro Val Glu Glu Thr Ser Pro Pro Ser Ser Gln Leu Ser Leu
    7385                7390                7395

Ser Ala Met Ile Ser Pro Ser Pro Val Ser Ser Thr Leu Pro Ala
    7400                7405                7410
```

```
Ser Ser His Ser Ser Ser Ala Ser Val Thr Ser Leu Leu Thr Pro
    7415            7420            7425

Gly Gln Val Lys Thr Thr Glu Val Leu Asp Ala Ser Ala Glu Pro
7430            7435            7440

Glu Thr Ser Ser Pro Pro Ser Leu Ser Ser Thr Ser Val Glu Ile
7445            7450            7455

Leu Ala Thr Ser Glu Val Thr Thr Asp Thr Glu Lys Ile His Pro
7460            7465            7470

Phe Ser Asn Thr Ala Val Thr Lys Val Gly Thr Ser Ser Ser Gly
7475            7480            7485

His Glu Ser Pro Ser Ser Val Leu Pro Asp Ser Glu Thr Thr Lys
7490            7495            7500

Ala Thr Ser Ala Met Gly Thr Ile Ser Ile Met Gly Asp Thr Ser
7505            7510            7515

Val Ser Thr Leu Thr Pro Ala Leu Ser Asn Thr Arg Lys Ile Gln
7520            7525            7530

Ser Glu Pro Ala Ser Ser Leu Thr Thr Arg Leu Arg Glu Thr Ser
7535            7540            7545

Thr Ser Glu Glu Thr Ser Leu Ala Thr Glu Ala Asn Thr Val Leu
7550            7555            7560

Ser Lys Val Ser Thr Gly Ala Thr Thr Glu Val Ser Arg Thr Glu
7565            7570            7575

Ala Ile Ser Phe Ser Arg Thr Ser Met Ser Gly Pro Glu Gln Ser
7580            7585            7590

Thr Met Ser Gln Asp Ile Ser Ile Gly Thr Ile Pro Arg Ile Ser
7595            7600            7605

Ala Ser Ser Val Leu Thr Glu Ser Ala Lys Met Thr Ile Thr Thr
7610            7615            7620

Gln Thr Gly Pro Ser Glu Ser Thr Leu Glu Ser Thr Leu Asn Leu
7625            7630            7635

Asn Thr Ala Thr Thr Pro Ser Trp Val Glu Thr His Ser Ile Val
7640            7645            7650

Ile Gln Gly Phe Pro His Pro Glu Met Thr Thr Ser Met Gly Arg
7655            7660            7665

Gly Pro Gly Gly Val Ser Trp Pro Ser Pro Phe Val Lys Glu
7670            7675            7680

Thr Ser Pro Pro Ser Ser Pro Leu Ser Leu Pro Ala Val Thr Ser
7685            7690            7695

Pro His Pro Val Ser Thr Thr Phe Leu Ala His Ile Pro Pro Ser
7700            7705            7710

Pro Leu Pro Val Thr Ser Leu Leu Thr Ser Gly Pro Ala Thr Thr
7715            7720            7725

Thr Asp Ile Leu Gly Thr Ser Thr Glu Pro Gly Thr Ser Ser Ser
7730            7735            7740

Ser Ser Leu Ser Thr Thr Ser His Glu Arg Leu Thr Thr Tyr Lys
7745            7750            7755

Asp Thr Ala His Thr Glu Ala Val His Pro Ser Thr Asn Thr Gly
7760            7765            7770

Gly Thr Asn Val Ala Thr Thr Ser Ser Gly Tyr Lys Ser Gln Ser
7775            7780            7785

Ser Val Leu Ala Asp Ser Ser Pro Met Cys Thr Thr Ser Thr Met
7790            7795            7800
```

-continued

```
Gly Asp Thr Ser Val Leu Thr Ser Thr Pro Ala Phe Leu Glu Thr
7805                7810                7815

Arg Arg Ile Gln Thr Glu Leu Ala Ser Ser Leu Thr Pro Gly Leu
7820                7825                7830

Arg Glu Ser Ser Gly Ser Glu Gly Thr Ser Ser Gly Thr Lys Met
7835                7840                7845

Ser Thr Val Leu Ser Lys Val Pro Thr Gly Ala Thr Thr Glu Ile
7850                7855                7860

Ser Lys Glu Asp Val Thr Ser Ile Pro Gly Pro Ala Gln Ser Thr
7865                7870                7875

Ile Ser Pro Asp Ile Ser Thr Arg Thr Val Ser Trp Phe Ser Thr
7880                7885                7890

Ser Pro Val Met Thr Glu Ser Ala Glu Ile Thr Met Asn Thr His
7895                7900                7905

Thr Ser Pro Leu Gly Ala Thr Thr Gln Gly Thr Ser Thr Leu Asp
7910                7915                7920

Thr Ser Ser Thr Thr Ser Leu Thr Met Thr His Ser Thr Ile Ser
7925                7930                7935

Gln Gly Phe Ser His Ser Gln Met Ser Thr Leu Met Arg Arg Gly
7940                7945                7950

Pro Glu Asp Val Ser Trp Met Ser Pro Pro Leu Leu Glu Lys Thr
7955                7960                7965

Arg Pro Ser Phe Ser Leu Met Ser Ser Pro Ala Thr Thr Ser Pro
7970                7975                7980

Ser Pro Val Ser Ser Thr Leu Pro Glu Ser Ile Ser Ser Ser Pro
7985                7990                7995

Leu Pro Val Thr Ser Leu Leu Thr Ser Gly Leu Ala Lys Thr Thr
8000                8005                8010

Asp Met Leu His Lys Ser Ser Glu Pro Val Thr Asn Ser Pro Ala
8015                8020                8025

Asn Leu Ser Ser Thr Ser Val Glu Ile Leu Ala Thr Ser Glu Val
8030                8035                8040

Thr Thr Asp Thr Glu Lys Thr His Pro Ser Ser Asn Arg Thr Val
8045                8050                8055

Thr Asp Val Gly Thr Ser Ser Ser Gly His Glu Ser Thr Ser Phe
8060                8065                8070

Val Leu Ala Asp Ser Gln Thr Ser Lys Val Thr Ser Pro Met Val
8075                8080                8085

Ile Thr Ser Thr Met Glu Asp Thr Ser Val Ser Thr Ser Thr Pro
8090                8095                8100

Gly Phe Phe Glu Thr Ser Arg Ile Gln Thr Glu Pro Thr Ser Ser
8105                8110                8115

Leu Thr Leu Gly Leu Arg Lys Thr Ser Ser Ser Glu Gly Thr Ser
8120                8125                8130

Leu Ala Thr Glu Met Ser Thr Val Leu Ser Gly Val Pro Thr Gly
8135                8140                8145

Ala Thr Ala Glu Val Ser Arg Thr Glu Val Thr Ser Ser Ser Arg
8150                8155                8160

Thr Ser Ile Ser Gly Phe Ala Gln Leu Thr Val Ser Pro Glu Thr
8165                8170                8175

Ser Thr Glu Thr Ile Thr Arg Leu Pro Thr Ser Ser Ile Met Thr
8180                8185                8190
```

| | | | | | | | | | | | |
|---|---|---|---|---|---|---|---|---|---|---|---|
| Glu | Ser | Ala | Glu | Met | Met | Ile | Lys | Thr | Gln | Thr | Asp | Pro | Pro | Gly |
| | 8195 | | | | 8200 | | | | | 8205 | | | |

Glu Ser Ala Glu Met Met Ile Lys Thr Gln Thr Asp Pro Pro Gly
    8195                8200                8205

Ser Thr Pro Glu Ser Thr His Thr Val Asp Ile Ser Thr Thr Pro
    8210                8215                8220

Asn Trp Val Glu Thr His Ser Thr Val Thr Gln Arg Phe Ser His
    8225                8230                8235

Ser Glu Met Thr Thr Leu Val Ser Arg Ser Pro Gly Asp Met Leu
    8240                8245                8250

Trp Pro Ser Gln Ser Ser Val Glu Glu Thr Ser Ser Ala Ser Ser
    8255                8260                8265

Leu Leu Ser Leu Pro Ala Thr Thr Ser Pro Ser Pro Val Ser Ser
    8270                8275                8280

Thr Leu Val Glu Asp Phe Pro Ser Ala Ser Leu Pro Val Thr Ser
    8285                8290                8295

Leu Leu Asn Pro Gly Leu Val Ile Thr Thr Asp Arg Met Gly Ile
    8300                8305                8310

Ser Arg Glu Pro Gly Thr Ser Ser Thr Ser Asn Leu Ser Ser Thr
    8315                8320                8325

Ser His Glu Arg Leu Thr Thr Leu Glu Asp Thr Val Asp Thr Glu
    8330                8335                8340

Asp Met Gln Pro Ser Thr His Thr Ala Val Thr Asn Val Arg Thr
    8345                8350                8355

Ser Ile Ser Gly His Glu Ser Gln Ser Ser Val Leu Ser Asp Ser
    8360                8365                8370

Glu Thr Pro Lys Ala Thr Ser Pro Met Gly Thr Thr Tyr Thr Met
    8375                8380                8385

Gly Glu Thr Ser Val Ser Ile Ser Thr Ser Asp Phe Phe Glu Thr
    8390                8395                8400

Ser Arg Ile Gln Ile Glu Pro Thr Ser Ser Leu Thr Ser Gly Leu
    8405                8410                8415

Arg Glu Thr Ser Ser Ser Glu Arg Ile Ser Ser Ala Thr Glu Gly
    8420                8425                8430

Ser Thr Val Leu Ser Glu Val Pro Ser Gly Ala Thr Thr Glu Val
    8435                8440                8445

Ser Arg Thr Glu Val Ile Ser Ser Arg Gly Thr Ser Met Ser Gly
    8450                8455                8460

Pro Asp Gln Phe Thr Ile Ser Pro Asp Ile Ser Thr Glu Ala Ile
    8465                8470                8475

Thr Arg Leu Ser Thr Ser Pro Ile Met Thr Glu Ser Ala Glu Ser
    8480                8485                8490

Ala Ile Thr Ile Glu Thr Gly Ser Pro Gly Ala Thr Ser Glu Gly
    8495                8500                8505

Thr Leu Thr Leu Asp Thr Ser Thr Thr Thr Phe Trp Ser Gly Thr
    8510                8515                8520

His Ser Thr Ala Ser Pro Gly Phe Ser His Ser Glu Met Thr Thr
    8525                8530                8535

Leu Met Ser Arg Thr Pro Gly Asp Val Pro Trp Pro Ser Leu Pro
    8540                8545                8550

Ser Val Glu Glu Ala Ser Ser Val Ser Ser Ser Leu Ser Ser Pro
    8555                8560                8565

Ala Met Thr Ser Thr Ser Phe Phe Ser Thr Leu Pro Glu Ser Ile
    8570                8575                8580

```
Ser Ser Ser Pro His Pro Val Thr Ala Leu Leu Thr Leu Gly Pro
    8585                8590                8595

Val Lys Thr Thr Asp Met Leu Arg Thr Ser Ser Glu Pro Glu Thr
    8600                8605                8610

Ser Ser Pro Pro Asn Leu Ser Ser Thr Ser Ala Glu Ile Leu Ala
    8615                8620                8625

Thr Ser Glu Val Thr Lys Asp Arg Glu Lys Ile His Pro Ser Ser
    8630                8635                8640

Asn Thr Pro Val Val Asn Val Gly Thr Val Ile Tyr Lys His Leu
    8645                8650                8655

Ser Pro Ser Ser Val Leu Ala Asp Leu Val Thr Thr Lys Pro Thr
    8660                8665                8670

Ser Pro Met Ala Thr Thr Ser Thr Leu Gly Asn Thr Ser Val Ser
    8675                8680                8685

Thr Ser Thr Pro Ala Phe Pro Glu Thr Met Met Thr Gln Pro Thr
    8690                8695                8700

Ser Ser Leu Thr Ser Gly Leu Arg Glu Ile Ser Thr Ser Gln Glu
    8705                8710                8715

Thr Ser Ser Ala Thr Glu Arg Ser Ala Ser Leu Ser Gly Met Pro
    8720                8725                8730

Thr Gly Ala Thr Thr Lys Val Ser Arg Thr Glu Ala Leu Ser Leu
    8735                8740                8745

Gly Arg Thr Ser Thr Pro Gly Pro Ala Gln Ser Thr Ile Ser Pro
    8750                8755                8760

Glu Ile Ser Thr Glu Thr Ile Thr Arg Ile Ser Thr Pro Leu Thr
    8765                8770                8775

Thr Thr Gly Ser Ala Glu Met Thr Ile Thr Pro Lys Thr Gly His
    8780                8785                8790

Ser Gly Ala Ser Ser Gln Gly Thr Phe Thr Leu Asp Thr Ser Ser
    8795                8800                8805

Arg Ala Ser Trp Pro Gly Thr His Ser Ala Ala Thr His Arg Ser
    8810                8815                8820

Pro His Ser Gly Met Thr Thr Pro Met Ser Arg Gly Pro Glu Asp
    8825                8830                8835

Val Ser Trp Pro Ser Arg Pro Ser Val Glu Lys Thr Ser Pro Pro
    8840                8845                8850

Ser Ser Leu Val Ser Leu Ser Ala Val Thr Ser Pro Ser Pro Leu
    8855                8860                8865

Tyr Ser Thr Pro Ser Glu Ser Ser His Ser Ser Pro Leu Arg Val
    8870                8875                8880

Thr Ser Leu Phe Thr Pro Val Met Met Lys Thr Thr Asp Met Leu
    8885                8890                8895

Asp Thr Ser Leu Glu Pro Val Thr Thr Ser Pro Ser Met Asn
    8900                8905                8910

Ile Thr Ser Asp Glu Ser Leu Ala Thr Ser Lys Ala Thr Met Glu
    8915                8920                8925

Thr Glu Ala Ile Gln Leu Ser Glu Asn Thr Ala Val Thr Gln Met
    8930                8935                8940

Gly Thr Ile Ser Ala Arg Gln Glu Phe Tyr Ser Ser Tyr Pro Gly
    8945                8950                8955

Leu Pro Glu Pro Ser Lys Val Thr Ser Pro Val Val Thr Ser Ser
    8960                8965                8970
```

-continued

| | | | | | | | | | | | |
|---|---|---|---|---|---|---|---|---|---|---|---|
| Thr | Ile | Lys | Asp | Ile | Val | Ser | Thr | Thr | Ile | Pro | Ala | Ser | Ser | Glu |
| 8975 | | | | | 8980 | | | | | 8985 | | | | |

Thr Ile Lys Asp Ile Val Ser Thr Thr Ile Pro Ala Ser Ser Glu
8975                   8980              8985

Ile Thr Arg Ile Glu Met Glu Ser Thr Ser Thr Leu Thr Pro Thr
8990                   8995              9000

Pro Arg Glu Thr Ser Thr Ser Gln Glu Ile His Ser Ala Thr Lys
9005                   9010              9015

Pro Ser Thr Val Pro Tyr Lys Ala Leu Thr Ser Ala Thr Ile Glu
9020                   9025              9030

Asp Ser Met Thr Gln Val Met Ser Ser Ser Arg Gly Pro Ser Pro
9035                   9040              9045

Asp Gln Ser Thr Met Ser Gln Asp Ile Ser Thr Glu Val Ile Thr
9050                   9055              9060

Arg Leu Ser Thr Ser Pro Ile Lys Thr Glu Ser Thr Glu Met Thr
9065                   9070              9075

Ile Thr Thr Gln Thr Gly Ser Pro Gly Ala Thr Ser Arg Gly Thr
9080                   9085              9090

Leu Thr Leu Asp Thr Ser Thr Thr Phe Met Ser Gly Thr His Ser
9095                   9100              9105

Thr Ala Ser Gln Gly Phe Ser His Ser Gln Met Thr Ala Leu Met
9110                   9115              9120

Ser Arg Thr Pro Gly Asp Val Pro Trp Leu Ser His Pro Ser Val
9125                   9130              9135

Glu Glu Ala Ser Ser Ala Ser Phe Ser Leu Ser Ser Pro Val Met
9140                   9145              9150

Thr Ser Ser Ser Pro Val Ser Ser Thr Leu Pro Asp Ser Ile His
9155                   9160              9165

Ser Ser Ser Leu Pro Val Thr Ser Leu Leu Thr Ser Gly Leu Val
9170                   9175              9180

Lys Thr Thr Glu Leu Leu Gly Thr Ser Ser Glu Pro Glu Thr Ser
9185                   9190              9195

Ser Pro Pro Asn Leu Ser Ser Thr Ser Ala Glu Ile Leu Ala Ile
9200                   9205              9210

Thr Glu Val Thr Thr Asp Thr Glu Lys Leu Glu Met Thr Asn Val
9215                   9220              9225

Val Thr Ser Gly Tyr Thr His Glu Ser Pro Ser Ser Val Leu Ala
9230                   9235              9240

Asp Ser Val Thr Thr Lys Ala Thr Ser Ser Met Gly Ile Thr Tyr
9245                   9250              9255

Pro Thr Gly Asp Thr Asn Val Leu Thr Ser Thr Pro Ala Phe Ser
9260                   9265              9270

Asp Thr Ser Arg Ile Gln Thr Lys Ser Lys Leu Ser Leu Thr Pro
9275                   9280              9285

Gly Leu Met Glu Thr Ser Ile Ser Glu Glu Thr Ser Ser Ala Thr
9290                   9295              9300

Glu Lys Ser Thr Val Leu Ser Ser Val Pro Thr Gly Ala Thr Thr
9305                   9310              9315

Glu Val Ser Arg Thr Glu Ala Ile Ser Ser Ser Arg Thr Ser Ile
9320                   9325              9330

Pro Gly Pro Ala Gln Ser Thr Met Ser Ser Asp Thr Ser Met Glu
9335                   9340              9345

Thr Ile Thr Arg Ile Ser Thr Pro Leu Thr Arg Lys Glu Ser Thr
9350                   9355              9360

-continued

```
Asp Met Ala Ile Thr Pro Lys Thr Gly Pro Ser Gly Ala Thr Ser
    9365            9370            9375

Gln Gly Thr Phe Thr Leu Asp Ser Ser Thr Ala Ser Trp Pro
    9380            9385            9390

Gly Thr His Ser Ala Thr Thr Gln Arg Phe Pro Gln Ser Val Val
    9395            9400            9405

Thr Thr Pro Met Ser Arg Gly Pro Glu Asp Val Ser Trp Pro Ser
    9410            9415            9420

Pro Leu Ser Val Glu Lys Asn Ser Pro Pro Ser Ser Leu Val Ser
    9425            9430            9435

Ser Ser Ser Val Thr Ser Pro Ser Pro Leu Tyr Ser Thr Pro Ser
    9440            9445            9450

Gly Ser Ser His Ser Ser Pro Val Pro Val Thr Ser Leu Phe Thr
    9455            9460            9465

Ser Ile Met Met Lys Ala Thr Asp Met Leu Asp Ala Ser Leu Glu
    9470            9475            9480

Pro Glu Thr Thr Ser Ala Pro Asn Met Asn Ile Thr Ser Asp Glu
    9485            9490            9495

Ser Leu Ala Ala Ser Lys Ala Thr Thr Glu Thr Glu Ala Ile His
    9500            9505            9510

Val Phe Glu Asn Thr Ala Ala Ser His Val Glu Thr Thr Ser Ala
    9515            9520            9525

Thr Glu Glu Leu Tyr Ser Ser Ser Pro Gly Phe Ser Glu Pro Thr
    9530            9535            9540

Lys Val Ile Ser Pro Val Val Thr Ser Ser Ser Ile Arg Asp Asn
    9545            9550            9555

Met Val Ser Thr Thr Met Pro Gly Ser Ser Gly Ile Thr Arg Ile
    9560            9565            9570

Glu Ile Glu Ser Met Ser Ser Leu Thr Pro Gly Leu Arg Glu Thr
    9575            9580            9585

Arg Thr Ser Gln Asp Ile Thr Ser Ser Thr Glu Thr Ser Thr Val
    9590            9595            9600

Leu Tyr Lys Met Pro Ser Gly Ala Thr Pro Glu Val Ser Arg Thr
    9605            9610            9615

Glu Val Met Pro Ser Ser Arg Thr Ser Ile Pro Gly Pro Ala Gln
    9620            9625            9630

Ser Thr Met Ser Leu Asp Ile Ser Asp Glu Val Val Thr Arg Leu
    9635            9640            9645

Ser Thr Ser Pro Ile Met Thr Glu Ser Ala Glu Ile Thr Ile Thr
    9650            9655            9660

Thr Gln Thr Gly Tyr Ser Leu Ala Thr Ser Gln Val Thr Leu Pro
    9665            9670            9675

Leu Gly Thr Ser Met Thr Phe Leu Ser Gly Thr His Ser Thr Met
    9680            9685            9690

Ser Gln Gly Leu Ser His Ser Glu Met Thr Asn Leu Met Ser Arg
    9695            9700            9705

Gly Pro Glu Ser Leu Ser Trp Thr Ser Pro Arg Phe Val Glu Thr
    9710            9715            9720

Thr Arg Ser Ser Ser Ser Leu Thr Ser Leu Pro Leu Thr Thr Ser
    9725            9730            9735

Leu Ser Pro Val Ser Ser Thr Leu Leu Asp Ser Ser Pro Ser Ser
    9740            9745            9750
```

```
Pro Leu Pro Val Thr Ser Leu Ile Leu Pro Gly Leu Val Lys Thr
    9755            9760            9765

Thr Glu Val Leu Asp Thr Ser Ser Glu Pro Lys Thr Ser Ser Ser
    9770            9775            9780

Pro Asn Leu Ser Ser Thr Ser Val Glu Ile Pro Ala Thr Ser Glu
    9785            9790            9795

Ile Met Thr Asp Thr Glu Lys Ile His Pro Ser Ser Asn Thr Ala
    9800            9805            9810

Val Ala Lys Val Arg Thr Ser Ser Val His Glu Ser His Ser
    9815            9820            9825

Ser Val Leu Ala Asp Ser Glu Thr Thr Ile Thr Ile Pro Ser Met
    9830            9835            9840

Gly Ile Thr Ser Ala Val Asp Asp Thr Thr Val Phe Thr Ser Asn
    9845            9850            9855

Pro Ala Phe Ser Glu Thr Arg Arg Ile Pro Thr Glu Pro Thr Phe
    9860            9865            9870

Ser Leu Thr Pro Gly Phe Arg Glu Thr Ser Thr Ser Glu Glu Thr
    9875            9880            9885

Thr Ser Ile Thr Glu Thr Ser Ala Val Leu Tyr Gly Val Pro Thr
    9890            9895            9900

Ser Ala Thr Thr Glu Val Ser Met Thr Glu Ile Met Ser Ser Asn
    9905            9910            9915

Arg Ile His Ile Pro Asp Ser Asp Gln Ser Thr Met Ser Pro Asp
    9920            9925            9930

Ile Ile Thr Glu Val Ile Thr Arg Leu Ser Ser Ser Ser Met Met
    9935            9940            9945

Ser Glu Ser Thr Gln Met Thr Ile Thr Thr Gln Lys Ser Ser Pro
    9950            9955            9960

Gly Ala Thr Ala Gln Ser Thr Leu Thr Leu Ala Thr Thr Thr Ala
    9965            9970            9975

Pro Leu Ala Arg Thr His Ser Thr Val Pro Pro Arg Phe Leu His
    9980            9985            9990

Ser Glu Met Thr Thr Leu Met Ser Arg Ser Pro Glu Asn Pro Ser
    9995            10000           10005

Trp Lys Ser Ser Leu Phe Val Glu Lys Thr Ser Ser Ser Ser Ser
    10010           10015           10020

Leu Leu Ser Leu Pro Val Thr Thr Ser Pro Ser Val Ser Ser Thr
    10025           10030           10035

Leu Pro Gln Ser Ile Pro Ser Ser Ser Phe Ser Val Thr Ser Leu
    10040           10045           10050

Leu Thr Pro Gly Met Val Lys Thr Thr Asp Thr Ser Thr Glu Pro
    10055           10060           10065

Gly Thr Ser Leu Ser Pro Asn Leu Ser Gly Thr Ser Val Glu Ile
    10070           10075           10080

Leu Ala Ala Ser Glu Val Thr Thr Asp Thr Glu Lys Ile His Pro
    10085           10090           10095

Ser Ser Ser Met Ala Val Thr Asn Val Gly Thr Thr Ser Ser Gly
    10100           10105           10110

His Glu Leu Tyr Ser Ser Val Ser Ile His Ser Glu Pro Ser Lys
    10115           10120           10125

Ala Thr Tyr Pro Val Gly Thr Pro Ser Ser Met Ala Glu Thr Ser
    10130           10135           10140
```

-continued

Ile Ser Thr Ser Met Pro Ala Asn Phe Glu Thr Thr Gly Phe Glu
10145                10150                10155

Ala Glu Pro Phe Ser His Leu Thr Ser Gly Phe Arg Lys Thr Asn
10160                10165                10170

Met Ser Leu Asp Thr Ser Ser Val Thr Pro Thr Asn Thr Pro Ser
10175                10180                10185

Ser Pro Gly Ser Thr His Leu Leu Gln Ser Ser Lys Thr Asp Phe
10190                10195                10200

Thr Ser Ser Ala Lys Thr Ser Ser Pro Asp Trp Pro Pro Ala Ser
10205                10210                10215

Gln Tyr Thr Glu Ile Pro Val Asp Ile Ile Thr Pro Phe Asn Ala
10220                10225                10230

Ser Pro Ser Ile Thr Glu Ser Thr Gly Ile Thr Ser Phe Pro Glu
10235                10240                10245

Ser Arg Phe Thr Met Ser Val Thr Glu Ser Thr His His Leu Ser
10250                10255                10260

Thr Asp Leu Leu Pro Ser Ala Glu Thr Ile Ser Thr Gly Thr Val
10265                10270                10275

Met Pro Ser Leu Ser Glu Ala Met Thr Ser Phe Ala Thr Thr Gly
10280                10285                10290

Val Pro Arg Ala Ile Ser Gly Ser Gly Ser Pro Phe Ser Arg Thr
10295                10300                10305

Glu Ser Gly Pro Gly Asp Ala Thr Leu Ser Thr Ile Ala Glu Ser
10310                10315                10320

Leu Pro Ser Ser Thr Pro Val Pro Phe Ser Ser Ser Thr Phe Thr
10325                10330                10335

Thr Thr Asp Ser Ser Thr Ile Pro Ala Leu His Glu Ile Thr Ser
10340                10345                10350

Ser Ser Ala Thr Pro Tyr Arg Val Asp Thr Ser Leu Gly Thr Glu
10355                10360                10365

Ser Ser Thr Thr Glu Gly Arg Leu Val Met Val Ser Thr Leu Asp
10370                10375                10380

Thr Ser Ser Gln Pro Gly Arg Thr Ser Ser Pro Ile Leu Asp
10385                10390                10395

Thr Arg Met Thr Glu Ser Val Glu Leu Gly Thr Val Thr Ser Ala
10400                10405                10410

Tyr Gln Val Pro Ser Leu Ser Thr Arg Leu Thr Arg Thr Asp Gly
10415                10420                10425

Ile Met Glu His Ile Thr Lys Ile Pro Asn Glu Ala Ala His Arg
10430                10435                10440

Gly Thr Ile Arg Pro Val Lys Gly Pro Gln Thr Ser Thr Ser Pro
10445                10450                10455

Ala Ser Pro Lys Gly Leu His Thr Gly Gly Thr Lys Arg Met Glu
10460                10465                10470

Thr Thr Thr Thr Ala Leu Lys Thr Thr Thr Thr Ala Leu Lys Thr
10475                10480                10485

Thr Ser Arg Ala Thr Leu Thr Thr Ser Val Tyr Thr Pro Thr Leu
10490                10495                10500

Gly Thr Leu Thr Pro Leu Asn Ala Ser Met Gln Met Ala Ser Thr
10505                10510                10515

Ile Pro Thr Glu Met Met Ile Thr Thr Pro Tyr Val Phe Pro Asp
10520                10525                10530

```
Val Pro Glu Thr Thr Ser Ser   Leu Ala Thr Ser   Leu Gly Ala Glu
    10535                 10540             10545

Thr Ser Thr Ala Leu Pro Arg   Thr Thr Pro Ser   Val Phe Asn Arg
    10550                 10555             10560

Glu Ser Glu Thr Thr Ala Ser   Leu Val Ser Arg   Ser Gly Ala Glu
    10565                 10570             10575

Arg Ser Pro Val Ile Gln Thr   Leu Asp Val Ser   Ser Ser Glu Pro
    10580                 10585             10590

Asp Thr Thr Ala Ser Trp Val   Ile His Pro Ala Glu   Thr Ile Pro
    10595                 10600             10605

Thr Val Ser Lys Thr Thr Pro   Asn Phe Phe His Ser   Glu Leu Asp
    10610                 10615             10620

Thr Val Ser Ser Thr Ala Thr   Ser His Gly Ala Asp   Val Ser Ser
    10625                 10630             10635

Ala Ile Pro Thr Asn Ile Ser   Pro Ser Glu Leu Asp   Ala Leu Thr
    10640                 10645             10650

Pro Leu Val Thr Ile Ser Gly   Thr Asp Thr Ser   Thr Phe Pro
    10655                 10660             10665

Thr Leu Thr Lys Ser Pro His   Glu Thr Glu Thr Arg   Thr Thr Trp
    10670                 10675             10680

Leu Thr His Pro Ala Glu Thr   Ser Ser Thr Ile Pro   Arg Thr Ile
    10685                 10690             10695

Pro Asn Phe Ser His His Glu   Ser Asp Ala Thr Pro   Ser Ile Ala
    10700                 10705             10710

Thr Ser Pro Gly Ala Glu Thr   Ser Ser Ala Ile Pro   Ile Met Thr
    10715                 10720             10725

Val Ser Pro Gly Ala Glu Asp   Leu Val Thr Ser Gln   Val Thr Ser
    10730                 10735             10740

Ser Gly Thr Asp Arg Asn Met   Thr Ile Pro Thr Leu   Thr Leu Ser
    10745                 10750             10755

Pro Gly Glu Pro Lys Thr Ile   Ala Ser Leu Val Thr   His Pro Glu
    10760                 10765             10770

Ala Gln Thr Ser Ser Ala Ile   Pro Thr Ser Thr Ile   Ser Pro Ala
    10775                 10780             10785

Val Ser Arg Leu Val Thr Ser   Met Val Thr Ser Leu   Ala Ala Lys
    10790                 10795             10800

Thr Ser Thr Thr Asn Arg Ala   Leu Thr Asn Ser Pro   Gly Glu Pro
    10805                 10810             10815

Ala Thr Thr Val Ser Leu Val   Thr His Pro Ala Gln   Thr Ser Pro
    10820                 10825             10830

Thr Val Pro Trp Thr Thr Ser   Ile Phe Phe His Ser   Lys Ser Asp
    10835                 10840             10845

Thr Thr Pro Ser Met Thr Thr   Ser His Gly Ala Glu   Ser Ser Ser
    10850                 10855             10860

Ala Val Pro Thr Pro Thr Val   Ser Thr Glu Val Pro   Gly Val Val
    10865                 10870             10875

Thr Pro Leu Val Thr Ser Ser   Arg Ala Val Ile Ser   Thr Thr Ile
    10880                 10885             10890

Pro Ile Leu Thr Leu Ser Pro   Gly Glu Pro Glu Thr   Thr Pro Ser
    10895                 10900             10905

Met Ala Thr Ser His Gly Glu   Glu Ala Ser Ser Ala   Ile Pro Thr
    10910                 10915             10920
```

```
Pro Thr Val Ser Pro Gly Val Pro Gly Val Val Thr     Ser Leu Val
    10925           10930           10935

Thr Ser Ser Arg Ala Val Thr Ser Thr Thr Ile Pro     Ile Leu Thr
    10940           10945           10950

Phe Ser Leu Gly Glu Pro Glu Thr Thr Pro Ser Met     Ala Thr Ser
    10955           10960           10965

His Gly Thr Glu Ala Gly Ser Ala Val Pro Thr Val     Leu Pro Glu
    10970           10975           10980

Val Pro Gly Met Val Thr Ser Leu Val Ala Ser Ser     Arg Ala Val
    10985           10990           10995

Thr Ser Thr Thr Leu Pro Thr Leu Thr Leu Ser Pro     Gly Glu Pro
    11000           11005           11010

Glu Thr Thr Pro Ser Met Ala Thr Ser His Gly Ala     Glu Ala Ser
    11015           11020           11025

Ser Thr Val Pro Thr Val Ser Pro Glu Val Pro Gly     Val Val Thr
    11030           11035           11040

Ser Leu Val Thr Ser Ser Ser Gly Val Asn Ser Thr     Ser Ile Pro
    11045           11050           11055

Thr Leu Ile Leu Ser Pro Gly Glu Leu Glu Thr Thr     Pro Ser Met
    11060           11065           11070

Ala Thr Ser His Gly Ala Glu Ala Ser Ser Ala Val     Pro Thr Pro
    11075           11080           11085

Thr Val Ser Pro Gly Val Ser Gly Val Val Thr Pro     Leu Val Thr
    11090           11095           11100

Ser Ser Arg Ala Val Thr Ser Thr Thr Ile Pro Ile     Leu Thr Leu
    11105           11110           11115

Ser Ser Ser Glu Pro Glu Thr Thr Pro Ser Met Ala     Thr Ser His
    11120           11125           11130

Gly Val Glu Ala Ser Ser Ala Val Leu Thr Val Ser     Pro Glu Val
    11135           11140           11145

Pro Gly Met Val Thr Ser Leu Val Thr Ser Ser Arg     Ala Val Thr
    11150           11155           11160

Ser Thr Thr Ile Pro Thr Leu Thr Ile Ser Ser Asp     Glu Pro Glu
    11165           11170           11175

Thr Thr Thr Ser Leu Val Thr His Ser Glu Ala Lys     Met Ile Ser
    11180           11185           11190

Ala Ile Pro Thr Leu Ala Val Ser Pro Thr Val Gln     Gly Leu Val
    11195           11200           11205

Thr Ser Leu Val Thr Ser Ser Gly Ser Glu Thr Ser     Ala Phe Ser
    11210           11215           11220

Asn Leu Thr Val Ala Ser Ser Gln Pro Glu Thr Ile     Asp Ser Trp
    11225           11230           11235

Val Ala His Pro Gly Thr Glu Ala Ser Ser Val Val     Pro Thr Leu
    11240           11245           11250

Thr Val Ser Thr Gly Glu Pro Phe Thr Asn Ile Ser     Leu Val Thr
    11255           11260           11265

His Pro Ala Glu Ser Ser Ser Thr Leu Pro Arg Thr     Thr Ser Arg
    11270           11275           11280

Phe Ser His Ser Glu Leu Asp Thr Met Pro Ser Thr     Val Thr Ser
    11285           11290           11295

Pro Glu Ala Glu Ser Ser Ser Ala Ile Ser Thr Thr     Ile Ser Pro
    11300           11305           11310
```

```
Gly Ile Pro Gly Val Leu Thr  Ser Leu Val Thr  Ser Ser Gly Arg
    11315           11320              11325

Asp Ile Ser Ala Thr Phe Pro  Thr Val Pro Glu Ser  Pro His Glu
    11330           11335              11340

Ser Glu Ala Thr Ala Ser Trp  Val Thr His Pro Ala  Val Thr Ser
    11345           11350              11355

Thr Thr Val Pro Arg Thr Thr  Pro Asn Tyr Ser His  Ser Glu Pro
    11360           11365              11370

Asp Thr Thr Pro Ser Ile Ala  Thr Ser Pro Gly Ala  Glu Ala Thr
    11375           11380              11385

Ser Asp Phe Pro Thr Ile Thr  Val Ser Pro Asp Val  Pro Asp Met
    11390           11395              11400

Val Thr Ser Gln Val Thr Ser  Ser Gly Thr Asp Thr  Ser Ile Thr
    11405           11410              11415

Ile Pro Thr Leu Thr Leu Ser  Ser Gly Glu Pro Glu  Thr Thr Thr
    11420           11425              11430

Ser Phe Ile Thr Tyr Ser Glu  Thr His Thr Ser Ser  Ala Ile Pro
    11435           11440              11445

Thr Leu Pro Val Ser Pro Gly  Ala Ser Lys Met Leu  Thr Ser Leu
    11450           11455              11460

Val Ile Ser Ser Gly Thr Asp  Ser Thr Thr Thr Phe  Pro Thr Leu
    11465           11470              11475

Thr Glu Thr Pro Tyr Glu Pro  Glu Thr Thr Ala Ile  Gln Leu Ile
    11480           11485              11490

His Pro Ala Glu Thr Asn Thr  Met Val Pro Arg Thr  Thr Pro Lys
    11495           11500              11505

Phe Ser His Ser Lys Ser Asp  Thr Thr Leu Pro Val  Ala Ile Thr
    11510           11515              11520

Ser Pro Gly Pro Glu Ala Ser  Ser Ala Val Ser Thr  Thr Thr Ile
    11525           11530              11535

Ser Pro Asp Met Ser Asp Leu  Val Thr Ser Leu Val  Pro Ser Ser
    11540           11545              11550

Gly Thr Asp Thr Ser Thr Thr  Phe Pro Thr Leu Ser  Glu Thr Pro
    11555           11560              11565

Tyr Glu Pro Glu Thr Thr Ala  Thr Trp Leu Thr His  Pro Ala Glu
    11570           11575              11580

Thr Ser Thr Thr Val Ser Gly  Thr Ile Pro Asn Phe  Ser His Arg
    11585           11590              11595

Gly Ser Asp Thr Ala Pro Ser  Met Val Thr Ser Pro  Gly Val Asp
    11600           11605              11610

Thr Arg Ser Gly Val Pro Thr  Thr Thr Ile Pro Pro  Ser Ile Pro
    11615           11620              11625

Gly Val Val Thr Ser Gln Val  Thr Ser Ser Ala Thr  Asp Thr Ser
    11630           11635              11640

Thr Ala Ile Pro Thr Leu Thr  Pro Ser Pro Gly Glu  Pro Glu Thr
    11645           11650              11655

Thr Ala Ser Ser Ala Thr His  Pro Gly Thr Gln Thr  Gly Phe Thr
    11660           11665              11670

Val Pro Ile Arg Thr Val Pro  Ser Ser Glu Pro Asp  Thr Met Ala
    11675           11680              11685

Ser Trp Val Thr His Pro Pro  Gln Thr Ser Thr Pro  Val Ser Arg
    11690           11695              11700
```

```
Thr  Thr  Ser  Ser  Phe  Ser  His  Ser  Ser  Pro  Asp  Ala  Thr  Pro  Val
     11705               11710                    11715

Met  Ala  Thr  Ser  Pro  Arg  Thr  Glu  Ala  Ser  Ser  Ala  Val  Leu  Thr
     11720               11725                    11730

Thr  Ile  Ser  Pro  Gly  Ala  Pro  Glu  Met  Val  Thr  Ser  Gln  Ile  Thr
     11735               11740                    11745

Ser  Ser  Gly  Ala  Ala  Thr  Ser  Thr  Thr  Val  Pro  Thr  Leu  Thr  His
     11750               11755                    11760

Ser  Pro  Gly  Met  Pro  Glu  Thr  Thr  Ala  Leu  Leu  Ser  Thr  His  Pro
     11765               11770                    11775

Arg  Thr  Glu  Thr  Ser  Lys  Thr  Phe  Pro  Ala  Ser  Thr  Val  Phe  Pro
     11780               11785                    11790

Gln  Val  Ser  Glu  Thr  Thr  Ala  Ser  Leu  Thr  Ile  Arg  Pro  Gly  Ala
     11795               11800                    11805

Glu  Thr  Ser  Thr  Ala  Leu  Pro  Thr  Gln  Thr  Thr  Ser  Ser  Leu  Phe
     11810               11815                    11820

Thr  Leu  Leu  Val  Thr  Gly  Thr  Ser  Arg  Val  Asp  Leu  Ser  Pro  Thr
     11825               11830                    11835

Ala  Ser  Pro  Gly  Val  Ser  Ala  Lys  Thr  Ala  Pro  Leu  Ser  Thr  His
     11840               11845                    11850

Pro  Gly  Thr  Glu  Thr  Ser  Thr  Met  Ile  Pro  Thr  Ser  Thr  Leu  Ser
     11855               11860                    11865

Leu  Gly  Leu  Leu  Glu  Thr  Thr  Gly  Leu  Leu  Ala  Thr  Ser  Ser  Ser
     11870               11875                    11880

Ala  Glu  Thr  Ser  Thr  Ser  Thr  Leu  Thr  Leu  Thr  Val  Ser  Pro  Ala
     11885               11890                    11895

Val  Ser  Gly  Leu  Ser  Ser  Ala  Ser  Ile  Thr  Thr  Asp  Lys  Pro  Gln
     11900               11905                    11910

Thr  Val  Thr  Ser  Trp  Asn  Thr  Glu  Thr  Ser  Pro  Ser  Val  Thr  Ser
     11915               11920                    11925

Val  Gly  Pro  Pro  Glu  Phe  Ser  Arg  Thr  Val  Thr  Gly  Thr  Thr  Met
     11930               11935                    11940

Thr  Leu  Ile  Pro  Ser  Glu  Met  Pro  Thr  Pro  Pro  Lys  Thr  Ser  His
     11945               11950                    11955

Gly  Glu  Gly  Val  Ser  Pro  Thr  Thr  Ile  Leu  Arg  Thr  Thr  Met  Val
     11960               11965                    11970

Glu  Ala  Thr  Asn  Leu  Ala  Thr  Thr  Gly  Ser  Ser  Pro  Thr  Val  Ala
     11975               11980                    11985

Lys  Thr  Thr  Thr  Thr  Phe  Asn  Thr  Leu  Ala  Gly  Ser  Leu  Phe  Thr
     11990               11995                    12000

Pro  Leu  Thr  Thr  Pro  Gly  Met  Ser  Thr  Leu  Ala  Ser  Glu  Ser  Val
     12005               12010                    12015

Thr  Ser  Arg  Thr  Ser  Tyr  Asn  His  Arg  Ser  Trp  Ile  Ser  Thr  Thr
     12020               12025                    12030

Ser  Ser  Tyr  Asn  Arg  Arg  Tyr  Trp  Thr  Pro  Ala  Thr  Ser  Thr  Pro
     12035               12040                    12045

Val  Thr  Ser  Thr  Phe  Ser  Pro  Gly  Ile  Ser  Thr  Ser  Ser  Ile  Pro
     12050               12055                    12060

Ser  Ser  Thr  Ala  Ala  Thr  Val  Pro  Phe  Met  Val  Pro  Phe  Thr  Leu
     12065               12070                    12075

Asn  Phe  Thr  Ile  Thr  Asn  Leu  Gln  Tyr  Glu  Glu  Asp  Met  Arg  His
     12080               12085                    12090
```

```
Pro Gly Ser Arg Lys Phe Asn  Ala Thr Glu Arg Glu  Leu Gln Gly
    12095                     12100                12105

Leu Leu Lys Pro Leu Phe Arg  Asn Ser Ser Leu Glu  Tyr Leu Tyr
    12110                     12115                12120

Ser Gly Cys Arg Leu Ala Ser  Leu Arg Pro Glu Lys  Asp Ser Ser
    12125                     12130                12135

Ala Thr Ala Val Asp Ala Ile  Cys Thr His Arg Pro  Asp Pro Glu
    12140                     12145                12150

Asp Leu Gly Leu Asp Arg Glu  Arg Leu Tyr Trp Glu  Leu Ser Asn
    12155                     12160                12165

Leu Thr Asn Gly Ile Gln Glu  Leu Gly Pro Tyr Thr  Leu Asp Arg
    12170                     12175                12180

Asn Ser Leu Tyr Val Asn Gly  Phe Thr His Arg Ser  Ser Met Pro
    12185                     12190                12195

Thr Thr Ser Thr Pro Gly Thr  Ser Thr Val Asp Val  Gly Thr Ser
    12200                     12205                12210

Gly Thr Pro Ser Ser Ser Pro  Ser Pro Thr Thr Ala  Gly Pro Leu
    12215                     12220                12225

Leu Met Pro Phe Thr Leu Asn  Phe Thr Ile Thr Asn  Leu Gln Tyr
    12230                     12235                12240

Glu Glu Asp Met Arg Arg Thr  Gly Ser Arg Lys Phe  Asn Thr Met
    12245                     12250                12255

Glu Ser Val Leu Gln Gly Leu  Leu Lys Pro Leu Phe  Lys Asn Thr
    12260                     12265                12270

Ser Val Gly Pro Leu Tyr Ser  Gly Cys Arg Leu Thr  Leu Leu Arg
    12275                     12280                12285

Pro Glu Lys Asp Gly Ala Ala  Thr Gly Val Asp Ala  Ile Cys Thr
    12290                     12295                12300

His Arg Leu Asp Pro Lys Ser  Pro Gly Leu Asn Arg  Glu Gln Leu
    12305                     12310                12315

Tyr Trp Glu Leu Ser Lys Leu  Thr Asn Asp Ile Glu  Glu Leu Gly
    12320                     12325                12330

Pro Tyr Thr Leu Asp Arg Asn  Ser Leu Tyr Val Asn  Gly Phe Thr
    12335                     12340                12345

His Gln Ser Ser Val Ser Thr  Thr Ser Thr Pro Gly  Thr Ser Thr
    12350                     12355                12360

Val Asp Leu Arg Thr Ser Gly  Thr Pro Ser Ser Leu  Ser Ser Pro
    12365                     12370                12375

Thr Ile Met Ala Ala Gly Pro  Leu Leu Val Pro Phe  Thr Leu Asn
    12380                     12385                12390

Phe Thr Ile Thr Asn Leu Gln  Tyr Gly Glu Asp Met  Gly His Pro
    12395                     12400                12405

Gly Ser Arg Lys Phe Asn Thr  Thr Glu Arg Val Leu  Gln Gly Leu
    12410                     12415                12420

Leu Gly Pro Ile Phe Lys Asn  Thr Ser Val Gly Pro  Leu Tyr Ser
    12425                     12430                12435

Gly Cys Arg Leu Thr Ser Leu  Arg Ser Glu Lys Asp  Gly Ala Ala
    12440                     12445                12450

Thr Gly Val Asp Ala Ile Cys  Ile His His Leu Asp  Pro Lys Ser
    12455                     12460                12465

Pro Gly Leu Asn Arg Glu Arg  Leu Tyr Trp Glu Leu  Ser Gln Leu
    12470                     12475                12480
```

-continued

| | | | | | | | | | | | |
|---|---|---|---|---|---|---|---|---|---|---|---|
| Thr | Asn | Gly | Ile | Lys | Glu | Leu | Gly | Pro | Tyr | Thr | Leu | Asp | Arg | Asn |
| | 12485 | | | | 12490 | | | | | 12495 | | | | |
| Ser | Leu | Tyr | Val | Asn | Gly | Phe | Thr | His | Arg | Thr | Ser | Val | Pro | Thr |
| 12500 | | | | | 12505 | | | | | 12510 | | | | |
| Ser | Ser | Thr | Pro | Gly | Thr | Ser | Thr | Val | Asp | Leu | Gly | Thr | Ser | Gly |
| 12515 | | | | | 12520 | | | | | 12525 | | | | |
| Thr | Pro | Phe | Ser | Leu | Pro | Ser | Pro | Ala | Thr | Ala | Gly | Pro | Leu | Leu |
| 12530 | | | | | 12535 | | | | | 12540 | | | | |
| Val | Leu | Phe | Thr | Leu | Asn | Phe | Thr | Ile | Thr | Asn | Leu | Lys | Tyr | Glu |
| 12545 | | | | | 12550 | | | | | 12555 | | | | |
| Glu | Asp | Met | His | Arg | Pro | Gly | Ser | Arg | Lys | Phe | Asn | Thr | Thr | Glu |
| 12560 | | | | | 12565 | | | | | 12570 | | | | |
| Arg | Val | Leu | Gln | Thr | Leu | Leu | Gly | Pro | Met | Phe | Lys | Asn | Thr | Ser |
| 12575 | | | | | 12580 | | | | | 12585 | | | | |
| Val | Gly | Leu | Leu | Tyr | Ser | Gly | Cys | Arg | Leu | Thr | Leu | Leu | Arg | Ser |
| 12590 | | | | | 12595 | | | | | 12600 | | | | |
| Glu | Lys | Asp | Gly | Ala | Ala | Thr | Gly | Val | Asp | Ala | Ile | Cys | Thr | His |
| 12605 | | | | | 12610 | | | | | 12615 | | | | |
| Arg | Leu | Asp | Pro | Lys | Ser | Pro | Gly | Val | Asp | Arg | Glu | Gln | Leu | Tyr |
| 12620 | | | | | 12625 | | | | | 12630 | | | | |
| Trp | Glu | Leu | Ser | Gln | Leu | Thr | Asn | Gly | Ile | Lys | Glu | Leu | Gly | Pro |
| 12635 | | | | | 12640 | | | | | 12645 | | | | |
| Tyr | Thr | Leu | Asp | Arg | Asn | Ser | Leu | Tyr | Val | Asn | Gly | Phe | Thr | His |
| 12650 | | | | | 12655 | | | | | 12660 | | | | |
| Trp | Ile | Pro | Val | Pro | Thr | Ser | Ser | Thr | Pro | Gly | Thr | Ser | Thr | Val |
| 12665 | | | | | 12670 | | | | | 12675 | | | | |
| Asp | Leu | Gly | Ser | Gly | Thr | Pro | Ser | Ser | Leu | Pro | Ser | Pro | Thr | Thr |
| 12680 | | | | | 12685 | | | | | 12690 | | | | |
| Ala | Gly | Pro | Leu | Leu | Val | Pro | Phe | Thr | Leu | Asn | Phe | Thr | Ile | Thr |
| 12695 | | | | | 12700 | | | | | 12705 | | | | |
| Asn | Leu | Lys | Tyr | Glu | Glu | Asp | Met | His | Cys | Pro | Gly | Ser | Arg | Lys |
| 12710 | | | | | 12715 | | | | | 12720 | | | | |
| Phe | Asn | Thr | Thr | Glu | Arg | Val | Leu | Gln | Ser | Leu | Leu | Gly | Pro | Met |
| 12725 | | | | | 12730 | | | | | 12735 | | | | |
| Phe | Lys | Asn | Thr | Ser | Val | Gly | Pro | Leu | Tyr | Ser | Gly | Cys | Arg | Leu |
| 12740 | | | | | 12745 | | | | | 12750 | | | | |
| Thr | Leu | Leu | Arg | Ser | Glu | Lys | Asp | Gly | Ala | Ala | Thr | Gly | Val | Asp |
| 12755 | | | | | 12760 | | | | | 12765 | | | | |
| Ala | Ile | Cys | Thr | His | Arg | Leu | Asp | Pro | Lys | Ser | Pro | Gly | Val | Asp |
| 12770 | | | | | 12775 | | | | | 12780 | | | | |
| Arg | Glu | Gln | Leu | Tyr | Trp | Glu | Leu | Ser | Gln | Leu | Thr | Asn | Gly | Ile |
| 12785 | | | | | 12790 | | | | | 12795 | | | | |
| Lys | Glu | Leu | Gly | Pro | Tyr | Thr | Leu | Asp | Arg | Asn | Ser | Leu | Tyr | Val |
| 12800 | | | | | 12805 | | | | | 12810 | | | | |
| Asn | Gly | Phe | Thr | His | Gln | Thr | Ser | Ala | Pro | Asn | Thr | Ser | Thr | Pro |
| 12815 | | | | | 12820 | | | | | 12825 | | | | |
| Gly | Thr | Ser | Thr | Val | Asp | Leu | Gly | Thr | Ser | Gly | Thr | Pro | Ser | Ser |
| 12830 | | | | | 12835 | | | | | 12840 | | | | |
| Leu | Pro | Ser | Pro | Thr | Ser | Ala | Gly | Pro | Leu | Leu | Val | Pro | Phe | Thr |
| 12845 | | | | | 12850 | | | | | 12855 | | | | |
| Leu | Asn | Phe | Thr | Ile | Thr | Asn | Leu | Gln | Tyr | Glu | Glu | Asp | Met | His |
| 12860 | | | | | 12865 | | | | | 12870 | | | | |

```
His Pro Gly Ser Arg Lys Phe Asn Thr Thr Glu Arg Val Leu Gln
    12875               12880               12885

Gly Leu Leu Gly Pro Met Phe Lys Asn Thr Ser Val Gly Leu Leu
    12890               12895               12900

Tyr Ser Gly Cys Arg Leu Thr Leu Leu Arg Pro Glu Lys Asn Gly
    12905               12910               12915

Ala Ala Thr Gly Met Asp Ala Ile Cys Ser His Arg Leu Asp Pro
    12920               12925               12930

Lys Ser Pro Gly Leu Asn Arg Glu Gln Leu Tyr Trp Glu Leu Ser
    12935               12940               12945

Gln Leu Thr His Gly Ile Lys Glu Leu Gly Pro Tyr Thr Leu Asp
    12950               12955               12960

Arg Asn Ser Leu Tyr Val Asn Gly Phe Thr His Arg Ser Ser Val
    12965               12970               12975

Ala Pro Thr Ser Thr Pro Gly Thr Ser Thr Val Asp Leu Gly Thr
    12980               12985               12990

Ser Gly Thr Pro Ser Ser Leu Pro Ser Pro Thr Thr Ala Val Pro
    12995               13000               13005

Leu Leu Val Pro Phe Thr Leu Asn Phe Thr Ile Thr Asn Leu Gln
    13010               13015               13020

Tyr Gly Glu Asp Met Arg His Pro Gly Ser Arg Lys Phe Asn Thr
    13025               13030               13035

Thr Glu Arg Val Leu Gln Gly Leu Leu Gly Pro Leu Phe Lys Asn
    13040               13045               13050

Ser Ser Val Gly Pro Leu Tyr Ser Gly Cys Arg Leu Ile Ser Leu
    13055               13060               13065

Arg Ser Glu Lys Asp Gly Ala Ala Thr Gly Val Asp Ala Ile Cys
    13070               13075               13080

Thr His His Leu Asn Pro Gln Ser Pro Gly Leu Asp Arg Glu Gln
    13085               13090               13095

Leu Tyr Trp Gln Leu Ser Gln Met Thr Asn Gly Ile Lys Glu Leu
    13100               13105               13110

Gly Pro Tyr Thr Leu Asp Arg Asn Ser Leu Tyr Val Asn Gly Phe
    13115               13120               13125

Thr His Arg Ser Ser Gly Leu Thr Thr Ser Thr Pro Trp Thr Ser
    13130               13135               13140

Thr Val Asp Leu Gly Thr Ser Gly Thr Pro Ser Pro Val Pro Ser
    13145               13150               13155

Pro Thr Thr Thr Gly Pro Leu Leu Val Pro Phe Thr Leu Asn Phe
    13160               13165               13170

Thr Ile Thr Asn Leu Gln Tyr Glu Glu Asn Met Gly His Pro Gly
    13175               13180               13185

Ser Arg Lys Phe Asn Ile Thr Glu Ser Val Leu Gln Gly Leu Leu
    13190               13195               13200

Lys Pro Leu Phe Lys Ser Thr Ser Val Gly Pro Leu Tyr Ser Gly
    13205               13210               13215

Cys Arg Leu Thr Leu Leu Arg Pro Glu Lys Asp Gly Val Ala Thr
    13220               13225               13230

Arg Val Asp Ala Ile Cys Thr His Arg Pro Asp Pro Lys Ile Pro
    13235               13240               13245

Gly Leu Asp Arg Gln Gln Leu Tyr Trp Glu Leu Ser Gln Leu Thr
    13250               13255               13260
```

```
His Ser Ile Thr Glu Leu Gly Pro Tyr Thr Leu Asp Arg Asp Ser
    13265               13270                   13275

Leu Tyr Val Asn Gly Phe Thr Gln Arg Ser Ser Val Pro Thr Thr
    13280               13285                   13290

Ser Thr Pro Gly Thr Phe Thr Val Gln Pro Glu Thr Ser Glu Thr
    13295               13300                   13305

Pro Ser Ser Leu Pro Gly Pro Thr Ala Thr Gly Pro Val Leu Leu
    13310               13315                   13320

Pro Phe Thr Leu Asn Phe Thr Ile Thr Asn Leu Gln Tyr Glu Glu
    13325               13330                   13335

Asp Met Arg Arg Pro Gly Ser Arg Lys Phe Asn Thr Thr Glu Arg
    13340               13345                   13350

Val Leu Gln Gly Leu Leu Met Pro Leu Phe Lys Asn Thr Ser Val
    13355               13360                   13365

Ser Ser Leu Tyr Ser Gly Cys Arg Leu Thr Leu Leu Arg Pro Glu
    13370               13375                   13380

Lys Asp Gly Ala Ala Thr Arg Val Asp Ala Val Cys Thr His Arg
    13385               13390                   13395

Pro Asp Pro Lys Ser Pro Gly Leu Asp Arg Glu Arg Leu Tyr Trp
    13400               13405                   13410

Lys Leu Ser Gln Leu Thr His Gly Ile Thr Glu Leu Gly Pro Tyr
    13415               13420                   13425

Thr Leu Asp Arg His Ser Leu Tyr Val Asn Gly Phe Thr His Gln
    13430               13435                   13440

Ser Ser Met Thr Thr Thr Arg Thr Pro Asp Thr Ser Thr Met His
    13445               13450                   13455

Leu Ala Thr Ser Arg Thr Pro Ala Ser Leu Ser Gly Pro Met Thr
    13460               13465                   13470

Ala Ser Pro Leu Leu Val Leu Phe Thr Ile Asn Phe Thr Ile Thr
    13475               13480                   13485

Asn Leu Arg Tyr Glu Glu Asn Met His His Pro Gly Ser Arg Lys
    13490               13495                   13500

Phe Asn Thr Thr Glu Arg Val Leu Gln Gly Leu Leu Arg Pro Val
    13505               13510                   13515

Phe Lys Asn Thr Ser Val Gly Pro Leu Tyr Ser Gly Cys Arg Leu
    13520               13525                   13530

Thr Leu Leu Arg Pro Lys Lys Asp Gly Ala Ala Thr Lys Val Asp
    13535               13540                   13545

Ala Ile Cys Thr Tyr Arg Pro Asp Pro Lys Ser Pro Gly Leu Asp
    13550               13555                   13560

Arg Glu Gln Leu Tyr Trp Glu Leu Ser Gln Leu Thr His Ser Ile
    13565               13570                   13575

Thr Glu Leu Gly Pro Tyr Thr Leu Asp Arg Asp Ser Leu Tyr Val
    13580               13585                   13590

Asn Gly Phe Thr Gln Arg Ser Ser Val Pro Thr Thr Ser Ile Pro
    13595               13600                   13605

Gly Thr Pro Thr Val Asp Leu Gly Thr Ser Gly Thr Pro Val Ser
    13610               13615                   13620

Lys Pro Gly Pro Ser Ala Ala Ser Pro Leu Leu Val Leu Phe Thr
    13625               13630                   13635

Leu Asn Phe Thr Ile Thr Asn Leu Arg Tyr Glu Glu Asn Met Gln
    13640               13645                   13650
```

-continued

| | | | | | | | | | | | |
|---|---|---|---|---|---|---|---|---|---|---|---|
| His | Pro | Gly | Ser | Arg | Lys | Phe | Asn | Thr | Thr | Glu | Arg | Val | Leu | Gln |
| 13655 | | | | | 13660 | | | | | 13665 | | | | |
| Gly | Leu | Leu | Arg | Ser | Leu | Phe | Lys | Ser | Thr | Ser | Val | Gly | Pro | Leu |
| 13670 | | | | | 13675 | | | | | 13680 | | | | |
| Tyr | Ser | Gly | Cys | Arg | Leu | Thr | Leu | Leu | Arg | Pro | Glu | Lys | Asp | Gly |
| 13685 | | | | | 13690 | | | | | 13695 | | | | |
| Thr | Ala | Thr | Gly | Val | Asp | Ala | Ile | Cys | Thr | His | His | Pro | Asp | Pro |
| 13700 | | | | | 13705 | | | | | 13710 | | | | |
| Lys | Ser | Pro | Arg | Leu | Asp | Arg | Glu | Gln | Leu | Tyr | Trp | Glu | Leu | Ser |
| 13715 | | | | | 13720 | | | | | 13725 | | | | |
| Gln | Leu | Thr | His | Asn | Ile | Thr | Glu | Leu | Gly | Pro | Tyr | Ala | Leu | Asp |
| 13730 | | | | | 13735 | | | | | 13740 | | | | |
| Asn | Asp | Ser | Leu | Phe | Val | Asn | Gly | Phe | Thr | His | Arg | Ser | Ser | Val |
| 13745 | | | | | 13750 | | | | | 13755 | | | | |
| Ser | Thr | Thr | Ser | Thr | Pro | Gly | Thr | Pro | Thr | Val | Tyr | Leu | Gly | Ala |
| 13760 | | | | | 13765 | | | | | 13770 | | | | |
| Ser | Lys | Thr | Pro | Ala | Ser | Ile | Phe | Gly | Pro | Ser | Ala | Ala | Ser | His |
| 13775 | | | | | 13780 | | | | | 13785 | | | | |
| Leu | Leu | Ile | Leu | Phe | Thr | Leu | Asn | Phe | Thr | Ile | Thr | Asn | Leu | Arg |
| 13790 | | | | | 13795 | | | | | 13800 | | | | |
| Tyr | Glu | Glu | Asn | Met | Trp | Pro | Gly | Ser | Arg | Lys | Phe | Asn | Thr | Thr |
| 13805 | | | | | 13810 | | | | | 13815 | | | | |
| Glu | Arg | Val | Leu | Gln | Gly | Leu | Leu | Arg | Pro | Leu | Phe | Lys | Asn | Thr |
| 13820 | | | | | 13825 | | | | | 13830 | | | | |
| Ser | Val | Gly | Pro | Leu | Tyr | Ser | Gly | Cys | Arg | Leu | Thr | Leu | Leu | Arg |
| 13835 | | | | | 13840 | | | | | 13845 | | | | |
| Pro | Glu | Lys | Asp | Gly | Glu | Ala | Thr | Gly | Val | Asp | Ala | Ile | Cys | Thr |
| 13850 | | | | | 13855 | | | | | 13860 | | | | |
| His | Arg | Pro | Asp | Pro | Thr | Gly | Pro | Gly | Leu | Asp | Arg | Glu | Gln | Leu |
| 13865 | | | | | 13870 | | | | | 13875 | | | | |
| Tyr | Leu | Glu | Leu | Ser | Gln | Leu | Thr | His | Ser | Ile | Thr | Glu | Leu | Gly |
| 13880 | | | | | 13885 | | | | | 13890 | | | | |
| Pro | Tyr | Thr | Leu | Asp | Arg | Asp | Ser | Leu | Tyr | Val | Asn | Gly | Phe | Thr |
| 13895 | | | | | 13900 | | | | | 13905 | | | | |
| His | Arg | Ser | Ser | Val | Pro | Thr | Thr | Ser | Thr | Gly | Val | Val | Ser | Glu |
| 13910 | | | | | 13915 | | | | | 13920 | | | | |
| Glu | Pro | Phe | Thr | Leu | Asn | Phe | Thr | Ile | Asn | Asn | Leu | Arg | Tyr | Met |
| 13925 | | | | | 13930 | | | | | 13935 | | | | |
| Ala | Asp | Met | Gly | Gln | Pro | Gly | Ser | Leu | Lys | Phe | Asn | Ile | Thr | Asp |
| 13940 | | | | | 13945 | | | | | 13950 | | | | |
| Asn | Val | Met | Gln | His | Leu | Leu | Ser | Pro | Leu | Phe | Gln | Arg | Ser | Ser |
| 13955 | | | | | 13960 | | | | | 13965 | | | | |
| Leu | Gly | Ala | Arg | Tyr | Thr | Gly | Cys | Arg | Val | Ile | Ala | Leu | Arg | Ser |
| 13970 | | | | | 13975 | | | | | 13980 | | | | |
| Val | Lys | Asn | Gly | Ala | Glu | Thr | Arg | Val | Asp | Leu | Leu | Cys | Thr | Tyr |
| 13985 | | | | | 13990 | | | | | 13995 | | | | |
| Leu | Gln | Pro | Leu | Ser | Gly | Pro | Gly | Leu | Pro | Ile | Lys | Gln | Val | Phe |
| 14000 | | | | | 14005 | | | | | 14010 | | | | |
| His | Glu | Leu | Ser | Gln | Gln | Thr | His | Gly | Ile | Thr | Arg | Leu | Gly | Pro |
| 14015 | | | | | 14020 | | | | | 14025 | | | | |
| Tyr | Ser | Leu | Asp | Lys | Asp | Ser | Leu | Tyr | Leu | Asn | Gly | Tyr | Asn | Glu |
| 14030 | | | | | 14035 | | | | | 14040 | | | | |

```
Pro Gly  Pro Asp Glu Pro Pro  Thr Thr Pro Lys Pro  Ala Thr Thr
    14045            14050                14055

Phe Leu  Pro Pro Leu Ser Glu  Ala Thr Thr Ala Met  Gly Tyr His
    14060            14065                14070

Leu Lys  Thr Leu Thr Leu Asn  Phe Thr Ile Ser Asn  Leu Gln Tyr
    14075            14080                14085

Ser Pro  Asp Met Gly Lys Gly  Ser Ala Thr Phe Asn  Ser Thr Glu
    14090            14095                14100

Gly Val  Leu Gln His Leu Leu  Arg Pro Leu Phe Gln  Lys Ser Ser
    14105            14110                14115

Met Gly  Pro Phe Tyr Leu Gly  Cys Gln Leu Ile Ser  Leu Arg Pro
    14120            14125                14130

Glu Lys  Asp Gly Ala Ala Thr  Gly Val Asp Thr Thr  Cys Thr Tyr
    14135            14140                14145

His Pro  Asp Pro Val Gly Pro  Gly Leu Asp Ile Gln  Gln Leu Tyr
    14150            14155                14160

Trp Glu  Leu Ser Gln Leu Thr  His Gly Val Thr Gln  Leu Gly Phe
    14165            14170                14175

Tyr Val  Leu Asp Arg Asp Ser  Leu Phe Ile Asn Gly  Tyr Ala Pro
    14180            14185                14190

Gln Asn  Leu Ser Ile Arg Gly  Glu Tyr Gln Ile Asn  Phe His Ile
    14195            14200                14205

Val Asn  Trp Asn Leu Ser Asn  Pro Asp Pro Thr Ser  Ser Glu Tyr
    14210            14215                14220

Ile Thr  Leu Leu Arg Asp Ile  Gln Asp Lys Val Thr  Thr Leu Tyr
    14225            14230                14235

Lys Gly  Ser Gln Leu His Asp  Thr Phe Arg Phe Cys  Leu Val Thr
    14240            14245                14250

Asn Leu  Thr Met Asp Ser Val  Leu Val Thr Val Lys  Ala Leu Phe
    14255            14260                14265

Ser Ser  Asn Leu Asp Pro Ser  Leu Val Glu Gln Val  Phe Leu Asp
    14270            14275                14280

Lys Thr  Leu Asn Ala Ser Phe  His Trp Leu Gly Ser  Thr Tyr Gln
    14285            14290                14295

Leu Val  Asp Ile His Val Thr  Glu Met Glu Ser Ser  Val Tyr Gln
    14300            14305                14310

Pro Thr  Ser Ser Ser Ser Thr  Gln His Phe Tyr Leu  Asn Phe Thr
    14315            14320                14325

Ile Thr  Asn Leu Pro Tyr Ser  Gln Asp Lys Ala Gln  Pro Gly Thr
    14330            14335                14340

Thr Asn  Tyr Gln Arg Asn Lys  Arg Asn Ile Glu Asp  Ala Leu Asn
    14345            14350                14355

Gln Leu  Phe Arg Asn Ser Ser  Ile Lys Ser Tyr Phe  Ser Asp Cys
    14360            14365                14370

Gln Val  Ser Thr Phe Arg Ser  Val Pro Asn Arg His  His Thr Gly
    14375            14380                14385

Val Asp  Ser Leu Cys Asn Phe  Ser Pro Leu Ala Arg  Arg Val Asp
    14390            14395                14400

Arg Val  Ala Ile Tyr Glu Glu  Phe Leu Arg Met Thr  Arg Asn Gly
    14405            14410                14415

Thr Gln  Leu Gln Asn Phe Thr  Leu Asp Arg Ser Ser  Val Leu Val
    14420            14425                14430
```

Asp Gly Tyr Ser Pro Asn Arg Asn Glu Pro Leu Thr Gly Asn Ser
    14435           14440               14445

Asp Leu Pro Phe Trp Ala Val Ile Leu Ile Gly Leu Ala Gly Leu
    14450           14455               14460

Leu Gly Val Ile Thr Cys Leu Ile Cys Gly Val Leu Val Thr Thr
    14465           14470               14475

Arg Arg Arg Lys Lys Glu Gly Glu Tyr Asn Val Gln Gln Gln Cys
    14480           14485               14490

Pro Gly Tyr Tyr Gln Ser His Leu Asp Leu Glu Asp Leu Gln
    14495           14500               14505

<210> SEQ ID NO 9
<211> LENGTH: 490
<212> TYPE: PRT
<213> ORGANISM: Homo sapiens
<220> FEATURE:
<223> OTHER INFORMATION: human STEAP2 (STAMP1) Protein

<400> SEQUENCE: 9

Met Glu Ser Ile Ser Met Met Gly Ser Pro Lys Ser Leu Ser Glu Thr
1               5                   10                  15

Phe Leu Pro Asn Gly Ile Asn Gly Ile Lys Asp Ala Arg Lys Val Thr
            20                  25                  30

Val Gly Val Ile Gly Ser Gly Asp Phe Ala Lys Ser Leu Thr Ile Arg
        35                  40                  45

Leu Ile Arg Cys Gly Tyr His Val Val Ile Gly Ser Arg Asn Pro Lys
    50                  55                  60

Phe Ala Ser Glu Phe Phe Pro His Val Val Asp Val Thr His His Glu
65                  70                  75                  80

Asp Ala Leu Thr Lys Thr Asn Ile Ile Phe Val Ala Ile His Arg Glu
                85                  90                  95

His Tyr Thr Ser Leu Trp Asp Leu Arg His Leu Leu Val Gly Lys Ile
            100                 105                 110

Leu Ile Asp Val Ser Asn Asn Met Arg Ile Asn Gln Tyr Pro Glu Ser
        115                 120                 125

Asn Ala Glu Tyr Leu Ala Ser Leu Phe Pro Asp Ser Leu Ile Val Lys
    130                 135                 140

Gly Phe Asn Val Val Ser Ala Trp Ala Leu Gln Leu Gly Pro Lys Asp
145                 150                 155                 160

Ala Ser Arg Gln Val Tyr Ile Cys Ser Asn Asn Ile Gln Ala Arg Gln
                165                 170                 175

Gln Val Ile Glu Leu Ala Arg Gln Leu Asn Phe Ile Pro Ile Asp Leu
            180                 185                 190

Gly Ser Leu Ser Ser Ala Arg Glu Ile Glu Asn Leu Pro Leu Arg Leu
        195                 200                 205

Phe Thr Leu Trp Arg Gly Pro Val Val Ala Ile Ser Leu Ala Thr
    210                 215                 220

Phe Phe Phe Leu Tyr Ser Phe Val Arg Asp Val Ile His Pro Tyr Ala
225                 230                 235                 240

Arg Asn Gln Gln Ser Asp Phe Tyr Lys Ile Pro Ile Glu Ile Val Asn
                245                 250                 255

Lys Thr Leu Pro Ile Val Ala Ile Thr Leu Leu Ser Leu Val Tyr Leu
            260                 265                 270

Ala Gly Leu Leu Ala Ala Ala Tyr Gln Leu Tyr Tyr Gly Thr Lys Tyr
        275                 280                 285

Arg Arg Phe Pro Pro Trp Leu Glu Thr Trp Leu Gln Cys Arg Lys Gln
290                 295                 300

Leu Gly Leu Leu Ser Phe Phe Ala Met Val His Val Ala Tyr Ser
305                 310                 315                 320

Leu Cys Leu Pro Met Arg Arg Ser Glu Arg Tyr Leu Phe Leu Asn Met
                325                 330                 335

Ala Tyr Gln Gln Val His Ala Asn Ile Glu Asn Ser Trp Asn Glu Glu
                340                 345                 350

Glu Val Trp Arg Ile Glu Met Tyr Ile Ser Phe Gly Ile Met Ser Leu
                355                 360                 365

Gly Leu Leu Ser Leu Leu Ala Val Thr Ser Ile Pro Ser Val Ser Asn
370                 375                 380

Ala Leu Asn Trp Arg Glu Phe Ser Phe Ile Gln Ser Thr Leu Gly Tyr
385                 390                 395                 400

Val Ala Leu Leu Ile Ser Thr Phe His Val Leu Ile Tyr Gly Trp Lys
                405                 410                 415

Arg Ala Phe Glu Glu Tyr Tyr Arg Phe Tyr Thr Pro Pro Asn Phe
                420                 425                 430

Val Leu Ala Leu Val Leu Pro Ser Ile Val Ile Leu Gly Lys Ile Ile
                435                 440                 445

Leu Phe Leu Pro Cys Ile Ser Arg Lys Leu Arg Ile Lys Lys Gly
450                 455                 460

Trp Glu Lys Ser Gln Phe Leu Glu Glu Gly Met Gly Gly Thr Ile Pro
465                 470                 475                 480

His Val Ser Pro Glu Arg Val Thr Val Met
                485                 490

<210> SEQ ID NO 10
<211> LENGTH: 453
<212> TYPE: PRT
<213> ORGANISM: Artificial Sequence
<220> FEATURE:
<223> OTHER INFORMATION: Anti-CD20 REGN1979 Heavy Chain

<400> SEQUENCE: 10

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asn Asp Tyr
                20                  25                  30

Ala Met His Trp Val Arg Gln Ala Pro Gly Lys Gly Leu Glu Trp Val
            35                  40                  45

Ser Val Ile Ser Trp Asn Ser Asp Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met His Ser Leu Arg Ala Glu Asp Thr Ala Leu Tyr Tyr Cys
                85                  90                  95

Ala Lys Asp Asn His Tyr Gly Ser Gly Ser Tyr Tyr Tyr Gln Tyr
                100                 105                 110

Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Cys Ser Arg Ser
        130                 135                 140

Thr Ser Glu Ser Thr Ala Ala Leu Gly Cys Leu Val Lys Asp Tyr Phe
145                 150                 155                 160

```
Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
        180                 185                 190

Ser Ser Val Val Thr Val Pro Ser Ser Ser Leu Gly Thr Lys Thr Tyr
            195                 200                 205

Thr Cys Asn Val Asp His Lys Pro Ser Asn Thr Lys Val Asp Lys Arg
        210                 215                 220

Val Glu Ser Lys Tyr Gly Pro Pro Cys Pro Cys Pro Ala Pro Pro
225                 230                 235                 240

Val Ala Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
                420                 425                 430

Val Met His Glu Ala Leu His Asn His Tyr Thr Gln Lys Ser Leu Ser
            435                 440                 445

Leu Ser Leu Gly Lys
        450

<210> SEQ ID NO 11
<211> LENGTH: 449
<212> TYPE: PRT
<213> ORGANISM: Artificial Sequence
<220> FEATURE:
<223> OTHER INFORMATION: Anti-CD3 REGN1979 Heavy Chain

<400> SEQUENCE: 11

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60
```

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
            85                  90                  95

Ala Lys Asp Asn Ser Gly Tyr Gly His Tyr Tyr Tyr Gly Met Asp Val
            100                 105                 110

Trp Gly Gln Gly Thr Thr Val Thr Val Ala Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
            210                 215                 220

Tyr Gly Pro Pro Cys Pro Pro Cys Pro Ala Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
            420                 425                 430

Ala Leu His Asn Arg Phe Thr Gln Lys Ser Leu Ser Leu Ser Leu Gly
            435                 440                 445

Lys

<210> SEQ ID NO 12
<211> LENGTH: 214
<212> TYPE: PRT
<213> ORGANISM: Artificial Sequence
<220> FEATURE:
<223> OTHER INFORMATION: Common REGN1979 Light Chain

<400> SEQUENCE: 12

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Ile Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 127
<212> TYPE: PRT
<213> ORGANISM: Artificial Sequence
<220> FEATURE:
<223> OTHER INFORMATION: Anti-CD20 REGN1979 HCVR

<400> SEQUENCE: 13

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Val Ile Ser Trp Asn Ser Asp Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met His Ser Leu Arg Ala Glu Asp Thr Ala Leu Tyr Tyr Cys
                85                  90                  95

Ala Lys Asp Asn His Tyr Gly Ser Gly Ser Tyr Tyr Tyr Gln Tyr
            100                 105                 110

```
Gly Met Asp Val Trp Gly Gln Gly Thr Thr Val Thr Val Ser Ser
            115                 120                 125

<210> SEQ ID NO 14
<211> LENGTH: 123
<212> TYPE: PRT
<213> ORGANISM: Artificial Sequence
<220> FEATURE:
<223> OTHER INFORMATION: Anti-CD3 REGN1979 HCVR

<400> SEQUENCE: 14

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Asn Ser Gly Tyr Gly His Tyr Tyr Tyr Gly Met Asp Val
            100                 105                 110

Trp Gly Gln Gly Thr Thr Val Thr Val Ala Ser
        115                 120

<210> SEQ ID NO 15
<211> LENGTH: 108
<212> TYPE: PRT
<213> ORGANISM: Artificial Sequence
<220> FEATURE:
<223> OTHER INFORMATION: Common REGN1979 LCVR

<400> SEQUENCE: 15

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Ile Asn Trp Pro Leu
                85                  90                  95

Thr Phe Gly Gly Gly Thr Lys Val Glu Ile Lys Arg
            100                 105

<210> SEQ ID NO 16
<211> LENGTH: 8
<212> TYPE: PRT
<213> ORGANISM: Artificial Sequence
<220> FEATURE:
<223> OTHER INFORMATION: Anti-CD20 REGN1979 HCDR1
```

<400> SEQUENCE: 16

Gly Phe Thr Phe Asn Asp Tyr Ala
1               5

<210> SEQ ID NO 17
<211> LENGTH: 8
<212> TYPE: PRT
<213> ORGANISM: Artificial Sequence
<220> FEATURE:
<223> OTHER INFORMATION: Anti-CD20 REGN1979 HCDR2

<400> SEQUENCE: 17

Ile Ser Trp Asn Ser Asp Ser Ile
1               5

<210> SEQ ID NO 18
<211> LENGTH: 20
<212> TYPE: PRT
<213> ORGANISM: Artificial Sequence
<220> FEATURE:
<223> OTHER INFORMATION: Anti-CD20 REGN1979 HCDR3

<400> SEQUENCE: 18

Ala Lys Asp Asn His Tyr Gly Ser Gly Ser Tyr Tyr Tyr Gln Tyr
1               5                   10                  15

Gly Met Asp Val
            20

<210> SEQ ID NO 19
<211> LENGTH: 8
<212> TYPE: PRT
<213> ORGANISM: Artificial Sequence
<220> FEATURE:
<223> OTHER INFORMATION: Anti-CD3 REGN1979 HCDR1

<400> SEQUENCE: 19

Gly Phe Thr Phe Asp Asp Tyr Thr
1               5

<210> SEQ ID NO 20
<211> LENGTH: 8
<212> TYPE: PRT
<213> ORGANISM: Artificial Sequence
<220> FEATURE:
<223> OTHER INFORMATION: Anti-CD3 REGN1979 HCDR2

<400> SEQUENCE: 20

Ile Ser Trp Asn Ser Gly Ser Ile
1               5

<210> SEQ ID NO 21
<211> LENGTH: 16
<212> TYPE: PRT
<213> ORGANISM: Artificial Sequence
<220> FEATURE:
<223> OTHER INFORMATION: Anti-CD3 REGN1979 HCDR3

<400> SEQUENCE: 21

Ala Lys Asp Asn Ser Gly Tyr Gly His Tyr Tyr Tyr Gly Met Asp Val
1               5                   10                  15

<210> SEQ ID NO 22
<211> LENGTH: 6
<212> TYPE: PRT
<213> ORGANISM: Artificial Sequence

```
<220> FEATURE:
<223> OTHER INFORMATION: Common REGN1979 LCDR1

<400> SEQUENCE: 22

Gln Ser Val Ser Ser Asn
1               5

<210> SEQ ID NO 23
<211> LENGTH: 3
<212> TYPE: PRT
<213> ORGANISM: Artificial Sequence
<220> FEATURE:
<223> OTHER INFORMATION: Common REGN1979 LCDR2

<400> SEQUENCE: 23

Gly Ala Ser
1

<210> SEQ ID NO 24
<211> LENGTH: 9
<212> TYPE: PRT
<213> ORGANISM: Artificial Sequence
<220> FEATURE:
<223> OTHER INFORMATION: Common REGN1979 LCDR3

<400> SEQUENCE: 24

Gln His Tyr Ile Asn Trp Pro Leu Thr
1               5
```

DOSING STRATEGY THAT MITIGATES CYTOKINE RELEASE SYNDROME FOR THERAPEUTIC ANTIBODIES

CROSS-REFERENCE TO RELATED APPLICATIONS

This application claims the benefit under 35 USC § 119(e) of U.S. Provisional Application Nos. 62/726,137, filed Aug. 31, 2018; 62/774,019, filed Nov. 30, 2018; and 62/861,100, filed Jun. 13, 2019, each of which is incorporated herein by reference in its entirety for all purposes.

REFERENCE TO A SEQUENCE LISTING

This application incorporates by reference the Sequence Listing submitted in Computer Readable Form as file 10496-Substitute Sequence, created on Dec. 5, 2019 and containing 162,988 bytes.

FIELD OF THE INVENTION

The present invention lies in the field of medicine, and relates to dosing strategies and administration regimens for therapeutic antibodies (e.g., bispecific antibodies targeting T cells) that mitigate the prevalence and severity of cytokine release syndrome or an infusion-related reaction in patients undergoing immunotherapy.

BACKGROUND

Cytokine release syndrome (CRS) is a systemic inflammatory response that can be triggered by a variety of factors, including certain drugs. T cell-activating cancer immunotherapies carry a particularly high risk of CRS, which is usually due to on-target effects induced by binding of a bispecific antibody or chimeric antigen receptor (CAR) T cell to its antigen and subsequent activation of bystander immune cells and non-immune cells, such as endothelial cells. Activation of the bystander cells results in the massive release of a range of cytokines. IL-6, IL-10, and interferon (IFN)-$\gamma$ are among the core cytokines that are consistently found to be elevated in serum of patients with CRS. With T cell-activating therapies directed against tumor cells, CRS is triggered by the massive release of IFN-$\gamma$ by activated T cells or the tumor cells themselves. Secreted IFN-$\gamma$ induces activation of other immune cells, most importantly macrophages, which in turn produce excessive amounts of additional cytokines such as IL-6, TNF-$\alpha$, and IL-10. IL-6, in particular, contributes to many of the key symptoms of CRS, including vascular leakage, and activation of the complement and coagulation cascade inducing disseminated intravascular coagulation. In addition, IL-6 likely contributes to cardiomyopathy by promoting myocardial dysfunction. Shimabukaro-Vornhagen et al., *Journal for Immunotherapy of Cancer*, 6:56, pp. 1-14, 2018. In some cases, the symptoms associated with CRS are termed infusion-related reaction (IRR) if they occur less than six hours following the start of infusion, and CRS if they occur from six hours onward following the start of infusion.

The management of the toxicities of cancer immunotherapy is a challenging clinical problem. Mitigating CRS or IRR is a hallmark of administering certain treatment modalities, for example CAR T cells and bispecific antibodies targeting T cells. Low grade CRS is generally treated symptomatically with anti-histamines, antipyretics and fluids. Severe CRS can represent a life-threatening adverse event that requires prompt and aggressive treatment. Reduction of tumor burden, limitations on the dose of administered therapy, and premedication with steroids have reduced the incidence of severe CRS, as have the use of anti-cytokine treatments. Tocilizumab, an anti-IL-6 antibody, has become a standard initial treatment for severe CRS in some circumstances. However, the use of dose limitations and treatments to minimize cytokine activity can have detrimental effects on the efficacy of the immunotherapy. Thus, there remains a need for alternative strategies to mitigate the potential life-threatening effects of CRS without negatively impacting the therapeutic benefits of immunotherapies.

BRIEF SUMMARY OF THE INVENTION

In one aspect, the present invention provides a method of administering a therapeutic protein to a subject in a dosing regimen to mitigate adverse effects of cytokine release syndrome or infusion-related reaction, comprising: (i) administering fractions of a primary dose (D1) of the therapeutic protein in week 1 of the dosing regimen, wherein the primary dose comprises no more than 10 mg of the therapeutic protein, a first dose fraction (F1D1) comprises 40% to 60% of the total primary dose and is administered to the subject on day 1 of week 1, and a second dose fraction (F2D1) comprises the remaining 40% to 60% of the total primary dose and is administered to the subject from 12 to 96 hours following administration of the F1D1; (ii) administering fractions of a secondary dose (D2) of the therapeutic protein in week 2 of the dosing regimen, wherein the secondary dose is no more than one-half of a maximum weekly dose of the therapeutic protein, a first dose fraction (F1D2) comprises 40% to 60% of the total secondary dose, a second dose fraction (F2D2) comprises the remaining 40% to 60% of the total secondary dose, and the F2D2 is administered to the subject from 12 to 96 hours following administration of the F1D2 during week 2 of the dosing regimen; and (iii) administering the maximum weekly dose of the therapeutic protein to the subject as a single dose in a subsequent week of the dosing regimen.

In some cases, the F2D1 is administered to the subject from 24 to 96 hours following administration of the F1D1. In some cases, the F2D1 is administered to the subject from 18 to 72 hours following administration of the F1D1. In some cases, the F2D2 is administered to the subject from 24 to 96 hours following administration of the F1D2. In some cases, the F2D2 is administered to the subject from 18 to 72 hours following administration of the F1D2. In some cases, the subsequent week is week 3 of the dosing regimen. In some cases, the subsequent week is week 4 of the dosing regimen. In some cases, the subsequent week is week 14 of the dosing regimen. In some cases, the subsequent week is any one of weeks 4 to 36 of the dosing regimen.

In some embodiments, the method further comprises: (i) administering fractions of a tertiary dose (D3) of the therapeutic protein in week 3 of the dosing regimen, wherein the tertiary dose is no less than one-half of the maximum weekly dose of the therapeutic protein and no more than the maximum weekly dose of the therapeutic protein, a first dose fraction (F1D3) comprises 40% to 60% of the total tertiary dose, a second dose fraction (F2D3) comprises the remaining 40% to 60% of the total tertiary dose, and the F2D3 is administered to the subject from 12 to 96 hours following administration of the F1D3 during week 3 of the dosing regimen; and (ii) administering the maximum weekly dose of the therapeutic protein to the subject as a single dose in a subsequent week of the dosing regimen.

In some cases, the F2D3 is administered to the subject from 24 to 96 hours following administration of the F1D3. In some cases, the F2D3 is administered to the subject from 18 to 72 hours following administration of the F1D3.

In some cases, the subsequent week is week 4 of the dosing regimen. In some cases, the subsequent week is week 14 of the dosing regimen. In some cases, the subsequent week is any one of weeks 4 to 36 of the dosing regimen. In various embodiments, the tertiary dose is administered as a single dose in weeks 4 to 12 of the dosing regimen.

In one aspect, the present invention provides a method of administering a therapeutic protein to a subject in a dosing regimen to mitigate adverse effects of cytokine release syndrome or infusion-related reaction, comprising: (i) administering fractions of a primary dose (D1) of the therapeutic protein in week 1 of the dosing regimen, wherein the primary dose comprises no more than 10 mg of the therapeutic protein, a first dose fraction (F1D1) comprises 40% to 60% of the total primary dose and is administered to the subject on day 1 of week 1, and a second dose fraction (F2D1) comprises the remaining 40% to 60% of the total primary dose and is administered to the subject from 12 to 96 hours following administration of the F1D1; (ii) administering fractions of a secondary dose (D2) of the therapeutic protein in week 2 of the dosing regimen, wherein the secondary dose is equal to a maximum weekly dose of the therapeutic protein, a first dose fraction (F1D2) comprises 50% of the total secondary dose, a second dose fraction (F2D2) comprises 50% of the total secondary dose, and the F2D2 is administered to the subject from 12 to 96 hours following administration of the F1D2 during week 2 of the dosing regimen; and (iii) administering the maximum weekly dose of the therapeutic protein to the subject as a single dose in a subsequent week of the dosing regimen.

In one aspect, the present invention provides a method of administering a therapeutic protein to a subject in a dosing regimen to mitigate adverse effects of cytokine release syndrome or infusion-related reaction, comprising: (i) administering fractions of a primary dose (D1) of the therapeutic protein in week 1 of the dosing regimen, wherein the primary dose comprises no more than 10 mg of the therapeutic protein, wherein D1 is administered to the subject in multiple dose fractions (e.g., F1D1, F2D1, F3D1, F4D1, F5D1) on subsequent days within week 1; (ii) administering fractions of a secondary dose (D2) of the therapeutic protein in week 2 of the dosing regimen, wherein the secondary dose is equal to or less than a maximum weekly dose of the therapeutic protein, and is administered in multiple fractions (e.g., F1D2, F2D2, F3D2, F4D2, F5D2) to the subject on subsequent days within week 2; and (iii) administering the maximum weekly dose (MD) of the therapeutic protein to the subject as multiple fractions of MD or as a single dose in a subsequent week of the dosing regimen.

In some embodiments, a second dose fraction (F2) is administered to the subject from 12 to 96 (e.g. 24 to 72) hours following administration of the first dose fraction (F1), optionally a third dose fraction (F3) is administered to the subject no less than 24 hours following administration of the second dose fraction (F2), optionally a fourth dose fraction (F4) is administered to the subject no less than 24 hours following administration of the third dose fraction (F3), and optionally a fifth dose fraction (F5) is administered to the subject no less than 24 hours following administration of the fourth dose fraction (F4) during weeks 1, 2 or 3 of the dosing regimen.

In some embodiments, the methods of the present disclosure further comprise administering one or more "maintenance" doses during a maintenance phase of the dosing regimen, which follows completion of a weekly phase of the regimen. In some cases, each maintenance dose is administered 2, 3 or 4 weeks after the immediately preceding dose. In one embodiment, the maintenance dose is the maximum weekly dose of the therapeutic protein administered as a single dose.

In some cases, the maximum weekly dose (MD) of the therapeutic protein is administered to the subject as a single dose for from 1 to 8 weeks, from 1 to 12 weeks, or from 1 to 16 weeks during a weekly phase of the dosing regimen. In some cases, the maximum weekly dose of the therapeutic protein is administered to the subject as a single dose once every two weeks during a maintenance phase of the dosing regimen, which follows completion of a weekly phase of the dosing regimen. In some cases, the maximum weekly dose of the therapeutic protein is administered to the subject as a single dose once every three weeks during a maintenance phase of the dosing regimen, which follows completion of a weekly phase of the dosing regimen. In some cases, the maximum weekly dose of the therapeutic protein is administered to the subject as a single dose once every four weeks during a maintenance phase of the dosing regimen, which follows completion of a weekly phase of the dosing regimen. In some embodiments, the maintenance phase is a period of up to 86 weeks. In some embodiments, the maintenance phase is a period of up to 87 weeks. In some embodiments, the maintenance phase is a period of up to 88 weeks. In some embodiments, the maintenance phase is greater than 86 weeks, greater than 100 weeks, greater than 150 weeks, greater than 200 weeks, or greater than 250 weeks. In some embodiments, the maintenance phase is at least 24 weeks. In some embodiments, the maintenance phase is 24 weeks.

In various embodiments, the primary dose is 1 mg. In various embodiments, the secondary dose is 20 mg. In various embodiments, the tertiary dose is 40 mg. In various embodiments, the tertiary dose is 80 mg. In various embodiments, the tertiary dose is 160 mg. In various embodiments, the tertiary dose is 320 mg.

In various embodiments, the F1D1 comprises 50% of the total primary dose, and the F2D1 comprises 50% of the total primary dose. In various embodiments, the F1D2 comprises 50% of the total secondary dose, and the F2D2 comprises 50% of the total secondary dose. In various embodiments, the F1D3 comprises 50% of the total tertiary dose, and the F2D3 comprises 50% of the total tertiary dose.

In some cases, the maximum weekly dose (MD) of the therapeutic protein is from 5 mg to 320 mg. In various embodiments, the maximum weekly dose of the therapeutic protein is 6-320 mg, 10-320 mg, 5-40 mg, 5-80 mg, 5-160 mg, 12-40 mg, 18-80 mg, 40-80 mg, 80-160 mg, 160-320 mg, 5 mg, 6 mg, 7 mg, 8 mg, 12 mg, 18 mg, 27 mg, 40 mg, 80 mg, 160 mg or 320 mg. In some embodiments, the maximum weekly dose is 80 mg. In some embodiments, the maximum weekly dose is 160 mg. In some embodiments, the maximum weekly dose is 320 mg.

In some cases, maintenance dose of the therapeutic protein is from 5 mg to 320 mg. In various embodiments, the maintenance dose of the therapeutic protein is 6-320 mg, 10-320 mg, 5-40 mg, 5-80 mg, 5-160 mg, 12-40 mg, 18-80 mg, 40-80 mg, 80-160 mg, 160-320 mg, 5 mg, 6 mg, 7 mg, 8 mg, 12 mg, 18 mg, 27 mg, 40 mg, 80 mg, 160 mg or 320 mg. In some embodiments, the maintenance dose is 80 mg. In some embodiments, the maintenance dose is 160 mg. In some embodiments, the maintenance dose is 320 mg.

In some cases, each dose or dose fraction is administered to the subject over a period of from 1 to 6 hours.

In some embodiments, the subject has been diagnosed with a cancer. In some cases, the cancer is a B-cell malignancy. In some cases, the B-cell malignancy is a CD20+ B-cell malignancy. In some cases, the cancer is non-Hodgkin lymphoma, Hodgkin lymphoma, chronic lymphocytic leukemia, acute lymphoblastic leukemia, small lymphocytic lymphoma, diffuse large B-cell lymphoma, follicular lymphoma, mantle cell lymphoma, marginal zone lymphoma, Waldenstrom macroglobulinemia, primary mediastinal B-cell lymphoma, lymphoblastic lymphoma, or Burkitt lymphoma. In some cases, the cancer is selected from pancreatic carcinoma, head and neck cancer, prostate cancer, malignant gliomas, osteosarcoma, colorectal cancer, gastric cancer, malignant mesothelioma, multiple myeloma, ovarian cancer, small cell lung cancer, non-small cell lung cancer, synovial sarcoma, thyroid cancer, breast cancer, melanomaglioma, breast cancer, squamous cell carcinoma, esophageal cancer, clear cell renal cell carcinoma, chromophobe renal cell carcinoma, oncocytoma, transitional cell carcinoma, urothelial carcinoma, bladder adenocarcinoma, or bladder small cell carcinoma. In some embodiments, the subject has been diagnosed with follicular lymphoma (FL). In some cases, the FL is grade 1-3a. In some embodiments, the subject has been diagnosed with diffuse large B-cell lymphoma (DLBCL). In one embodiment, the subject has been diagnosed with relapsed/refractory DLBCL. In some cases, the subject diagnosed with DLBCL has failed prior CAR-T therapy. In some embodiments, the subject has been diagnosed with mantle cell lymphoma (MCL). In some cases, the subject diagnosed with MCL has failed prior Bruton tyrosine kinase (BTK) inhibitor therapy. In some embodiments, the subject has been diagnosed with marginal zone lymphoma (MZL).

In some cases, the subject is a human, a human adult, or a human child (age less than eighteen).

In various embodiments, the therapeutic protein is an antibody or an antigen-binding fragment thereof. In some cases, the antibody is a fully human antibody. In some cases, the antibody is a bispecific antibody or antigen-binding fragment thereof. In some embodiments, the bispecific antibody or antigen-binding fragment comprises a first antigen-binding arm that binds to a T-cell antigen. In some cases, the T-cell antigen is CD3. In some cases, the T-cell antigen is CD28. In some embodiments, the bispecific antibody or antigen-binding fragment comprises a second antigen-binding arm that binds to a tumor cell antigen. In some cases, the tumor cell antigen is selected from the group consisting of AFP, ALK, BAGE proteins, BCMA, BIRC5 (survivin), BIRC7, β-catenin, brc-abl, BRCA1, BORIS, CA9, carbonic anhydrase IX, caspase-8, CALR, CCR5, CD19, CD20 (MS4A1), CD22, CD40, CD70, CDK4, CEA, cyclin-B1, CYP1B1, EGFR, EGFRvIII, ErbB2/Her2, ErbB3, ErbB4, ETV6-AML, EpCAM, EphA2, Fra-1, FOLR1, GAGE proteins (e.g., GAGE-1, -2), GD2, GD3, GloboH, glypican-3, GM3, gp100, Her2, HLA/B-raf, HLA/k-ras, HLA/MAGE-A3, hTERT, LMP2, MAGE proteins (e.g., MAGE-1, -2, -3, -4, -6, and -12), MART-1, mesothelin, ML-IAP, Muc1, Muc2, Muc3, Muc4, Muc5, Muc16 (CA-125), MUM1, NA17, NY-BR1, NY-BR62, NY-BR85, NY-ESO1, p15, p53, PAP, PAX3, PAX5, PCTA-1, PLAC1, PRLR, PRAME, PSMA (FOLH1), RAGE proteins, Ras, RGS5, Rho, SART-1, SART-3, STEAP1, STEAP2, TAG-72, TGF-β, TMPRSS2, Thompson-nouvelle antigen (Tn), TRP-1, TRP-2, tyrosinase, and uroplakin-3.

In some embodiments, the tumor cell antigen is CD20. In some cases, the bispecific antibody is an anti-CD20×anti-CD3 antibody. In some cases, the anti-CD20×anti-CD3 antibody is REGN1979.

In some embodiments, the tumor cell antigen is BCMA. In some cases, the bispecific antibody is an anti-BCMA× anti-CD3 antibody.

In some embodiments, the tumor cell antigen is PSMA. In some cases, the bispecific antibody is an anti-PSMA×anti-CD3 antibody.

In some embodiments, the tumor cell antigen is MUC16. In some cases, the bispecific antibody is an anti-MUC16× anti-CD3 antibody.

In some embodiments, the tumor cell antigen is STEAP2. In some cases, the bispecific antibody is an anti-STEAP2× anti-CD3 antibody.

In various embodiments, the therapeutic protein is maintained at a serum concentration at or above about 2000 micrograms/liter (mcg/L) following administration of the maximum weekly dose for the duration of the dosing regimen. In some cases, the therapeutic protein is maintained at a serum concentration at or above about 2600 mcg/L following administration of the maximum weekly dose for the duration of the dosing regimen. In some embodiments, the therapeutic protein is maintained at a serum concentration at or above about 3700 mcg/L following administration of the maximum weekly dose for the duration of the dosing regimen.

In some embodiments, the therapeutic protein is administered to the subject in combination with a second agent selected from a steroid, an anti-histamine, acetaminophen, a non-steroidal anti-inflammatory drug (NSAID), an IL-6 antagonist, or an IL-6R antagonist. In some cases, the steroid is dexamethasone. In some cases, the NSAID is indomethacin. In some cases, the IL-6 antagonist is an anti-IL-6 antibody, or the IL-6R antagonist is an anti-IL-6R antibody. In some embodiments, the anti-IL-6R antibody is sarilumab. In various embodiments, administration of the second agent is eliminated following a first administration of the maximum weekly dose for the duration of the dosing regimen. In other embodiments, the second agent is administered prior to the administration of the therapeutic protein (e.g., about one to three hours prior to the F1D1, the F2D1, the F1D2, the F2D2, the F1D3 and/or the F2D3). In still other embodiments, the therapeutic protein is administered by infusion over a period of time such as 1, 2, 3, 4, 5, 6, 7, 8, 9, 10, 11, 12, or more hours.

In various embodiments, the therapeutic protein is administered to the subject in combination with a second therapeutic agent. In some embodiments, the second therapeutic agent comprises at least one of rituximab, obinutuzumab, cyclophophamide, doxorubicin, vincristine, prednisone, prednisolone, bendamustine, lenalidomide, chlorambucil, ibritumomab tiuxetan, idelalisib, copanlisib, duvelisib, etoposide, methylprednisolone, cytarabine, cisplatin, mesna, ifosfamide, mitoxantrone, and procarbazine. In some cases, the second therapeutic agent comprises a combination of cyclophosphamide, doxorubicin, vincristine and prednisone. In some cases, the second therapeutic agent comprises a combination of ifosfamide, cisplatin and etoposide. In some cases, the second therapeutic agent comprises a combination of gemcitabine and oxaliplatin. In some cases, the second therapeutic agent comprises a combination of lenalidomide and rituximab. In some cases, the second therapeutic agent is lenalidomide.

In one aspect, the present invention includes a method of treating a B cell cancer in a subject, comprising: (a) selecting a subject diagnosed with a B cell cancer; and (b) administering a therapeutic protein to the subject according to any of the methods discussed above or herein utilizing a dosing regimen to mitigate adverse effects of cytokine release syndrome or infusion-related reaction. In some embodiments, the subject has previously been treated with an anti-CD20 antibody therapy. In some embodiments, the subject has previously been treated with a CAR-T therapy. In some cases, the B cell cancer is selected from the group consisting of follicular lymphoma, diffuse large B-cell lymphoma, mantle cell lymphoma, and marginal zone lymphoma.

In any of the embodiments discussed above or herein, the incidence of grade 3 CRS and IRR is less than 10%. In some cases, the incidence of grade 3 CRS and IRR is less than 7.5% or less than 7%. In some embodiments, the maximum weekly dose is 80 mg or greater when the incidence of CRS and IRR is less than 10%, less than 9%, less than 8%, less than 7.5% or less than 7%. In any of the embodiments, any dose administered as a single dose may be administered in no more than 1 hour.

In various embodiments, any of the features or components of any embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges are encompassed within the scope of the present disclosure. A therapeutic protein for use in any of the methods discussed herein, or use of a therapeutic protein in the manufacture of a medicament for use in any of the methods discussed herein are also encompassed within the scope of this disclosure.

Other embodiments will become apparent from a review of the ensuing detailed description.

BRIEF DESCRIPTION OF THE DRAWINGS

FIG. 1 illustrates the incidence of CRS/IRR during the first five weeks of therapy with REGN1979 at various dose levels.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. The term "about," when used in reference to a particular recited numerical value, means that the value may vary from the recited value by no more than 1%. For example, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

The expression "CD3," refers to an antigen which is expressed on T cells as part of the multimolecular T cell receptor (TCR) and which consists of a homodimer or heterodimer formed from the association of two of four receptor chains: CD3-epsilon, CD3-delta, CD3-zeta, and CD3-gamma. Human CD3-epsilon comprises the amino acid sequence as set forth in SEQ ID NO: 1; human CD3-delta comprises the amino acid sequence as set forth in SEQ ID NO: 2; human CD3-zeta comprises the amino acid sequence as set forth in SEQ ID NO: 3; and CD3-gamma comprises the amino acid sequence as set forth in SEQ ID NO: 4.

All references to proteins, polypeptides and protein fragments herein are intended to refer to the human version of the respective protein, polypeptide or protein fragment unless explicitly specified as being from a non-human species. Thus, the expression "CD3" means human CD3 unless specified as being from a non-human species, e.g., "mouse CD3," "monkey CD3," etc.

"An antigen-binding domain that binds CD3," "an antibody that binds CD3" or an "anti-CD3 antibody" includes antibodies and antigen-binding fragments thereof that specifically recognize a single CD3 subunit (e.g., epsilon, delta, gamma or zeta), as well as antibodies and antigen-binding fragments thereof that specifically recognize a dimeric complex of two CD3 subunits (e.g., gamma/epsilon, delta/epsilon, and zeta/zeta CD3 dimers). The antibodies and antigen-binding fragments of the present invention may bind soluble CD3 and/or cell surface expressed CD3. Soluble CD3 includes natural CD3 proteins as well as recombinant CD3 protein variants such as, e.g., monomeric and dimeric CD3 constructs, that lack a transmembrane domain or are otherwise unassociated with a cell membrane.

The expression "CD20," refers to a non-glycosylated phosphoprotein expressed on the cell membranes of mature B cells. CD20 is considered a B cell tumor-associated antigen because it is expressed by more than 95% of B-cell non-Hodgkin lymphomas (NHLs) and other B-cell malignancies, but it is absent on precursor B-cells, dendritic cells and plasma cells. The human CD20 protein has the amino acid sequence shown in SEQ ID NO: 5.

"An antigen-binding domain that binds CD20," "an antibody that binds CD20" or an "anti-CD20 antibody" includes antibodies and antigen-binding fragments thereof that specifically recognize CD20.

The expression "BCMA," refers to B-cell maturation antigen. BCMA (also known as TNFRSF17 and CD269) is a cell surface protein expressed on malignant plasma cells, and plays a central role in regulating B cell maturation and differentiation into immunoglobulin-producing plasma cells. The amino acid sequence of human BCMA is shown in SEQ ID NO: 6.

"An antigen-binding domain that binds BCMA," "an antibody that binds BCMA" or an "anti-BCMA antibody" includes antibodies and antigen-binding fragments thereof that specifically recognize BCMA.

The expression "PSMA," refers to prostate-specific membrane antigen, also known as folate hydrolase 1 (FOLH1). PSMA is an integral, non-shed membrane glycoprotein that is highly expressed in prostate epithelial cells and is a cell-surface marker for prostate cancer. The amino acid sequence of human PSMA is set forth in SEQ ID NO: 7.

"An antigen-binding domain that binds PSMA," "an antibody that binds PSMA" or an "anti-PSMA antibody" includes antibodies and antigen-binding fragments thereof that specifically recognize PSMA.

The expression "MUC16," refers to mucin 16. MUC16 is a single transmembrane domain highly glycosylated integral membrane glycoprotein that is highly expressed in ovarian cancer. The amino acid sequence of human MUC16 is set forth in SEQ ID NO: 8.

"An antigen-binding domain that binds MUC16," "an antibody that binds MUC16" or an "anti-MUC16 antibody" includes antibodies and antigen-binding fragments thereof that specifically recognize MUC16.

The expression "STEAP2," refers to six-transmembrane epithelial antigen of prostate 2. STEAP2 is an integral, six-transmembrane-spanning protein that is highly expressed in prostate epithelial cells and is a cell-surface marker for prostate cancer. STEAP2 is a 490-amino acid protein encoded by STEAP2 gene located at the chromosomal region 7q21 in humans. The amino acid sequence of human STEAP2 is set forth in SEQ ID NO: 9.

"An antigen-binding domain that binds STEAP2," "an antibody that binds STEAP2" or an "anti-STEAP2 antibody" includes antibodies and antigen-binding fragments thereof that specifically recognize STEAP2.

The term "therapeutic protein," includes any polypeptide, including antibodies and antigen-binding fragments thereof, and bispecific antibodies and antigen-binding fragments thereof, which is used to prevent, treat or ameliorate any condition, disease or disorder in a subject.

The term "antigen-binding molecule" includes antibodies and antigen-binding fragments of antibodies, including, e.g., bispecific antibodies.

The term "antibody", means any antigen-binding molecule or molecular complex comprising at least one complementarity determining region (CDR) that specifically binds to or interacts with a particular antigen (e.g., CD20, BCMA, PSMA, MUC16, STEAP2 or CD3). The term "antibody" includes immunoglobulin molecules comprising four polypeptide chains, two heavy (H) chains and two light (L) chains inter-connected by disulfide bonds, as well as multimers thereof (e.g., IgM). The term "antibody" also includes immunoglobulin molecules consisting of four polypeptide chains, two heavy (H) chains and two light (L) chains inter-connected by disulfide bonds. Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the antibody (or antigen-binding portion thereof) may be identical to the human germline sequences, or may be naturally or artificially modified. An amino acid consensus sequence may be defined based on a side-by-side analysis of two or more CDRs. The term "antibody" includes a "bispecific antibody" unless otherwise noted.

The term "antibody", also includes antigen-binding fragments of full antibody molecules. The terms "antigen-binding portion" of an antibody, "antigen-binding fragment" of an antibody, and the like, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

The expression "bispecific antigen-binding molecule" refers to a protein, polypeptide or molecular complex comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. Bispecific antigen-binding molecules include bispecific antibodies.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment".

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; $V_H$-$C_H2$-$C_H3$; $V_H$-$C_L$; $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity. Antibodies of the present disclosure may include a human IgG heavy chain. In various embodiments, the heavy may be of IgG1, IgG2, IgG3 or IgG4 isotype.

In certain embodiments of the invention, the antibodies or bispecific antibodies are human antibodies. The term "human antibody" is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody" is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody" is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies of the invention may be isolated antibodies. An "isolated antibody" means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The antibodies discussed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes antibodies comprising variants of any of the HCVR, LCVR, and/or CDR amino acid sequences disclosed herein having one or more conservative substitutions. For example, the present invention includes antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth herein, the anti-CD3 antibodies disclosed in WO 2014/047231 or WO 2017/053856, the bispecific anti-CD20×anti-CD3 antibodies disclosed in WO 2014/047231, the anti-PSMA or anti-PSMA×anti-CD3 antibodies disclosed in WO 2017/023761, the anti-MUC16 or anti-MUC16×anti-CD3 antibodies disclosed in WO 2018/067331, the anti-STEAP2 or anti-STEAP2×anti-CD3 antibodies disclosed in WO 2018/058001, or the anti-BCMA or anti-BCMA×anti-CD3 antibodies disclosed in U.S. 62/700, 596 (filed Jul. 19, 2018), each of which is incorporated herein by reference.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Dosing Strategies and Administration Regimens

Dosing strategies were created that provide administration regimens to mitigate the prevalence or severity, or both, of cytokine release syndrome (CRS) or infusion-related reaction (IRR) by administration of a therapeutic protein to a patient for various therapies. According to certain embodiments of the present invention, these strategies include multiple doses of a therapeutic protein or an antigen-binding molecule (e.g., an antibody or a bispecific antibody) that may be administered to a subject over a defined time course to create a regimen. The methods according to this aspect of the invention comprise sequentially administering to a subject multiple doses of a therapeutic protein of the invention. "Sequentially administering" means that each dose of a therapeutic protein is administered to the subject at a different point in time, e.g., on different days separated by a predetermined interval (e.g., hours, days, weeks or months). The present invention includes methods which comprise sequentially administering to the patient a split primary dose of a therapeutic protein, followed by a split secondary dose of the therapeutic protein, optionally followed by a split tertiary dose of the therapeutic protein, followed by single doses of a maximum weekly dose of the therapeutic protein. The present administration regimens allow for higher doses of the therapeutic protein that are desirable for enhancing therapeutic efficacy, but without the deleterious effects associated with CRS or IRR. Without intending to be bound by any particular theory, the present administration regimens provide for priming of the immune response to administration of the therapeutic protein to minimize the incidence and severity of CRS and IRR during initial phases of the treatment regimen, which then permits administration of higher doses of the therapeutic proteins during subsequent phases of the treatment regimen without significant adverse events associated with CRS or IRR.

An exemplary administration regimen includes: (i) administering fractions of a primary dose of the therapeutic protein in week 1 (W1) of the dosing regimen, wherein the primary dose comprises no more than 1 mg of the therapeutic protein, a first dose fraction (F1D1) comprises 50% of the primary dose and is administered to the subject on day 1 of week 1, and a second dose fraction (F2D1) comprises 50% of the total primary dose and is administered to the subject within 96 hours following administration of the F1D1; (ii) administering fractions of a secondary dose of the therapeutic protein in week 2 (W2) of the dosing regimen, wherein the secondary dose is no more than one-half of a maximum weekly dose of the therapeutic protein, a first dose fraction (F1D2) comprises 50% of the secondary dose, a second dose fraction (F2D2) comprises 50% of the secondary dose, and the F1D2 and the F2D2 are administered to the subject within 96 hours of one another during week 2 of the dosing regimen; and (iii) administering the maximum weekly dose of the therapeutic protein to the subject as a single dose in a subsequent week (Ws) of the dosing regimen.

Another exemplary administration regimen includes: (i) administering fractions of a primary dose of the therapeutic protein in week 1 (W1) of the dosing regimen, wherein the primary dose comprises no more than 1 mg of the therapeutic protein, a first dose fraction (F1D1) comprises 50% of the primary dose and is administered to the subject on day 1 of week 1, and a second dose fraction (F2D1) comprises 50% of the total primary dose and is administered to the subject within 96 hours following administration of the F1D1; (ii) administering fractions of a secondary dose of the therapeutic protein in week 2 (W2) of the dosing regimen, wherein the secondary dose is no more than one-half of a maximum weekly dose of the therapeutic protein, a first dose fraction (F1D2) comprises 50% of the secondary dose, a second dose fraction (F2D2) comprises 50% of the secondary dose, and the F1D2 and the F2D2 are administered to the subject within 96 hours of one another during week 2 of the dosing regimen; (iii) administering fractions of a tertiary dose of the therapeutic protein in week 3 (W3) of the dosing regimen, wherein the tertiary dose is no less than one-half of the maximum weekly dose of the therapeutic protein and no more than the maximum weekly dose of the therapeutic protein, a first dose fraction (F1D3) comprises 50% of the tertiary dose, a second dose fraction (F2D3) comprises 50% of the tertiary dose, and the F1D3 and the F2D3 are administered to the subject within 96 hours of one another during week 3 of the dosing regimen; and (iv) administering the maximum weekly dose of the therapeutic protein to the subject as a single dose in a subsequent week (Ws) of the dosing regimen.

In various embodiments, the primary dose of the therapeutic protein can range from 0.1 mg to 10 mg or more. In some cases, the primary dose of the therapeutic protein is from 0.5 mg to 10 mg, from 1-10 mg, from 2-5 mg, or from 5-10 mg. In some cases, the primary dose of the therapeutic protein is 0.5, 1, 1.5, 2, 2.5, 3, 3.5, 4, 4.5, 5, 5.5, 6, 6.5, 7, 7.5, 8, 8.5, 9, 9.5 or 10 mg.

In various embodiments, the primary dose of the therapeutic protein comprises a range including any of the values noted above as the upper or lower end of the range (e.g., 1-5 mg) In various embodiments, the maximum weekly dose of the therapeutic protein is from 5 mg to 320 mg. In some embodiments, the maximum weekly dose of the therapeutic protein is from greater than 5 mg up to 320 mg. In some cases, the maximum weekly dose of the therapeutic protein is 6-320 mg, 10-320 mg, 5-40 mg, 5-80 mg, 5-160 mg, 12-40 mg, 18-80 mg, 40-80 mg, 80-160 mg, 160-320 mg, 5 mg, 6 mg, 7 mg, 8 mg, 12 mg, 18 mg, 27 mg, 40 mg, 80 mg, 160 mg or 320 mg. In some cases, the maximum weekly dose of the therapeutic protein is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, or 320 mg. In various embodiments, the maximum weekly dose of the therapeutic protein comprises a range including any of the values noted above as the upper or lower end of the range (e.g., 200-300 mg).

In various embodiments, the secondary dose comprises 50% of the maximum weekly dose of the therapeutic protein. In some cases, the secondary dose comprises 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, or 10% of the maximum weekly dose of the therapeutic protein. In some cases, the secondary dose of the therapeutic protein comprises a percentage range of the maximum weekly dose including any of the values noted above as the upper or lower end of the range (e.g., 35-50%).

In various embodiments, the tertiary dose comprises 50% of the maximum weekly dose of the therapeutic protein. In some cases, the tertiary dose comprises 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% of the maximum weekly dose of the therapeutic protein. In some cases, the tertiary dose of the therapeutic protein comprises a percentage range of the maximum weekly dose including any of the values noted above as the upper or lower end of the range (e.g., 50-75%).

In various embodiments, the first dose fraction and the second dose fraction of the primary, secondary, and/or tertiary doses each comprise 50% of the dose. In some cases, the first dose fraction and the second dose fraction of the primary, secondary, and/or tertiary doses comprise different percentages (totaling 100%) of the total dose. For example, the first dose fraction may comprise 45% of the dose, and the second dose fraction may comprise 55% of the dose. Alternatively, the first dose fraction may comprise 55% of the dose, and the second dose fraction may comprise 45% of the dose. In various embodiments, the first and second dose fractions may include 10%/90%, 15%/85%, 20%/80%, 25%/75%, 30%/70%, 35%/65%, 40%/60%, 46%/54%, 47%/53%, 48%/52%, 49%/51%, or vice versa, of the total primary, secondary, or tertiary dose, respectively.

In various embodiments, the primary, secondary and/or tertiary doses (D1, D2 and/or D3) can be split into two or more fractions. Various options for splitting the doses into two fractions are discussed above. In some cases, however, the doses are split into 3, 4 or 5 fractions. For example, the primary dose could be split into 5 fractions, each comprising 20% of the total primary dose, and each dose fraction (F1D1, F2D1, F3D1, F4D1, and F5D1) can be administered to the subject on five consecutive days during the first week of the administration regimen. In other cases, the percentage of the total dose (e.g., the primary dose) may vary among each dose fraction. For example, if the primary dose is split into 3 fractions, the first dose fraction (F1D1) may include 30% of the total primary dose, the second dose fraction (F2D1) may include 30% of the total primary dose, and the third dose fraction (F3D1) may include the remaining 40% of the total primary dose. Other combinations of the percentages and number of fractional doses that equal 100% of the total dose are expressly contemplated herein.

In one exemplary embodiment of the dosing regimen, the primary dose comprises 1 mg, each of the first dose fraction (F1D1) and the second dose fraction (F2D1) comprises 500 mcg, the secondary dose comprises 6 mg, each of the first dose fraction (F1D2) and the second dose fraction (F2D2) comprise 3 mg, the tertiary dose comprises 12 mg, each of the first dose fraction (F1D3) and the second dose fraction F2D3) comprise 6 mg, and the maximum weekly dose comprises 12 mg of the therapeutic protein.

In one exemplary embodiment of the dosing regimen, the primary dose comprises 1 mg, each of the first dose fraction (F1D1) and the second dose fraction (F2D1) comprises 500 mcg, the secondary dose comprises 9 mg, each of the first dose fraction (F1D2) and the second dose fraction (F2D2) comprise 4.5 mg, the tertiary dose comprises 18 mg, each of the first dose fraction (F1D3) and the second dose fraction F2D3) comprise 9 mg, and the maximum weekly dose comprises 18 mg of the therapeutic protein.

In one exemplary embodiment of the dosing regimen, the primary dose comprises 1 mg, each of the first dose fraction (F1D1) and the second dose fraction (F2D1) comprises 500 mcg, the secondary dose comprises 13.5 mg, each of the first dose fraction (F1D2) and the second dose fraction (F2D2) comprise 6.75 mg, the tertiary dose comprises 27 mg, each of the first dose fraction (F1D3) and the second dose fraction F2D3) comprise 13.5 mg, and the maximum weekly dose comprises 27 mg of the therapeutic protein.

In one exemplary embodiment of the dosing regimen, the primary dose comprises 1 mg, each of the first dose fraction (F1D1) and the second dose fraction (F2D1) comprises 500 mcg, the secondary dose comprises 20 mg, each of the first dose fraction (F1D2) and the second dose fraction (F2D2) comprise 10 mg, the tertiary dose comprises 40 mg, each of the first dose fraction (F1D3) and the second dose fraction F2D3) comprise 20 mg, and the maximum weekly dose comprises 40 mg of the therapeutic protein.

In one exemplary embodiment of the dosing regimen, the primary dose comprises 1 mg, each of the first dose fraction (F1D1) and the second dose fraction (F2D1) comprises 500 mcg, the secondary dose comprises 20 mg, each of the first dose fraction (F1D2) and the second dose fraction (F2D2) comprise 10 mg, the tertiary dose comprises 60 mg, each of the first dose fraction (F1D3) and the second dose fraction F2D3) comprise 30 mg, and the maximum weekly dose comprises 80 mg of the therapeutic protein.

In one exemplary embodiment of the dosing regimen, the primary dose comprises 1 mg, each of the first dose fraction (F1D1) and the second dose fraction (F2D1) comprises 500 mcg, the secondary dose comprises 20 mg, each of the first dose fraction (F1D2) and the second dose fraction (F2D2) comprise 10 mg, the tertiary dose comprises 80 mg, each of the first dose fraction (F1D3) and the second dose fraction F2D3) comprise 40 mg, and the maximum weekly dose comprises 160 mg of the therapeutic protein.

In one exemplary embodiment of the dosing regimen, the primary dose comprises 1 mg, each of the first dose fraction (F1D1) and the second dose fraction (F2D1) comprises 500 mcg, the secondary dose comprises 20 mg, each of the first dose fraction (F1D2) and the second dose fraction (F2D2) comprise 10 mg, the tertiary dose comprises 120 mg, each of the first dose fraction (F1D3) and the second dose fraction F2D3) comprise 60 mg, and the maximum weekly dose comprises 240 mg of the therapeutic protein.

In one exemplary embodiment of the dosing regimen, the primary dose comprises 1 mg, each of the first dose fraction (F1D1) and the second dose fraction (F2D1) comprises 500 mcg, the secondary dose comprises 20 mg, each of the first dose fraction (F1D2) and the second dose fraction (F2D2) comprise 10 mg, the tertiary dose comprises 160 mg, each of the first dose fraction (F1D3) and the second dose fraction F2D3) comprise 80 mg, and the maximum weekly dose comprises 320 mg of the therapeutic protein.

In one exemplary embodiment of the dosing regimen, the primary dose (D1) comprises 1 mg, each of the first dose fraction (F1D1) and the second dose fraction (F2D2) of the primary dose comprises 500 mcg, the secondary dose (D2) comprises 3 mg, each of the first dose fraction (F1D2) and the second dose fraction (F2D2) of the secondary dose comprises 1.5 mg, and the maximum weekly dose comprises 3 mg of the therapeutic protein.

In one exemplary embodiment of the dosing regimen, the primary dose (D1) comprises 3 mg, each of the first dose fraction (F1D1) and the second dose fraction (F2D2) of the primary dose comprises 1.5 mg, the secondary dose (D2) comprises 9 mg, each of the first dose fraction (F1D2) and the second dose fraction (F2D2) of the secondary dose comprises 4.5 mg, and the maximum weekly dose comprises 9 mg of the therapeutic protein.

In one exemplary embodiment of the dosing regimen, the primary dose (D1) comprises 5 mg, each of the first dose fraction (F1D1) and the second dose fraction (F2D2) of the primary dose comprises 2.5 mg, the secondary dose (D2) comprises 15 mg, each of the first dose fraction (F1D2) and the second dose fraction (F2D2) of the secondary dose comprises 7.5 mg, and the maximum weekly dose comprises 15 mg of the therapeutic protein.

In one exemplary embodiment of the dosing regimen, the primary dose (D1) comprises 10 mg, each of the first dose fraction (F1D1) and the second dose fraction (F2D2) of the primary dose comprises 5 mg, the secondary dose (D2) comprises 30 mg, each of the first dose fraction (F1D2) and the second dose fraction (F2D2) of the secondary dose comprises 15 mg, and the maximum weekly dose comprises 30 mg of the therapeutic protein.

In various embodiments, the therapeutic protein is administered at a dose to maintain a serum concentration of at least about 2000 mcg/L following administration of the maximum weekly dose for the duration of the dosing regimen. In some cases, the therapeutic protein is administered at a dose to maintain a serum concentration of at least about 2100, 2200, 2300, 2400, 2500, 2600, 2700, 2800, 2900, 3000, 3100, 3200, 3300, 3400, or 3500 mcg/L following administration of the maximum weekly dose for the duration of the dosing regimen.

In various embodiments, the therapeutic protein is administered at a dose to maintain an average serum concentration of at least about 2600 mcg/L following administration of the maximum weekly dose for the duration of the dosing regimen. In some cases, the therapeutic protein is administered at a dose to maintain an average serum concentration of at least about 2000, 2100, 2200, 2300, 2400, 2500, 2700, 2800, 2900, 3000, 3100, 3200, 3300, 3400, 3500, 3600, 3700, 3800, 3900 or 4000 mcg/L following administration of the maximum weekly dose for the duration of the dosing regimen.

In various embodiments, the subsequent week (Ws) of the dosing regimen is week 3 (W3), week 4 (W4), week 5 (W5), week 6 (W6), week 7 (W7), week 8 (W8), week 9 (W9), week 10 (W10), week 11 (W11), week 12 (W12), week 13 (W13), week 14 (W14), week 15 (W15), week 16 (W16), week 17 (W17), week 18 (W18), week 19 (W19), week 20 (W20), week 21 (W21), week 22 (W22), week 23 (W23), week 24 (W24), week 25 (W25), week 26 (W26), week 27 (W27), week 28 (W29), week 30 (W30), week 31 (31), week 32 (32), week 33 (33), week 34 (W34), week 35 (W35), or week 36 (W36).

In various embodiments, the second fractional dose in any given week of the dosing regimen is administered within 24, 36, 48, 60, 72, 84 or 96 hours following administration of the first fractional dose.

In various embodiments, the maximum weekly dose of the therapeutic protein is administered to the subject as a single dose for from 1 to 8 weeks, or for 1, 2, 3, 4, 5, 6, 7, 8, 9, 10, 11, 12, 13, 14, 15, 16, 17, 18, 19, 20, 21, 22, 23, 24, 25, 26 or more weeks during a weekly phase of the dosing regimen. In some cases, the maximum weekly dose of the therapeutic protein is administered to the subject as a single dose over a range of weeks including any of the values noted above as the upper or lower end of the range (e.g., 1-12 weeks).

In various embodiments, the maximum weekly dose of the therapeutic protein is administered to the subject as a single dose (maintenance dose) once every two weeks for up to 24 weeks, or for up to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 95, 100, 110, 120, 130, 140, 150, 160, 170, 180, 190, 200, 210, 220, 230, 240, 250, 260 or more weeks during a biweekly, triweekly, tetraweekly, or pentaweekly phase (maintenance phase) of the dosing regimen, which may follow completion of the weekly phase of the dosing regimen (i.e., either the weekly dosing of the maximum weekly dose or the split dosing of the primary, secondary and (optionally) tertiary doses. In some cases, the maximum weekly dose of the therapeutic protein is administered to the subject as a single dose (maintenance dose) once every two weeks, one every three weeks, or once every four weeks over a range of weeks including any of the values noted above as the upper or lower end of the range (e.g., 24-86 weeks).

In one exemplary embodiment of the dosing regimen, the primary dose comprises 1 mg, each of the first dose fraction (F1D1) and the second dose fraction (F2D1) comprises 500 mcg, the secondary dose comprises 20 mg, each of the first dose fraction (F1D2) and the second dose fraction (F2D2) comprise 10 mg, the tertiary dose comprises 80 mg, each of the first dose fraction (F1D3) and the second dose fraction F2D3) comprise 40 mg, and the maximum weekly dose comprises 160 mg of the therapeutic protein, wherein the tertiary dose is administered as a single dose (i.e., 80 mg) weekly (QW) during weeks 4 to 12 of the dosing regimen, and the maximum weekly dose is administered as a single dose (i.e., 160 mg) once every two weeks (Q2W) from week 14 onwards of the dosing regimen.

In some cases, the above-identified dosing regimen is for use in methods of treating an aggressive lymphoma (e.g., mantle cell lymphoma or marginal zone lymphoma).

In one exemplary embodiment of the dosing regimen, the primary dose comprises 1 mg, each of the first dose fraction (F1D1) and the second dose fraction (F2D1) comprises 500 mcg, the secondary dose comprises 20 mg, each of the first dose fraction (F1D2) and the second dose fraction (F2D2) comprise 10 mg, the tertiary dose comprises 160 mg, each of the first dose fraction (F1D3) and the second dose fraction F2D3) comprise 80 mg, and the maximum weekly dose comprises 320 mg of the therapeutic protein, wherein the tertiary dose is administered as a single dose (i.e., 160 mg) weekly (QW) during weeks 4 to 12 of the dosing regimen, and the maximum weekly dose is administered as a single dose (i.e., 320 mg) once every two weeks (Q2W) from week 14 onwards of the dosing regimen.

In some cases, the above-identified dosing regimen is for use in methods of treating an aggressive lymphoma (e.g., mantle cell lymphoma or marginal zone lymphoma). In some cases, the above-identified dosing regimen is for use in methods of treating follicular lymphoma (e.g., grade 1-3a). In some cases, the above-identified dosing regimen is for treating diffuse large B cell lymphoma (including relapsed or refractory DLBCL, e.g., in patients that have failed prior CAR-T therapy).

In various embodiments, each dose or fractional dose of the therapeutic protein is administered to the subject over a period of from 1-4, 1-5, or 1-6 hours (e.g., via infusion). In some cases, the dose or fractional dose is administered over a period of 1, 2, 3, 4, 5, 6, 7, 8, 9, 10, 11 or 12 or more hours. In some cases, each dose or fractional dose of the therapeutic protein is administered to the subject over a range of time including any of the values noted above as the upper or lower end of the range (e.g., 1-8 hours). In various embodiments, each maximum weekly dose is administered as a single infusion.

In some embodiments of the administration regimens discussed herein, a second agent is administered as a pretreatment, or in combination with, the therapeutic protein. In some cases, a steroid, such as dexamethasone, is administered to the patient as a pretreatment prior to administration of the primary fractional doses and the secondary fractional doses, and optionally prior to the tertiary fractional doses. In some embodiments, the dexamethasone is administered to the patient about one to three hours prior to the first dose fraction (F1D1). In certain embodiments the dexamethasone dose is administered by intravenous infusion. In some cases, a cytokine antagonist, such an anti-IL-6 antibody or an anti-IL-6R antibody is administered in combination with the therapeutic protein during the primary, secondary, and optionally the tertiary dose administrations. In some cases, an anti-CD20 monospecific antibody (e.g., rituximab) is administered to the patient as a pretreatment prior to administration of the primary fractional doses and optionally the secondary fractional doses, and optionally prior to the tertiary fractional doses. These pretreatment or combination administrations of the second agent are discontinued, in an embodiment, with the single dose administration of the maximum weekly dose beginning at, e.g., week 3, week 4, week 5 or week 6 of the dosing regimen so as to not artificially dampen cytokine activity and thereby impede the therapeutic effects of the therapeutic protein.

The terms "primary dose," "secondary dose," and "tertiary doses," refer to the temporal sequence of administration of the antigen-binding molecule of the invention. Thus, the "primary dose" is the dose which is administered at the beginning of the treatment regimen; the "secondary dose" is the dose which is administered after the primary dose (including all dose fractions of the primary dose); and the "tertiary doses" are the doses which are administered after the secondary dose (including all dose fractions of the secondary dose). The primary, secondary, and tertiary doses (or their dose fractions) may contain an amount of the therapeutic protein as discussed herein. In some cases, the "primary dose" and "secondary dose," as well as the optional "tertiary dose" may be referred to as "loading doses," while the subsequent maximum weekly doses may be referred to as "maintenance doses". In some cases, the "primary dose" may be referred to as the "initial dose." In some cases, the "secondary dose" may be referred to as the "intermediate dose." In some cases, the "tertiary dose" may be referred to as the "step-up dose."

The phrase "the immediately preceding dose," refers to, in a sequence of multiple administrations, the dose of antigen-binding molecule which is administered to a patient prior to the administration of the very next dose in the sequence with no intervening doses.

Antigen-Binding Molecules

The antibodies for use in connection with the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The antibodies and bispecific antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second or additional binding specificity.

The present invention includes antibodies having the HCVR, LCVR and/or CDR amino acid sequences of the antibodies set forth herein, the anti-CD3 antibodies disclosed in WO 2014/047231 or WO 2017/053856, the bispecific anti-CD20×anti-CD3 antibodies disclosed in WO 2014/047231, the anti-PSMA or anti-PSMA×anti-CD3 antibodies disclosed in WO 2017/023761, the anti-MUC16 or anti-MUC16×anti-CD3 antibodies disclosed in WO 2018/067331, the anti-STEAP2 or anti-STEAP2×anti-CD3 antibodies disclosed in WO 2018/058001, or the anti-BCMA or anti-BCMA×anti-CD3 antibodies disclosed in U.S. 62/700,596 (filed Jul. 19, 2018), each of which is incorporated herein by reference.

Use of the expression "anti-CD3 antibody," "anti-CD20 antibody," "anti-PSMA antibody," anti-MUC16 antibody," "anti-STEAP2 antibody," "anti-BCMA antibody," or the like herein is intended to include both monospecific antibodies as well as bispecific antibodies comprising the respective antigen-binding arm (e.g., CD3). Thus, the present invention includes bispecific antibodies wherein one arm of an immunoglobulin binds human CD3, and the other arm of the immunoglobulin is specific for, e.g., human CD20, human PSMA, human MUC16, human STEAP2, or human BCMA.

In certain embodiments, the CD3-binding arm binds to human CD3 and induces human T cell activation. In certain embodiments, the CD3-binding arm binds weakly to human CD3 and induces human T cell activation. In other embodiments, the CD3-binding arm binds weakly to human CD3 and induces tumor-associated antigen-expressing cell killing in the context of a bispecific or multispecific antibody. In other embodiments, the CD3-binding arm binds or associates weakly with human and cynomolgus (monkey) CD3, yet the binding interaction is not detectable by in vitro assays known in the art. In certain embodiments, the bispecific antibodies or antigen-binding fragments for use in the present invention comprise an antigen-binding arm that binds to CD28, ICOS, HVEM, CD27, 4-1BB, OX40, DR3, GITR, CD30, SLAM, CD2, 2B4, CD226, TIM1, or TIM2 to induce T cell activation.

In certain exemplary embodiments of the present invention, the bispecific antigen-binding molecule is a bispecific antibody. Each antigen-binding domain of a bispecific antibody comprises a heavy chain variable domain (HCVR) and a light chain variable domain (LCVR). In the context of a bispecific antigen-binding molecule comprising a first and a second antigen-binding domain (e.g., a bispecific antibody), the CDRs of the first antigen-binding domain may be designated with the prefix "A1" and the CDRs of the second antigen-binding domain may be designated with the prefix "A2". Thus, the CDRs of the first antigen-binding domain may be referred to herein as A1-HCDR1, A1-HCDR2, and A1-HCDR3; and the CDRs of the second antigen-binding domain may be referred to herein as A2-HCDR1, A2-HCDR2, and A2-HCDR3.

In one embodiment, the therapeutic protein is a bispecific anti-CD20×anti-CD3 antibody known as REGN1979. REGN1979 comprises an anti-CD20 binding arm comprising a heavy chain comprising the amino acid sequence of SEQ ID NO: 10, an anti-CD3 binding arm comprising a heavy chain comprising the amino acid sequence of SEQ ID NO: 11, and a common light chain (corresponding to both the anti-CD20 and anti-CD3 binding arms) comprising the amino acid sequence of SEQ ID NO: 12. In some cases, the mature form of the antibody may not include the C-terminal lysine residues of SEQ ID NOs: 10 and 11. Thus, in some cases the anti-CD20 binding arm of REGN1979 comprises a heavy chain comprising residues 1-452 of SEQ ID NO: 10, and the anti-CD3 binding arm of REGN1979 comprises a heavy chain comprising residues 1-448 of SEQ ID NO: 11. REGN1979 also comprises the HCVR, LCVR and CDR sequences set forth in the accompanying sequence listing. The anti-CD20 HCVR corresponds to SEQ ID NO: 13, the anti-CD3 HCVR corresponds to SEQ ID NO: 14, and the common LCVR corresponds to SEQ ID NO: 15. The anti-CD20 HCDR1-HCDR2-HCDR3 domains correspond to SEQ ID NOs: 16-17-18, respectively. The anti-CD3 HCDR1-HCDR2-HCDR3 domains correspond to SEQ ID NOs: 19-20-21, respectively. The common LCDR1-LCDR2-LCDR3 domains correspond to SEQ ID NOs: 22-23-24, respectively.

The bispecific antigen-binding molecules discussed above or herein may be bispecific antibodies. In some cases, the bispecific antibody comprises a human IgG heavy chain constant region. In some cases, the human IgG heavy chain constant region is isotype IgG1. In some cases, the human IgG heavy chain constant region is isotype IgG4. In various embodiments, the bispecific antibody comprises a chimeric hinge that reduces Fcγ receptor binding relative to a wild-type hinge of the same isotype. In some cases, the bispecific antigen-binding molecules of the present invention comprise any one of the formats discussed in Brinkmann et al., MABS, 9(2):182-212, 2017, which is incorporated herein by reference.

The first antigen-binding domain and the second antigen-binding domain may be directly or indirectly connected to one another to form a bispecific antigen-binding molecule of the present invention. Alternatively, the first antigen-binding domain and the second antigen-binding domain may each be connected to a separate multimerizing domain. The association of one multimerizing domain with another multimerizing domain facilitates the association between the two antigen-binding domains, thereby forming a bispecific antigen-binding molecule. A "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin $C_H3$ domain. A non-limiting example of a multimerizing component is an Fc portion of an immunoglobulin (comprising a $C_H2$-$C_H3$ domain), e.g., an Fc domain of an IgG selected from the isotypes IgG1, IgG2, IgG3, and IgG4, as well as any allotype within each isotype group.

Bispecific antigen-binding molecules of the present invention will typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

In certain embodiments, the multimerizing domain is an Fc fragment or an amino acid sequence of from 1 to about 200 amino acids in length containing at least one cysteine residue. In other embodiments, the multimerizing domain is a cysteine residue, or a short cysteine-containing peptide. Other multimerizing domains include peptides or polypeptides comprising or consisting of a leucine zipper, a helix-loop motif, or a coiled-coil motif.

Any bispecific antibody format or technology may be used to make the bispecific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats).

In the context of bispecific antigen-binding molecules of the present invention, the multimerizing domains, e.g., Fc domains, may comprise one or more amino acid changes (e.g., insertions, deletions or substitutions) as compared to the wild-type, naturally occurring version of the Fc domain. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a $C_H2$ or a $C_H3$ region, wherein the modification increases the affinity of the Fc domain to FcRn in an acidic environment (e.g., in an endosome where pH ranges from about 5.5 to about 6.0). Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

The present invention also includes bispecific antigen-binding molecules comprising a first $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). See, for example, U.S. Pat. No. 8,586,713. Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies.

In certain embodiments, the Fc domain may be chimeric, combining Fc sequences derived from more than one immunoglobulin isotype. For example, a chimeric Fc domain can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 $C_H1$]-[IgG4 upper hinge]-[IgG2 lower hinge]-[IgG4 $C_H2$]-[IgG4 $C_H3$]. Another example of a chimeric Fc domain that can be included in any of the antigen-binding molecules set forth herein comprises, from N- to C-terminus: [IgG1 $C_H1$]-[IgG1 upper hinge]-[IgG2 lower hinge]-[IgG4 $C_H2$]-[IgG1 CH3]. These and other examples of chimeric Fc domains that can be included in any of the antigen-binding molecules of the present invention are described in US Publication 2014/0243504, published Aug. 28, 2014, which is herein incorporated in its entirety. Chimeric Fc domains having these general structural arrangements, and variants thereof, can have altered Fc receptor binding, which in turn affects Fc effector function.

Binding Properties of the Antigen-Binding Molecules

The term "binding" in the context of the binding of an antibody, immunoglobulin, antibody-binding fragment, or Fc-containing protein to either, e.g., a predetermined antigen, such as a cell surface protein or fragment thereof, typically refers to an interaction or association between a minimum of two entities or molecular structures, such as an antibody-antigen interaction.

For instance, binding affinity typically corresponds to a $K_D$ value of about $10^{-7}$ M or less, such as about $10^{-8}$ M or less, such as about $10^{-9}$ M or less when determined by, for instance, surface plasmon resonance (SPR) technology in a BIAcore 3000 instrument using the antigen as the ligand and the antibody, Ig, antibody-binding fragment, or Fc-containing protein as the analyte (or antiligand). Cell-based binding strategies, such as fluorescent-activated cell sorting (FACS) binding assays, are also routinely used, and FACS data correlates well with other methods such as radioligand competition binding and SPR (Benedict, C A, *J Immunol Methods*. 1997, 201(2):223-31; Geuijen, C A, et al. *J Immunol Methods*. 2005, 302(1-2):68-77).

Accordingly, the antibody or antigen-binding protein of the invention binds to the predetermined antigen or cell surface molecule (receptor) having an affinity corresponding to a $K_D$ value that is at least ten-fold lower than its affinity for binding to a non-specific antigen (e.g., BSA, casein). According to the present invention, the affinity of an antibody corresponding to a $K_D$ value that is equal to or less than ten-fold lower than a non-specific antigen may be considered non-detectable binding, however such an antibody may be paired with a second antigen binding arm for the production of a bispecific antibody of the invention.

The term "$K_D$" (M) refers to the dissociation equilibrium constant of a particular antibody-antigen interaction, or the dissociation equilibrium constant of an antibody or antibody-binding fragment binding to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g. antibody) to its interactive partner molecule (e.g. antigen X) compared to the binding affinity of the molecule (e.g. antibody) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

The term "$k_d$" (sec-1 or 1/s) refers to the dissociation rate constant of a particular antibody-antigen interaction, or the dissociation rate constant of an antibody or antibody-binding fragment. Said value is also referred to as the $k_{off}$ value.

The term "$k_a$" (M-1×sec-1 or 1/M) refers to the association rate constant of a particular antibody-antigen interaction, or the association rate constant of an antibody or antibody-binding fragment.

The term "$K_A$" (M-1 or 1/M) refers to the association equilibrium constant of a particular antibody-antigen interaction, or the association equilibrium constant of an antibody or antibody-binding fragment. The association equilibrium constant is obtained by dividing the $k_a$ by the $k_d$.

The term "EC50" or "$EC_{50}$" refers to the half maximal effective concentration, which includes the concentration of an antibody which induces a response halfway between the baseline and maximum after a specified exposure time. The $EC_{50}$ essentially represents the concentration of an antibody where 50% of its maximal effect is observed. In certain embodiments, the $EC_{50}$ value equals the concentration of an antibody of the invention that gives half-maximal binding to cells expressing, e.g., CD3 or a tumor-associated antigen (e.g., CD20), as determined by e.g. a FACS binding assay. Thus, reduced or weaker binding is observed with an increased $EC_{50}$, or half maximal effective concentration value.

In one embodiment, decreased binding can be defined as an increased $EC_{50}$ antibody concentration which enables binding to the half-maximal amount of target cells.

In another embodiment, the $EC_{50}$ value represents the concentration of an antibody of the invention that elicits half-maximal depletion of target cells by T cell cytotoxic activity. Thus, increased cytotoxic activity (e.g. T cell-mediated tumor cell killing) is observed with a decreased $EC_{50}$, or half maximal effective concentration value.

Sequence Variants

The antibodies and bispecific antigen-binding molecules of the present invention may comprise one or more amino acid substitutions, insertions and/or deletions in the framework and/or CDR regions of the heavy and light chain variable domains as compared to the corresponding germline sequences from which the individual antigen-binding domains were derived. Such mutations can be readily ascertained by comparing the amino acid sequences disclosed herein to germline sequences available from, for example, public antibody sequence databases. The antigen-binding molecules of the present invention may comprise antigen-binding domains which are derived from any of the exemplary amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antigen-binding domain was originally derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antigen-binding domain was originally derived). Furthermore, the antigen-binding domains may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antigen-binding domains that contain one or more germline mutations can be easily tested for one or more desired property such as, improved binding specificity, increased binding affinity, improved or enhanced antagonistic or agonistic biological properties (as the case may be), reduced immunogenicity, etc. Bispecific antigen-binding molecules comprising one or more antigen-binding domains obtained in this general manner are encompassed within the present invention.

pH-Dependent Binding

The present invention includes antibodies and bispecific antigen-binding molecules with pH-dependent binding characteristics. For example, an antibody of the present invention may exhibit reduced binding to, e.g., a tumor antigen such as CD20 at acidic pH as compared to neutral pH. Alternatively, antibodies of the invention may exhibit enhanced binding to, e.g., a tumor antigen such as CD20 at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. The expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding . . . at acidic pH as compared to neutral pH" is expressed in terms of a ratio of the $K_D$ value of the antibody binding to its antigen at acidic pH to the $K_D$ value of the antibody binding to its antigen at neutral pH (or vice versa). For example, an antibody or antigen-binding fragment thereof may be regarded as exhibiting "reduced binding to, e.g., CD20 at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Antibodies Comprising Fc Variants

According to certain embodiments of the present invention, antibodies and bispecific antigen-binding molecules are provided comprising an Fc domain comprising one or more mutations which enhance or diminish antibody binding to the FcRn receptor, e.g., at acidic pH as compared to neutral pH. For example, the present invention includes antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes antibodies and bispecific antigen-binding molecules comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Preparation of Antigen-Binding Domains and Construction of Bispecific Molecules

Antigen-binding domains specific for particular antigens can be prepared by any antibody generating technology known in the art. Once obtained, two different antigen-binding domains, specific for two different antigens (e.g., CD3 and CD20), can be appropriately arranged relative to one another to produce a bispecific antigen-binding molecule of the present invention using routine methods. (A discussion of exemplary bispecific antibody formats that can be used to construct the bispecific antigen-binding molecules of the present invention is provided elsewhere herein). In certain embodiments, one or more of the individual components (e.g., heavy and light chains) of the multispecific antigen-binding molecules of the invention are derived from chimeric, humanized or fully human antibodies. Methods for making such antibodies are well known in the art. For example, one or more of the heavy and/or light chains of the bispecific antigen-binding molecules of the present invention can be prepared using VELOCIMMUNE™ technology. Using VELOCIMMUNE™ technology (or any other human antibody generating technology), high affinity chimeric antibodies to a particular antigen (e.g., CD3 or CD20) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the bispecific antigen-binding molecules of the present invention.

Genetically engineered animals may be used to make human bispecific antigen-binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa constant gene at the endogenous mouse kappa locus. Such genetically modified mice can be used to produce fully human bispecific antigen-binding molecules comprising two different heavy chains that associate with an identical light chain that comprises a variable domain derived from one of two different human light chain variable region gene segments. (See, e.g., US 2011/0195454). Fully human refers to an antibody, or antigen-binding fragment or immunoglobulin domain thereof, comprising an amino acid sequence encoded by a DNA derived from a human sequence over the entire length of each polypeptide of the antibody or antigen-binding fragment or immunoglobulin domain thereof. In some instances, the fully human sequence is derived from a protein endogenous to a human. In other instances, the fully human protein or protein sequence comprises a chimeric sequence wherein each component sequence is derived from human sequence. While not being bound by any one theory, chimeric proteins or chimeric sequences are generally designed to minimize the creation of immunogenic epitopes in the junctions of component sequences, e.g. compared to any wild-type human immunoglobulin regions or domains.

Bioequivalents

The present invention encompasses antigen-binding molecules having amino acid sequences that vary from those of the exemplary molecules disclosed herein but that retain the ability to bind the same antigen or antigens. Such variant molecules may comprise one or more additions, deletions, or substitutions of amino acids when compared to parent sequence, but exhibit biological activity that is essentially equivalent to that of the described antibodies or bispecific antigen-binding molecules.

The present invention includes antigen-binding molecules that are bioequivalent to any of the exemplary antigen-binding molecules set forth herein. Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple dose. Some antigen-binding proteins will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antigen-binding protein.

Bioequivalent variants of the exemplary antibodies and bispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antigen-binding proteins may include variants of the exemplary antibodies and bispecific antigen-binding molecules set forth herein comprising amino acid changes which modify the glycosylation characteristics of the molecules, e.g., mutations which eliminate or remove glycosylation.

Therapeutic Formulation and Delivery

The present invention provides pharmaceutical compositions comprising the antigen-binding molecules of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In one embodiment, the therapeutic proteins of the invention are administered via intravenous infusion.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Therapeutic Uses of the Antigen-Binding Molecules

The present invention includes methods comprising administering to a subject in need thereof a therapeutic composition comprising a therapeutic protein. The therapeutic composition can comprise any of the antibodies or bispecific antigen-binding molecules as disclosed herein and a pharmaceutically acceptable carrier or diluent. The expression "a subject in need thereof" means a human or non-human animal that exhibits one or more symptoms or indicia of cancer (e.g., a subject expressing a tumor or suffering from any of the cancers mentioned herein below).

The antibodies and bispecific antigen-binding molecules of the invention (and therapeutic compositions comprising the same) are useful, inter alia, for treating any disease or disorder in which stimulation, activation and/or targeting of an immune response would be beneficial. In particular, the antibodies or the bispecific antigen-binding molecules of the present invention may be used for the treatment, prevention and/or amelioration of any disease or disorder associated with or mediated by, e.g., CD20, PSMA, MUC16, STEAP2 or BCMA expression or activity or the proliferation of CD20+, PSMA+, MUC16+, STEAP2+, or BCMA+ cells. The mechanism of action by which the therapeutic methods of the invention are achieved include killing of the cells expressing such antigens in the presence of effector cells, for example, by CDC, apoptosis, ADCC, phagocytosis, or by a combination of two or more of these mechanisms.

The antigen-binding molecules of the present invention may be used to treat, e.g., primary and/or metastatic tumors arising in the brain and meninges, head and neck, oropharynx, lung and bronchial tree, gastrointestinal tract, male and female reproductive tract, muscle, bone, skin and appendages, connective tissue, spleen, immune system, blood forming cells and bone marrow, liver and urinary tract, kidney, bladder and/or special sensory organs such as the eye. In certain embodiments, the antibodies and bispecific antigen-binding molecules of the invention are used to treat one or more of, but not limited to, the following cancers: pancreatic carcinoma, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, small cell lung cancer, non-small cell lung cancer, synovial sarcoma, thyroid cancer, breast cancer, melanomaglioma, breast cancer (e.g. ductal or intraductal breast carcinoma, squamous cell carcinoma, esophageal cancer, clear cell renal cell carcinoma, chromophobe renal cell carcinoma, (renal) oncocytoma, (renal) transitional cell carcinoma, urothelial carcinoma, (bladder) adenocarcinoma, or (bladder) small cell carcinoma. According to certain embodiments of the present invention, the antibodies or bispecific antibodies are useful for treating a patient afflicted with a refractory or treatment-resistant cancer, e.g. castrate-resistant prostate cancer.

In some embodiments, the antigen-binding molecule is a bispecific anti-CD3×anti-CD20 antibody useful for treating a CD20-expressing cancer including non-Hodgkin lymphoma, Hodgkin lymphoma, chronic lymphocytic leukemia, acute lymphoblastic leukemia, small lymphocytic lymphoma, diffuse large B-cell lymphoma, follicular lymphoma, mantle cell lymphoma, marginal zone lymphoma, Waldenstrom macroglobulinemia, primary mediastinal B-cell lymphoma, lymphoblastic lymphoma, or Burkitt lymphoma. In some embodiments, the cancer is follicular lymphoma. In some embodiments, the cancer is diffuse large B-cell lymphoma (DLBCL). In some embodiments, the cancer is mantle cell lymphoma. In some embodiments, the cancer is marginal zone lymphoma. In some embodiments, the cancer is follicular lymphoma and the maximum weekly dose of the bispecific antibody is 80 mg. In some embodiments, the cancer is DLBCL and the maximum weekly dose of the bispecific antibody is 80 mg. In some embodiments, the cancer is DLBCL and the maximum weekly dose of the bispecific antibody is 160 mg. In some embodiments, the cancer is DLBCL and the maximum weekly dose of the bispecific antibody is 320 mg. In any of these embodiments, or others discussed herein, the cancer patient may have been pretreated with an anti-CD20 monospecific antibody therapy.

Non-Hodgkin Lymphoma (NHL) is the most common hematological malignancy. Among a heterogeneous group of NHLs, 85-90% are of B-cell origin and include follicular lymphoma (FL), diffuse large B-cell lymphoma (DLBCL), mantle cell lymphoma (MCL), marginal zone lymphoma (MZL), and several other B-NHLs. Anti-CD20 antibodies in combination with chemotherapy are the standard of care for the treatment of B-NHLs; however, despite initial responses, many patients relapse, often with progressively shorter response durations in subsequent lines of therapy and poor outcomes. Thus, in some embodiments, the antigen-binding molecule is a bispecific anti-CD3×anti-CD20 that binds to CD3+ T cells and CD20+ B cells, targeting CD20+ tumor cells via T-cell mediated cytotoxicity. In some cases, the anti-CD3×CD20 bispecific antibody is for treatment of a B-cell cancer (e.g., a NHL) in a subject that has failed prior therapy with an anti-CD20 monospecific antibody.

For patients with less than a complete response to CAR-T therapy, the outcomes are generally poor, and there are no standard-of-care therapeutic options. Thus, in some cases, the anti-CD3×CD20 bispecific antibody of the present invention is for treatment of a B-cell cancer (e.g., a NHL such as DLBCL) in a subject that has failed prior CAR-T therapy or is not responsive to prior CAR-T therapy (e.g., anti-CD19 CAR-T therapy).

In some embodiments, the antigen-binding molecule is a bispecific anti-CD3×anti-PSMA antibody useful for treating a PSMA-expressing cancer including prostate cancer, kidney cancer, bladder cancer, colorectal cancer, and gastric cancer. In some embodiments, the cancer is prostate cancer (e.g., castrate-resistant prostate cancer).

In some embodiments, the antigen-binding molecule is a bispecific anti-CD3×anti-MUC16 antibody useful for treating a MUC16-expressing cancer including ovarian cancer, breast cancer, pancreatic cancer, non-small-cell lung cancer, intrahepatic cholangiocarcinoma-mass forming type, adenocarcinoma of the uterine cervix, and adenocarcinoma of the gastric tract. In some embodiments, the cancer is ovarian cancer.

In some embodiments, the antigen-binding molecule is a bispecific anti-CD3×anti-STEAP2 antibody useful for treating a STEAP2-expressing cancer including prostate cancer, bladder cancer, cervical cancer, lung cancer, colon cancer, kidney cancer, breast cancer, pancreatic cancer, stomach cancer, uterine cancer, and ovarian cancer. In some embodiments, the cancer is prostate cancer (e.g., castrate-resistant prostate cancer).

In some embodiments, the antigen-binding molecule is a bispecific anti-CD3×anti-BCMA antibody useful for treating a BCMA-expressing cancer including multiple myeloma or other B-cell or plasma cell cancers, such as Waldenström's macroglobulinemia, Burkitt lymphoma, and diffuse large B-Cell lymphoma, Non-Hodgkin's lymphoma, chronic lymphocytic leukemia, follicular lymphoma, mantle cell lymphoma, marginal zone lymphoma, lymphoplasmacytic lymphoma, and Hodgkin's lymphoma. In some embodiments, the cancer is multiple myeloma.

Combination Therapies

The present invention provides methods which comprise administering a pharmaceutical composition comprising any of the exemplary antibodies and bispecific antigen-binding molecules described herein in combination with one or more additional therapeutic agents. Exemplary additional therapeutic agents that may be combined with or administered in combination with an antigen-binding molecule of the present invention include, e.g., an anti-tumor agent (e.g. chemotherapeutic agents including melphalan, vincristine (Oncovin), cyclophosphamide (Cytoxan), etoposide (VP-16), doxorubicin (Adriamycin), liposomal doxorubicin (Doxil), obendamustine (Treanda), or any others known to be effective in treating a plasma cell tumor in a subject.). In certain embodiments the second therapeutic agent is a regimen comprising radiotherapy or a hematopoietic stem cell transplant. In certain embodiments, the second therapeutic agent may be an immunomodulatory agent. In certain embodiments, the second therapeutic agent may be a proteasome inhibitor, including bortezomib (Velcade), carfilzomib (Kyprolis), ixazomib (Ninlaro). In certain embodiments the second therapeutic agent may be a histone deacetylase inhibitor such as panobinostat (Farydak). In certain embodiments, the second therapeutic agent may be a monoclonal antibody, an antibody drug conjugate, a bispecific antibody conjugated to an anti-tumor agent, an immune checkpoint inhibitor, or combinations thereof. The pharmaceutical compositions of the present invention (e.g., pharmaceutical compositions comprising bispecific antigen-binding molecule as disclosed herein) may also be administered as part of a therapeutic regimen comprising one or more therapeutic combinations selected from a monoclonal antibody other than those described herein, which may interact with a different antigen on the plasma cell surface, a bispecific antibody, which has one arm that binds to an antigen on the tumor cell surface and the other arm binds to an antigen on a T cell, an antibody drug conjugate, a bispecific antibody conjugated with an anti-tumor agent, a checkpoint inhibitor, for example, one that targets, PD-1 or CTLA-4, or combinations thereof. In certain embodiments, the checkpoint inhibitors may be selected from PD-1 inhibitors, such as pembrolizumab (Keytruda), nivolumab (Opdivo), or cemiplimab. In certain embodiments, the checkpoint inhibitors may be selected from PD-L1 inhibitors, such as atezolizumab (Tecentriq), avelumab (Bavencio), or Durvalumab (Imfinzi)). In certain embodiments, the checkpoint inhibitors may be selected from CTLA-4 inhibitors, such as ipilimumab (Yervoy). Other combinations that may be used in conjunction with an antibody of the invention are described above.

The present invention also includes therapeutic combinations comprising any of the antigen-binding molecules mentioned herein and an inhibitor of one or more of VEGF, Ang2, DLL4, EGFR, ErbB2, ErbB3, ErbB4, EGFRvIII, cMet, IGF1R, B-raf, PDGFR-α, PDGFR-β, FOLH1 (PSMA), PRLR, STEAP1, STEAP2, TMPRSS2, MSLN, CA9, or uroplakin, wherein the inhibitor is an aptamer, an antisense molecule, a ribozyme, an siRNA, a peptibody, a nanobody or an antibody fragment (e.g., Fab fragment; F(ab')$_2$ fragment; Fd fragment; Fv fragment; scFv; dAb fragment; or other engineered molecules, such as diabodies, triabodies, tetrabodies, minibodies and minimal recognition units). The antigen-binding molecules of the invention may also be administered and/or co-formulated in combination with antivirals, antibiotics, analgesics, and/or NSAIDs. The antigen-binding molecules of the invention may also be administered as part of a treatment regimen that also includes radiation treatment and/or conventional chemotherapy.

The additional therapeutically active component(s) may be administered just prior to, concurrent with, or shortly after the administration of an antigen-binding molecule of the present invention; (for purposes of the present disclosure, such administration regimens are considered the administration of an antigen-binding molecule "in combination with" an additional therapeutically active component).

The present invention includes pharmaceutical compositions in which an antigen-binding molecule of the present invention is co-formulated with one or more of the additional therapeutically active component(s) as described elsewhere herein.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Clinical Evaluation and Dose Escalation of a Bispecific Antibody

The below-described clinical study is an open-label, multi-center phase 1 study to investigate the safety and tolerability of REGN1979, an anti-CD20×anti-CD3 bispecific monoclonal antibody, in patients with CD20+ B-cell malignancies previously treated with CD20-directed antibody therapy.

Objectives:

The primary objectives of the study were to assess the safety, tolerability, and dose-limiting toxicities (DLTs) of REGN1979 administered intravenously (IV), and to study the antitumor activity of REGN1979 in expansion cohorts comprising diffuse large B-cell lymphoma (DLBCL) after failure of chimeric antigen receptor T cell (CAR-T) therapy, aggressive lymphoma (other than DLBCL after failure of CAR-T therapy), follicular lymphoma (FL) grade 1-3a, and chronic lymphocytic leukemia (CLL). The secondary objectives of the study were: (1) to characterize the pharmacokinetic (PK) profile of REGN1979; (2) to assess the immunogenicity of REGN1979; (3) to study the preliminary antitumor activity of REGN1979 administered to patients with CD20+ B-cell malignancies (non-Hodgkin lymphoma [NHL] previously treated with anti-CD20 antibody therapy, or chronic lymphocytic leukemia [CLL]); and (4) to study the preliminary antitumor activity of REGN1979 in the dose escalation portion of the study. Minimal residual disease (MRD) assessments were made in patients with CLL. The exploratory objectives of the study were to evaluate biomarkers that may correlate with mechanism of action, observed toxicity, and potential anti-tumor activity including, but not limited, to: (1) cytokine profiling and assessment of inflammatory markers (e.g., C-reactive protein [CRP]); (2) peripheral blood B-cell and T-cell subsets and immune phenotyping; and (3) changes in gene expression in peripheral blood.

Study Design:

Patients were assigned to a dose level (DL) cohort that consists of an initial starting dose, followed by higher step-up doses for second and subsequent dose administrations. Patients were enrolled based on indication (NHL or CLL). At each DL, there were 2 cohorts (one for each indication), with 3 to 6 patients per NHL cohort, and 1 to 6 patients per CLL cohort. Patients with small lymphocytic lymphoma (SLL) were enrolled in the CLL arm and follow NHL assessments.

Patients who initially showed a clinical benefit and who subsequently relapsed or progressed or had a suboptimal response to treatment may have been re-treated with REGN1979 at the highest DL that was deemed tolerable at the time of relapse or progression.

Patients underwent screening procedures to determine eligibility within 28 days prior to the initial administration of REGN1979. Patients were enrolled sequentially based on indication (NHL or CLL) in order of confirmation of eligibility by the sponsor until each cohort was filled per protocol criteria.

There were separate independent dose escalation cohorts for NHL and CLL at each DL. Each DL consisted of an initial dose and a second and subsequent dose, which was higher than the starting dose, provided the initial dose was tolerated.

Dose escalation followed a traditional 3+3 dose escalation design for patients with NHL. Three to 6 patients were planned per cohort based on observed toxicity.

Dose escalation followed a modified 3+3 with an accelerated titration component for patients with CLL. Based on observed toxicity, 1 to 6 patients were planned per cohort.

Upon completion of the dose escalation phase, and upon determination of a recommended dose for further study in patients with NHL, three expansion cohorts were to be opened for 1) patients with DLBCL after failure of CAR-T therapy (20 patients), 2) aggressive lymphoma (other than DLBCL after failure of CAR-T therapy) (40 patients; among whom 20 patients were to be enrolled each into aggressive lymphoma cohort 1 [160 mg step-up dose]), and cohort 2 [80 mg step-up dose]), and 3) patients with relapsed/refractory follicular lymphoma grade 1-3a (60 patients; among whom 30 were to be enrolled each into cohort 1 [80 mg step-up dose] and cohort 2 [160 mg step-up dose]). The weekly step-up dose of REGN1979 for each of these expansion cohorts (except for aggressive lymphoma cohort 2 and follicular lymphoma cohort 1) was set at 160 mg weekly, followed by Q2W maintenance treatment with 320 mg REGN1979. In the aggressive lymphoma cohort 2 and follicular lymphoma cohort 1, the weekly step-up dose of REGN1979 was 80 mg, and the Q2W maintenance dose of REGN1979 was 160 mg For patients assigned to a step-up dose of 80 mg, patients received 80 mg weekly during a 4-week induction period, after the initial dose escalation, followed by an additional 8 weekly doses, and 160 mg Q2W treatment through progression, with an option to discontinue treatment after the patient has shown a durable response for at least 9 months after the initial demonstration of a CR. For patients assigned to a step-up dose of 160 mg, patients received 160 mg weekly during a 4-week induction period, after the initial dose escalation, followed by an additional 8 weekly doses, and 320 mg Q2W treatment through progression, with an option to discontinue treatment after the patient has shown a durable response for at least 9 months after the initial demonstration of a CR.

The utility of a rituximab lead-in dose prior to the first administration of REGN1979 was studied in patients with NHL to determine whether this intervention can decrease the incidence and severity of infusion-related reaction (IRR) and cytokine release syndrome (CRS). In the rituximab lead-in cohort, REGN1979 was administered using a step-up dose of 160 mg during weekly treatment and 320 mg during Q2W maintenance treatment. Subsequently, an additional 24 patients were to be treated with the optimal dose regimen and dose; together with the 6 patients in the rituximab lead-in group treated at the optimal dose a total of 30 patients were reviewed for safety and tolerability.

In the first DL for the dose escalation portion, there was a required 48-hour waiting period between initial study drug administrations for the first 3 patients within the same indication. Subsequent patients in the first DL were not treated on the same day, regardless of indication. In subsequent cohorts, provided there was no unexpected toxicity observed in previous cohorts or within the cohort, the initial infusions for the first 3 patients were administered at least 24 hours apart.

After each cohort of patients was enrolled, treated, and completed the DLT observation period, opening of subsequent DL cohorts for enrollment (or expansion of the current open DL cohort) was determined once the safety data had been reviewed by both the sponsor and the investigator(s).

The DLT observation period was defined as the first 28 days of treatment, which in this study corresponds with the induction period. During induction, patients were treated with 4 weekly administrations of REGN1979.

In order to be DLT evaluable, an individual patient must have received at least the first 2 administrations of REGN1979 (week 1 day 1 ["initial or primary dose"] and week 2 day 1 ["secondary and subsequent dose"]), or experienced a DLT. Patients enrolled to DL11 and above must have received at least the first 3 administrations of REGN1979 (week 1 initial dose, week 2 intermediate or secondary dose, and week 3 higher tertiary or step-up dose), or experienced a DLT. Additionally, the patient must have been evaluated for at least 28 days from the first administration, and at least 21 days from the second administration.

Dose escalation and cohorts for the NHL and CLL patients are shown in Table 1, below.

TABLE 1

Dose Escalation and Cohorts

| Dose Level | Initial Dose (mcg) | Intermediate Dose (mcg) | Maximum Dose (Step-up dose) (mcg) | NHL | n | CLL | n |
|---|---|---|---|---|---|---|---|
| DL1 | 30 | — | 100 | Cohort 1 | 3-6 | Cohort 1 | 1-6 |
| DL2 | 100 | — | 300 | Cohort 2 | 3-6 | Cohort 2 | 1-6 |
| DL3 | 300 | — | 1000 | Cohort 3 | 3-6 | Cohort 3 | 1-6 |
| DL4 | 1000 | — | 2000 | Cohort 4 | 3-6 | Cohort 4 | 1-6 |
| DL5 | 1000 | — | 3000 | Cohort 5 | 3-6 | Cohort 5 | 1-6 |
| DL6 | 1000 | — | 4000 | Cohort 6 | 3-6 | Cohort 6 | 1-6 |
| DL7 | 1000 | — | 5000 | Cohort 7 | 3-6 | Cohort 7 | 1-6 |
| DL8 | 1000 | — | 6000 | Cohort 8 | 3-6 | Cohort 8 | 1-6 |
| DL9 | 1000 | — | 7000 | Cohort 9 | 3-6 | Cohort 9 | 1-6 |
| DL10 | 1000 | — | 8000 | Cohort 10 | 3-6 | Cohort 10 | 1-6 |
| DL11 | 1000 | 6,000 | 12,000 | Cohort 11 | 3-6 | Cohort 11 | 1-6 |
| DL12 | 1000 | 9,000 | 18,000 | Cohort 12 | 3-6 | Cohort 12 | 1-6 |
| DL13 | 1000 | 13,500 | 27,000 | Cohort 13 | 3-6 | Cohort 13 | 1-6 |
| DL14 | 1000 | 20,000 | 40,000 | Cohort 14 | 3-6 | Cohort 14 | 1-6 |
| DL15 | 1000 | 20,000 | 80,000 | Cohort 15 | 3-6 | Cohort 15 | 1-6 |
| DL16 | 1000 | 20,000 | 160,000 | Cohort 16 | 3-6 | Cohort 16 | 1-6 |
| DL17 | 1000 | 20,000 | 320,000 | Cohort 17 | 3-6 | Cohort 17 | 1-6 |

In this study, each dose level comprises an initial REGN1979 dose followed by a step-up dose; for cohorts DL11 and above, a secondary dose has been added prior to reaching the step-up dose (see Table 1). The initial (primary) dose, the intermediate (secondary) dose (if applicable), and the first administration of the step-up (tertiary) dose are each optionally split over at least 2 days. All patients in the DL7 and higher maximum dose cohorts received split dosing (e.g., fractionated dosing) for initial (primary) and intermediate (secondary) doses. Patients in DL11 and higher maximum dose cohorts received split dosing (e.g., fractionated dosing) for initial (primary), intermediate (secondary) and first step-up (tertiary) doses, followed by step-up doses (maximum weekly dose) thereafter.

Study Duration:

The treatment period is 9 months. Patients will be treated with up to 24 doses of REGN1979—4 weekly doses during a 4-week induction period, followed by an additional 8 weekly doses, and 12 or more doses administered twice-monthly (Q2W) during a maintenance period through progression, with an option to discontinue treatment following 9 months after patient achieved a complete response. Patients may be followed for efficacy and safety for up to 15 months after end of treatment.

Study Population:

Assuming enrollment through DL17 and complete enrollment into all expansion cohorts, up to 370 patients are planned at approximately 15 sites across the United States and Germany. Up to 204 patients will be enrolled in the dose escalation cohorts through DL17 for both indications (NHL and CLL) during the dose escalation phase. Up to 100 patients comprising 90 NHL patients (20 DLBCL patients after failure of CAR-T therapy, 40 aggressive lymphoma patients [other than DLBCL after failure of CAR-T therapy], 30 FL grade 1-3a patients), and 10 CLL patients will be enrolled in the disease-specific expansion cohorts. Up to 42 patients will be enrolled in the rituximab lead-in cohort to determine the optimal dose regimen. Once the optimal rituximab lead-in dose regimen is determined, an additional 24 patients will be enrolled into the rituximab lead-in expansion and will be combined with the 6 patients from the above rituximab lead-in group treated with the optimal dose regimen and dose. Thus, a total of 30 patients will be evaluated at the optimal rituximab lead-in dose regimen and dose.

Patients must have documented CD20+ B-cell malignancy, with active disease not responsive to prior therapy, for whom no standard of care options exists, and for whom treatment with an anti-CD20 antibody may be appropriate. Patients with NHL must have previously been treated with CD20-directed antibody therapy.

Inclusion Criteria:

A patient must meet the following criteria to be eligible for inclusion in the study:

1. Have documented CD20+ B-cell malignancy, with active disease not responsive to prior therapy, for whom no standard of care options exists, and for whom treatment with an anti-CD20 antibody may be appropriate:
   B-NHL confirmed by NCI working group criteria, 2007 (Cheson 2007, Appendix 2); and
   CLL confirmed by the International Workshop on Chronic Lymphocytic Leukemia (IWCLL) working group criteria, 2008 (Hallek 2008, Appendix 3)—Patients with small lymphocytic lymphoma (SLL) will be enrolled in the CLL arm and follow NHL assessments.
   Note—A patient with CD20-negative lymph node (NHL) biopsy performed as standard of care just prior to enrollment, remains eligible for the study provided the patient had previously documented CD20+ disease AND was previously treated with rituximab or other CD20-directed antibody therapy within approximately 6 months. Individual cases may be discussed with the medical monitor.

2. Patients with NHL must have had prior treatment with an anti-CD20 antibody therapy. Patients with CLL are not required to have received prior treatment with an anti-CD20 antibody therapy, provided the patient has failed either a BTK inhibitor or PI3K inhibitor and the treating physician deems it appropriate for the patient to be entered into a phase 1 trial. For inclusion in FL grade 1-3a expansion cohort, patients must have received at least 2 prior lines of systemic therapy, including an anti-CD20 antibody and an alkylating agent. For the inclusion in the disease-specific expansion cohort enrolling DLBCL patients after failure of CAR-T therapy, the patient must have recovered from the toxicities of the lymphodepletion therapy and CAR-T infusion. There is no requirement for the prior CAR-T therapy to be the most recent line of therapy before study enrollment.

3. All patients (B-cell NHL and CLL) must have at least one bi-dimensionally measurable lesion≥1.5 cm) documented by CT or MRI scan, if CT scan is not feasible.

4. Patients with CLL must have white blood cell (WBC) ≤200×109/L

5. Age≥18 years

6. Eastern Cooperative Oncology Group (ECOG) performance status≤1

7. Life expectancy of at least 6 months

8. Adequate bone marrow function documented by: a. Platelet counts≥75×109/L; b. Hb level≥9 g/dL; c. ANC≥1× 109/L
   Note—Patients with cell counts below thresholds listed above may be considered for enrollment if, in the opinion of the investigator, the reason is believed to be due to bone marrow infiltration by underlying disease. In such cases, the investigator must discuss the eligibility with the sponsor and receive approval for enrollment in writing.

9. Adequate organ function documented by:
   Aspartate aminotransferase (AST) and alanine aminotransferase (ALT)≤2.5×ULN
   Total bilirubin≤1.5×ULN
   Note—Patients with Gilbert's syndrome do not need to meet this requirement provided their total bilirubin is unchanged from their baseline.
   Calculated creatinine clearance by Cockcroft-Gault≥50 mL/min
   Note—Patients may be considered for enrollment if, in the opinion of the investigator, the abnormal laboratory results are due to underlying disease. In such cases, the investigator must discuss the eligibility with the sponsor and receive approval for enrollment in writing.
   Note—Patients with borderline creatinine clearance by Cockcroft-Gault may be considered for enrollment if a measured creatinine clearance (based on 24-hour urine or other reliable method) is ≥50 mL/min.

10. Willingness to undergo mandatory tumor biopsy pretreatment, if in the opinion of the investigator, the patient has an accessible lesion that can be biopsied without significant risk to the patient.

11. Willing and able to comply with clinic visits and study-related procedures

12. Provide signed informed consent.

Exclusion Criteria:

A patient who meets any of the following criteria will be excluded from the study:

1. Primary central nervous system (CNS) lymphoma or known or suspected CNS involvement by non-primary CNS NHL 2. History of or current relevant CNS pathology such as
   Epilepsy, seizure, paresis, aphasia, apoplexia, severe brain injuries, cerebellar disease, organic brain syndrome, psychosis, or
   Evidence for presence of inflammatory lesions and/or vasculitis on cerebral MRI 3. Standard anti-neoplastic chemotherapy (non-biologic) within 5-times the half-life or within 28 days, whichever is shorter, prior to first administration of study drug.

4. Standard radiotherapy within 14 days of first administration of study drug.
   Note—Palliative radiotherapy to a symptomatic lymph node/lesion is allowed provided the irradiated lesion(s) or node(s) is not included as a target lesion for tumor assessments 5. Allogeneic stem cell transplantation 6. Treatment with rituximab, alemtuzumab or other investigational or commercial biologic agent within 12 weeks prior to first administration of study drug.
   Note—for patients with aggressive lymphoma for which immediate treatment is required, the wash-out period may be reduced to 28 days. This will require discussion with and approval by the sponsor in writing.

7. Immunosuppressive therapy (other than biologic) within 28 days of first administration of study drug.

8. Treatment with an investigational non-biologic agent within 28 days of first administration of study drug.

9. History of allergic reactions attributed to compounds of similar chemical or biologic composition of study drug.

10. History of hypersensitivity to any compound in the tetracycline antibiotics group.

11. Concurrent active malignancy for which the patient is receiving treatment.

12. Known active bacterial, viral, fungal, mycobacterial or other infection or any major episode of infection requiring hospitalization or treatment with IV anti-infectives within 4 weeks of first administration.

13. Evidence of significant concurrent disease or medical condition that could interfere with the conduct of the study, or put the patient at significant risk including, but not limited to, significant cardiovascular disease (eg, New York Heart Association Class III or IV cardiac disease, myocardial infarction within the previous 6 months, unstable arrhythmias or unstable angina) and/or significant pulmonary disease (eg, obstructive pulmonary disease and history of symptomatic bronchospasm).

Note—Patients with a medical history of cardiac disease should be evaluated by ECHO or multigated acquisition scan (MUGA) prior to first administration of REGN1979 to ensure adequate cardiac reserves and function.

14. Ongoing systemic corticosteroid treatment, with the exception of corticosteroid use for other (non-tumor and non-immunosuppressive) indications up to a maximum of 10 mg/day of prednisone or equivalent.

15. Infection with human immunodeficiency virus (HIV) or chronic infection with hepatitis B virus (HBV) or hepatitis C virus (HCV). Patients with hepatitis B (HepBsAg+) who have controlled infection (serum hepatitis B virus DNA that is below the limit of detection AND receiving anti-viral therapy for hepatitis B) are permitted upon consultation with the physician managing the infection.

16. Known hypersensitivity to both allopurinol and rasburicase.

17. Pregnant or breast-feeding women.

18. Women of childbearing potential* who are unwilling to practice highly effective contraception prior to the initial study drug treatment, during the study, and for at least 6 months after the last dose. Highly effective contraceptive measures include stable use of combined (estrogen and progestogen containing) hormonal contraception (oral, intravaginal, transdermal) or progestogen-only hormonal contraception (oral, injectable, implantable) associated with inhibition of ovulation initiated 2 or more menstrual cycles prior to screening; intrauterine device; intrauterine hormone-releasing system; bilateral tubal ligation; vasectomized partner; and or sexual abstinence †, ‡,

* Postmenopausal women must be amenorrheic for at least 12 months in order not to be considered of child bearing potential. Pregnancy testing and contraception are not required for women with documented hysterectomy or tubal ligation.

† Sexual abstinence is considered a highly effective method only if defined as refraining from heterosexual intercourse during the entire period of risk associated with the study treatments. The reliability of sexual abstinence needs to be evaluated in relation to the duration of the clinical trial and the preferred and usual lifestyle of the patient.

‡ Periodic abstinence (calendar, symptothermal, post-ovulation methods), withdrawal (coitus interruptus), spermicides only, and lactational amenorrhoea method (LAM) are not acceptable methods of contraception. Female condom and male condom should not be used together.

19. Administration of live vaccination within 28 days of first administration of study drug 20. Member of the clinical site study team and/or his/her immediate family, unless prior approval is granted by the Sponsor.

Treatments:

REGN1979 was supplied as a liquid in sterile, single-use vials. Each vial contained REGN1979 at a concentration of 2 mg/mL. Detailed preparation and administration instructions were provided to the sites in the pharmacy manual. Diluent was supplied for REGN1979 study drug preparation.

Patients received REGN1979 weekly during a 4-week induction period, followed by another 8 weekly doses, and Q2W doses until progression, at a dose per their assigned cohort.

In the rituximab lead-in cohort and expansion only, a single dose of rituximab (375 mg/m$^2$) was administered one day prior to the first dose of REGN1979 [i.e, on study day (−1)]. REGN1979 was started on Week 1 Day 1, and the treatment period for REGN1979 was 9 months. Patients were treated with up to 24 doses of REGN1979: 4 weekly doses during a 4-week induction period, followed by an additional 8 weekly doses, and 12 or more doses administered Q2W during a maintenance period, until progression. In the rituximab lead-in cohort, REGN1979 was administered using a step-up dose of 160 mg during weekly treatment and 320 mg during Q2W maintenance treatment. Dose groups with step-up doses of REGN1979 below 160 mg weekly treatment and below 320 mg REGN1979 Q2W maintenance treatment may be evaluated also. Subsequently, an additional 24 patients were evaluated with the optimal dose regimen and dose; together with the 6 patients in the rituximab lead-in group treated with the optimal dose regimen and dose, a total of 30 patients were reviewed for safety and tolerability.

Endpoints

Primary:

The primary endpoints were safety (specifically, adverse events [AEs] and DLTs) to determine the maximum tolerated dose (MTD) and/or optimal biological dose (OBD) as recommended phase 2 dose (RP2D) of REGN1979; and efficacy as measured by the objective response rate (ORR) in the expansion cohort of DLBCL patients after failure of CAR-T therapy, aggressive lymphoma (other than DLBCL after failure of CAR-T therapy) expansion cohorts 1 and 2, the FL grade 1-3a expansion cohort, and the CLL expansion cohort.

Secondary:

The secondary endpoints were:

Pharmacokinetics: Concentration of REGN1979

Immunogenicity: Anti-REGN1979 antibodies

Antitumor activity:
  Objective response rate (ORR)
    Tumor response assessment per the Revised Response Criteria for Malignant Lymphoma of the NCI-International Working Group (NCI-WG)
    Tumor response assessment as per the International Workshop on Chronic Lymphocytic Leukemia Guidelines for the Diagnosis and treatment of CLL
    For patients enrolled into NHL expansion cohorts, tumor response assessment as per the Lugano Classification
  Progression free survival (PFS) and overall survival (OS)
  Minimal residual disease (MRD) for patients with CLL The exploratory endpoints include:

Pharmacodynamic (PD) measures including:
  B-cell and T-cell subsets and phenotype
  Circulating cytokine levels
  CRP
  Changes in gene expression in peripheral blood Procedures and Assessments Baseline Procedures:

Brain MRI, electrocardiogram (ECG), human immunodeficiency virus (HIV), hepatitis C virus (HCV), and hepatitis B virus (HBV) testing, and coagulation. Safety procedures: Medical history, physical examination, assessment of symptoms, evaluation of performance status, clinical laboratory tests, vital signs, AEs, and concomitant medications.

Efficacy Procedures:

Tumor assessments, including CT or MRI scans, 18F-fluorodeoxyglucose-positron emission tomography (FDG-PET) scans, bone marrow aspirate and biopsies, lymph node and/or tumor biopsies, and peripheral blood samples (CLL patients only). Blood samples for PK and anti-drug antibody (ADA) assessment were collected.

Biomarkers samples were collected to monitor for changes in cytokine production, serum levels of pro-inflammatory cytokines, and changes in lymphocyte subsets and activation status. In addition, these samples permitted tumor or somatic genetic analyses for variations that impact the clinical course of underlying disease or modulate treatment side effects.

Statistical Plan:

The study design was based on a traditional 3+3 design with 3 to 6 patients per DL for patients with NHL, and a modified 3+3 design with an accelerated titration component with 1 to 6 patients per DL for patients with CLL. The exact number of patients enrolled will depend on the number of patients (NHL and CLL) observed with protocol-defined DLTs and grade 2 or higher treatment-related toxicity in which acute effects (with the exception of associated laboratory abnormalities) resolve to grade 1 or baseline within 72 hours (CLL during the accelerated titration component), and the need to expand currently defined DLs, or open additional cohorts at lower DLs.

Patient enrolment is on-going and up to 370 patients are planned. Up to 204 patients will be enrolled in the dose escalation cohorts through DL17 for both indications (NHL and CLL) during the dose escalation phase. Up to 100 patients comprising 90 NHL patients (20 DLBCL patients after failure of CAR-T therapy, 40 aggressive lymphoma patients [other than DLBCL after failure of CAR-T therapy], and 30 FL grade 1-3a patients), and 10 CLL patients will be enrolled in the disease-specific expansion cohorts. Up to 42 patients will be enrolled in the rituximab lead-in cohort to determine the optimal dose regimen. An additional 24 patients will be enrolled into a rituximab lead-in expansion and will be combined with the 6 patients from the above rituximab lead-in cohort treated with the optimal dose regimen and dose. Thus, a total of 30 patients will be evaluated at the at the optimal rituximab lead-in dose regimen and dose.

Data is summarized using descriptive statistics only. In general, data is summarized by DL, and by indication (NHL or CLL). Within the NHL indication, data will also by summarized by the subgroups and dose of DLBCL after failure of CAR-T therapy, aggressive lymphoma (other than DLBCL after failure of CAR-T therapy) cohorts 1 and 2, and FL grade 1-3a. Within the NHL indication, data is also summarized by the subgroups of indolent and aggressive NHL. Demographic and baseline characteristics is summarized descriptively by group.

The safety summaries and analyses were performed on the safety analysis set (SAF). The primary analysis of safety was based on treatment-emergent AEs (TEAEs). This analysis comprised the basis upon which conclusions were drawn regarding the safety profile of REGN1979. All AEs reported in this study were coded using the currently available version of the Medical Dictionary for Regulatory Activities (MedDRA®). Coding will be to lowest level terms. The verbatim text, the preferred term (PT), and the primary system organ class (SOC) was listed. The analysis for efficacy and baseline variables is performed on the efficacy analysis set (FAS). The efficacy analyses for the expansion cohorts comprising DLBCL after failure of CAR-T therapy, aggressive lymphoma (other than DLBCL after failure of CAR-T therapy) cohorts 1 and 2, FL grade 1-3a, and CLL will be performed separately after all the patients in the respective cohort have completed the 24-week visit or have discontinued from the study prior to this time.

Results:

Results for patients that were administered a maximum weekly dose of 5 to 320 mg indicate a low incidence of CRS. Serum concentrations of REGN1979 in patients receiving a maximum weekly dose of as little as 12 mg were observed to approach or exceed serum concentration levels that have been demonstrated to be effective in Raji tumor xenograft mouse models (data not shown). Patients receiving a maximum weekly dose of as little as 40 mg maintained a serum concentration exceeding the minimum concentration level (2000 μg/L) demonstrated to be effective in the Raji tumor xenograft mouse models (data not shown). In addition, numerous partial and complete responses were also observed in the patients treated at these levels, as shown in Tables 2-9, below. The cumulative REGN1979 safety and PK experience through the DLT evaluation period of Cohort 13N (27,000 mcg REGN1979) demonstrates that the management algorithm for CRS or IRR reactions (i.e., incremental dose escalation, split dosing during the initial weeks of REGN1979 administration, and premedication with corticosteroid) has proved effective in preventing severe CRS or IRR despite incremental increases in dosing in successive dose cohorts. Split dosing provided a benefit to patient safety in weeks 1 through 4 (the available data), wherein less overall incidents of severe CRS/IRR were observed. Particularly, the dosing strategy discussed herein provided a safer strategy for escalating doses to levels greater than 80 mg, even 160 mg or greater, with less severe events occurring in weeks 3 and 4 when higher doses reached and exceeded the desired serum concentrations discussed above. FIG. 1 illustrates the incidence of CRS/IRR for patients receiving up to a maximum dose of 320 mg. To date, no patients have been discontinued due to a CRS/IRR adverse event.

TABLE 2

Observed Response in Follicular Lymphoma Grade 1-3a

| | CD20 × CD3[†] | | | |
|---|---|---|---|---|
| | <5 mg (N = 7) | 5-12 mg (N = 5) | 18-40 mg (N = 6) | 160 mg (N = 1) |
| Overall response rate, n (%) | 1 (14.3) | 5 (100) | 5 (83.4) | 1 (100) |
| Complete response, n (%) | 1 (14.3) | 4 (80) | 4 (66.7) | 0 |
| Partial response, n (%) | 0 | 1 (20) | 1 (16.7) | 1 (100) |
| Stable disease, n (%) | 4 (57.1) | 0 | 1 (16.7) | 0 |
| Progressive disease, n (%) | 2 (28.6) | 0 | 0 | 0 |
| Duration of response, median (95% CI), months | 5.3 N/A | N/A (5.75-not reached) | 11.8 (4.37-11.83) | N/A |

[†]No patients dosed at 80 mg REGN1979

After data cut-off (Table 2), two additional evaluable patients showed complete responses (CRs), one at 40 mg and the second at 320 mg.

TABLE 3

Observed Response in Diffuse Large B-Cell Lymphoma

| | CD20 × CD3 | | | | | |
|---|---|---|---|---|---|---|
| | <5 mg (N = 15) | 5-12 mg (N = 11) | 18-40 mg (N = 11) | 80 mg (N = 3) | 160 mg (N = 3) | 320 mg (N = 2) |
| Overall response rate, n (%) | 2 (13.3) | 2 (18.2) | 6 (54.5) | 3 (100) | 1 (33.3) | 1 (50.0) |
| Complete response, n (%) | 0 | 1 (9.1) | 2 (18.2) | 3 (100) | 1 (33.3) | 1 (50.0) |
| Partial response, n (%) | 2 (13.3) | 1 (9.1) | 4 (36.4) | 0 | 0 | 0 |
| Stable disease, n (%) | 4 (26.7) | 4 (36.4) | 3 (27.3) | 0 | 1 (33.3) | 1 (50.0) |
| Progressive disease, n (%) | 8 (53.3) | 4 (36.4) | 1 (9.1) | 0 | 1 (33.3) | 0 |
| Missing/Unable to Evaluate, n (%) | 1 (6.7) | 1 (9.1) | 1 (9.1) | 0 | 0 | 0 |
| Duration of response, median (95% CI), months | 2.1 (1.5-2.6) | N/A | 4.4 (2.5-not reached) | N/A | N/A | N/A |

Two of three 80 mg patients with CR were CAR T-cell therapy failures. All of the complete responses noted in Table 3 were complete metabolic responses.

All CRs at 80 mg, 160 mg and 320 mg doses are on-going CRs on study treatment, pointing to the durability of response.

TABLE 4

Observed Response in DLBCL After CAR-T Therapy Failure

| | CD20 × CD3 | | | | |
|---|---|---|---|---|---|
| | 3 mg (N = 1) | 27 mg (N = 1) | 40 mg (N = 1) | 80 mg (N = 3) | 160 mg (N = 1) |
| Overall response rate, n (%) | 0 | 0 | | 2 (66.7) | |
| Complete response, n (%) | 0 | 0 | | 2 (66.7) | |
| Partial response, n (%) | 0 | 0 | | 0 | |
| Stable disease, n (%) | 0 | 1 (100) | | 0 | |
| Progressive disease, n (%) | 1 (100) | 0 | 1 (100) | 1 (33.3) | 1 (100) |
| Missing/Unable to Evaluate, n (%) | 0 | 0 | | 0 | |

TABLE 5

Observed Response in Mantle Cell Lymphoma

| | CD20 × CD3 | | |
|---|---|---|---|
| | 5-12 mg (N = 1) | 18-40 mg (N = 1) | 160 mg (N = 1) |
| Objective Response (CR/PR) | 1 (100%) | 1 (100%) | 0 |
| Complete response | 0 | 1 (100%) | 0 |
| Partial response | 1 (100%) | 0 | 0 |
| Stable disease | 0 | 0 | 0 |
| Progressive disease | 0 | 0 | 0 |
| Missing/Unable to Evaluate | 0 | 0 | 1 (100%) |

TABLE 6

Observed Response in Marginal Zone Lymphoma

| | CD20 × CD3 | | |
|---|---|---|---|
| | 5-12 mg (N = 1) | 18-40 mg (N = 1) | 80 mg (N = 3) |
| Objective Response (CR/PR) | 0 | 1 (100%) | 2 (66.7%) |
| Complete response | 0 | 0 | 2 (66.7%) |
| Partial response | 0 | 1 (100%) | 0 |
| Stable disease | 0 | 0 | 0 |
| Progressive disease | 1 (100%) | 0 | 1 (33.3%) |

TABLE 7

Responses in Patients with MCL by Dose Level

| | CD20 × CD3 | | | | | |
|---|---|---|---|---|---|---|
| | 0.3 mg (N = 1) | 2 mg (N = 1) | 4 mg (N = 1) | 8 mg (N = 1) | 27 mg (N = 1) | 160 mg (N = 1) |
| Objective Response (CR/PR) | 0 | 1 (100%) | 0 | 1 (100%) | 1 (100%) | 1 (100%) |
| Complete Response | 0 | 0 | 0 | 0 | 1 (100%) | 1 (100%) |
| Partial Response | 0 | 1 (100%) | 0 | 1 (100%) | 0 | 0 |
| Stable disease | 0 | 0 | 0 | 0 | 0 | 0 |
| Progressive disease | 1 (100%) | 0 | 1 (100%) | 0 | 0 | 0 |
| Missing/Unable to Evaluate | 0 | 0 | 0 | 0 | 0 | 0 |

TABLE 8

Responses in Patients with MZL by Dose Level

| | CD20 × CD3 | | | |
|---|---|---|---|---|
| | 4 mg (N = 1) | 5 mg (N = 1) | 27 mg (N = 1) | 80 mg (N = 3) |
| Objective Response (CR/PR) | 1 (100%) | 0 | 1 (100%) | 2 (66.7%) |
| Complete Response | 0 | 0 | 0 | 2 (66.7%) |
| Partial Response | 1 (100%) | 0 | 1 (100%) | 0 |
| Stable disease | 0 | 0 | 0 | 0 |
| Progressive disease | 0 | 1 (100%) | 0 | 1 (33.3%) |

TABLE 8-continued

Responses in Patients with MZL by Dose Level

| | CD20 × CD3 | | | |
|---|---|---|---|---|
| | 4 mg (N = 1) | 5 mg (N = 1) | 27 mg (N = 1) | 80 mg (N = 3) |
| Missing/Unable to Evaluate | 0 | 0 | 0 | 0 |

TABLE 9

Responses in Patients with Other-NHL by Dose Level

| | CD20 × CD3 | | | |
|---|---|---|---|---|
| | 4 mg (N = 1) | 12 mg (N = 1) | 18 mg (N = 1) | 27 mg (N = 1) |
| NHL Subtype | FL grade unknown | Waldenstrom Macroglobulinemia | FL grade 3b | FL grade unknown |
| Objective Response (CR/PR) | 0 | 0 | 1 (100%) | 0 |
| Complete Response | 0 | 0 | 1 (100%) | 0 |
| Partial Response | 0 | 0 | 0 | 0 |
| Stable disease | 1 (100%) | 0 | 0 | 0 |
| Progressive disease | 0 | 0 | 0 | 0 |
| Missing/Unable to Evaluate | 0 | 1 (100%) | 0 | 1 (100%) |

In general, activity observed broadly in heavily pretreated relapsed/refractory B-NHL patients treated with REGN1979, including some with progression after prior CAR T-cell therapy, included:
(i) FL Grade 1-3a: 12/13 (92.3%) ORR; 8/13 CR (61.5%) at doses≥5 mg;
(ii) DLBCL: 4/6 (66.7%) ORR (all CR) at doses of 80-160 mg, with two patients achieving CR after failure of CD19 directed CAR T-cell therapy;
(iii) MCL: 3/3 responses at doses≥5 mg, including one CR;
(iv) MZL: 3/5 response at doses≥5 mg, including two CRs;
(v) Tolerability in patients with B-NHL has been demonstrated up to doses of 320 mg weekly, with no observed DLTs in patients with B-NHL;
(vi) Majority of adverse events with mild to moderate in severity;
(vii) Infections were reported in 49.4% of patients (14.8% Grade 3-4, with two deaths (2.5%));
(viii) No patient discontinued treatment due to CRS or neurologic adverse events. Of 96 initial patients, only seven patients experienced Grade 3 CRS; and
(ix) Dexamethasone did not inhibit cytotoxicity of REGN1979, modestly affected upregulation of T-cell activation, and inhibited cytokine release.

Example 2: Clinical Evaluation of a Bispecific Antibody

The below-described clinical study is an open-label multicenter phase 2 study to assess the anti-tumor activity and safety of REGN1979, an anti-CD20×anti-CD3 bispecific antibody, in patients with relapsed or refractory follicular lymphoma.

Objectives:
The primary objective of this study is to assess the anti-tumor activity of single agent REGN1979, as measured by objective response rate (ORR) according to the Lugano Classification of response in malignant lymphoma (Cheson, 2014) by independent central review, in patients with follicular lymphoma (FL) that has relapsed or is refractory to at least 2 prior lines of systemic therapy, including an anti-CD20 antibody and an alkylating agent. The secondary objectives in this study are: (1) to assess the anti-tumor activity of single agent REGN1979 in patients with relapsed or refractory FL, as measured by (a) ORR according to the Lugano Classification (Cheson, 2014) as assessed by local investigator evaluation, (b) complete response (CR) rate according to the Lugano Classification as assessed by independent central review, and local investigator evaluation, (c) progression free survival (PFS) according to Lugano Classification as assessed by independent central review, and local investigator evaluation, (d) overall survival (OS), (e) duration of response (DOR) according to the Lugano Classification as assessed by independent central review, and local investigator evaluation, (f) disease control rate (DCR) according to the Lugano Classification as assessed by independent central review, and local investigator evaluation, (g) duration of disease control (DDC) according to the Lugano Classification as assessed by independent central review, and local investigator evaluation; (2) to evaluate the safety and tolerability of REGN1979; (3) to assess the pharmacokinetics (PK) of REGN1979; (4) to assess the immunogenicity of REGN1979; and (5) to assess the effect of REGN1979 on quality of life as measured by the validated instruments European Organisation for Research and Treatment of Cancer Quality of Life Questionnaire (EORTC QLQ-C30) and EuroQoL 5 Dimensions 3 Levels (EQ-5D-3L).

Study Design:
the study consists of a screening period of up to 28 days, a total treatment period of up to 98 weeks that includes 12 weekly (QW) doses followed by every 2-week (Q2W) dosing of up to 86 weeks, and a post-treatment follow-up period of 96 weeks.

REGN1979 is administered as a single agent intravenously (IV) at an initial (primary) dose of 1 mg, followed by an intermediate (secondary) dose of 20 mg, and subsequently by a nominal (tertiary and maximum weekly) dose of 80 mg in a dosing regimen of 12 QW treatments, followed by dosing of 80 mg REGN1979 Q2W.

Enrollment follows an open-label, single-arm design.

The screening period begins with the signing of the informed consent form (ICF) and ends when the patient has been confirmed to be eligible for the study and initiates treatment, or with the determination that the patient is ineligible and has been designated as a screen failure.

The treatment period begins with the initial administration of REGN1979 and consists of 12 QW infusions of REGN1979 followed by Q2W dosing for 86 weeks for a total treatment period of 98 weeks of study drug dosing, unless the patient discontinues study treatment due to disease progression, start of subsequent lymphoma therapy, adverse event (AE), or any other reason.

The post-treatment follow-up period will be for 96 weeks after the last dose of study treatment. All patients will be followed every 12 weeks for survival status until death, loss to follow-up, patient withdrawal of consent for follow-up, or study termination by the sponsor, whichever is sooner. For patients who have discontinued study treatment for any reason other than disease progression, start of subsequent lymphoma therapy, or death, disease response will be assessed every 12 weeks during the post-treatment follow-up period until the time of disease progression, death, start of a subsequent lymphoma therapy, or patient withdrawal of consent for follow-up, whichever is sooner.

Study Duration:

The duration of the study for each patient, excluding the screening period, will be approximately 194 weeks unless the patient has disease progression or starts subsequent therapy, or until the time of death, loss to follow-up, patient withdrawal of consent for follow-up, or study termination by the sponsor. The end of study is defined as the last visit of the last patient.

Study Population:

Up to 481 patients will be enrolled at up to 100 sites. The study population will consist of patients aged 18 years and older with previously treated FL grade 1 to 3a that has relapsed or is refractory to at least 2 prior lines of systemic therapy, including an anti-CD20 antibody and an alkylating agent. Central histopathologic confirmation of the FL diagnosis will be required prior to enrollment. Patients with FL grade 3b are ineligible. Refractory disease is defined as lack of response to a standard regimen or progression within 6 months of last treatment.

Inclusion Criteria:

Each patient must meet the following criteria to be eligible for inclusion in the study:

1. Age 18 years or greater

2. Central histopathologic confirmation of the FL Grade 1 to 3a diagnosis must be obtained before study enrollment. Patients with FL grade 3b are ineligible. Follicular lymphoma subtyping is based on the World Health Organization (WHO) classification (Swerdlow, 2017).

3. Disease must have relapsed or must be refractory to ≥2 prior lines of systemic therapy, including an anti-CD20 antibody and an alkylating agent. Patients should in the opinion of the investigator require therapy for FL at the time of study enrollment.

4. Measurable disease on cross sectional imaging (defined as at least 1 bi-dimensionally measurable nodal lesion of ≥1.5 cm in the greatest transverse diameter (GTD) regardless of the short axis diameter) documented by diagnostic imaging (computed tomography [CT], or magnetic resonance imaging [MRI]).

5. Eastern Cooperative Oncology Group (ECOG) performance status 0 or 1.

6. Adequate bone marrow function as documented by: (a) Platelet count≥50×10$^9$/L. A patient may not have received platelet transfusion within 7 days prior to first dose of REGN1979 in order to meet the platelet eligibility criterion; (b) Hemoglobin≥9.0 g/dL; (c) Absolute neutrophil count (ANC)≥1.0×10$^9$/L. A patient may not have received granulocyte colony stimulating factor within 2 days prior to first dose of REGN1979 in order to meet the ANC eligibility criterion.

7. Adequate hepatic function: (a) Total bilirubin≤1.5× upper limit of normal (ULN) (≤3×ULN if attributed to lymphoma infiltration of liver); (b) Alanine aminotransferase (ALT) and aspartate aminotransferase (AST)≤2.5×ULN (≤5×ULN if attributed to lymphoma infiltration of liver); (c) Alkaline phosphatase (ALP)≤2.5×ULN (≤5×ULN if attributed to lymphoma infiltration of liver); NOTES—Irrespective of the presence of lymphoma infiltration of the liver, a patient with an AST>2.5×ULN and/or ALT>2.5×ULN concurrent with a total bilirubin>1.5×ULN will be excluded, and Patients with known Gilbert syndrome are not required to meet this total bilirubin requirement provided that the value is unchanged from the baseline level.

8. Serum creatinine≤1.5×ULN, or calculated creatinine clearance by Cockcroft-Gault formula≥50 mL/min; NOTE—Patients with a calculated creatinine clearance<50 mL/min may be considered for enrollment if a measured creatinine clearance (based on 24-hour urine collection or other reliable method) is ≥50 mL/min.

9. Willingness to undergo tumor biopsy at baseline. If an investigator has determined that a baseline tumor biopsy cannot be obtained safely, the sponsor may grant an exception to the requirement for biopsy only after discussion with and approval by the medical monitor.

10. Ability to understand the purpose and risks of the study and provide signed and dated informed consent and authorization to use protected health information (in accordance with national and local subject privacy regulations).

11. Willing and able to comply with clinic visits and study-related procedures.

12. Provide informed consent signed by study patient or legally acceptable representative.

13. Able to understand and complete study-related questionnaires.

Exclusion Criteria:

A patient who meets any of the following criteria will be excluded from the study:

1. Primary central nervous system (CNS) lymphoma or known involvement by non-primary CNS NHL (suspected CNS lymphoma should be evaluated by lumbar puncture, as appropriate, in addition to the mandatory head CT or MRI).

2. Treatment with any systemic anti-lymphoma therapy within 5 half-lives or within 28 days prior to first administration of study drug, whichever is shorter.

3. History of allogeneic stem cell transplantation.

4. Prior treatment with any chimeric antigen receptor T-cell (CAR-T) therapy.

5. Continuous systemic corticosteroid treatment with more than 10 mg per day of prednisone or anti-inflammatory equivalent within 72 hours of start of study drug.

6. History of neurodegenerative condition or CNS movement disorder. History of uncontrolled seizure disorder, defined as any seizure within 12 months prior to study enrollment.

7. Vaccination within 28 days prior to first study drug administration with a vector that has replicative potential.

8. Another malignancy except FL in the past 5 years, with the exception of non-melanoma skin cancer that has undergone potentially curative therapy or in situ cervical carcinoma, or any other tumor that has been deemed to be effectively treated with definitive local control and with curative intent.

9. Evidence of significant concurrent disease or medical condition that could interfere with the conduct of the study or put the patient at significant risk, including but not limited to significant cardiovascular disease (e.g., New York Heart Association Class III or IV cardiac disease, myocardial infarction within the previous 6 months, unstable arrhythmias, or unstable angina) and/or significant pulmonary disease (e.g., obstructive pulmonary disease and history of symptomatic bronchospasm).

10. Cardiac ejection fraction<40% by echocardiogram or multigated acquisition (MUGA) scan.

11. Any infection requiring hospitalization or treatment with IV anti-infectives within 2 weeks of first administration of study drug.

12. Uncontrolled infection with human immunodeficiency virus (HIV), hepatitis B or hepatitis C infection; or other uncontrolled infection, except: (a) Patients with HIV who have controlled infection (undetectable viral load and CD4 count above 350 cells/microliter either spontaneously or on a stable antiviral regimen) are permitted; (b) Patients with hepatitis B (HepBsAg+) who have controlled infection (serum hepatitis B virus DNA polymerase chain reaction [PCR] that is below the limit of detection AND receiving anti-viral therapy for hepatitis B) are permitted; (c) Patients who are hepatitis C virus antibody positive (HCV Ab+) who have controlled infection (undetectable HCV RNA by PCR either spontaneously or in response to a successful prior course of anti-HCV therapy) are permitted.

13. History of severe allergic reaction attributed to compounds with a similar chemical or biologic composition as that of the study drug or excipient. A severe allergic reaction is defined for this purpose as that requiring hospitalization and/or treatment with epinephrine.

14. Known hypersensitivity to both allopurinol and rasburicase.

15. Member of the clinical site study team or his/her immediate family, unless prior approval granted by the sponsor.

16. Women with a positive serum β-hCG pregnancy test at the screening visit. If positive, pregnancy must be ruled out by ultrasound for patient to be eligible.

17. Patients who are committed to an institution by virtue of an order issued either by the judicial or the administrative authorities.

18. Pregnant or breastfeeding women.

19. Women of childbearing potential* or men who are unwilling to practice highly effective contraception prior to the initial dose/start of the first treatment, during the study, and for at least 6 months after the last dose. Highly effective contraceptive measures include: (a) stable use of combined (estrogen and progestogen containing) hormonal contraception (oral, intravaginal, transdermal) or progestogen-only hormonal contraception (oral, injectable, implantable) associated with inhibition of ovulation initiated 2 or more menstrual cycles prior to screening; (b) intrauterine device (IUD); intrauterine hormone-releasing system (IUS); (c) bilateral tubal ligation; (d) vasectomized partner; (e) and/or sexual abstinence †, ‡.

Postmenopausal women must be amenorrheic for at least 12 months in order not to be considered of childbearing potential. Pregnancy testing and contraception are not required for women with documented hysterectomy or tubal ligation.

† Sexual abstinence is considered a highly effective method only if defined as refraining from heterosexual intercourse during the entire period of risk associated with the study drugs. The reliability of sexual abstinence needs to be evaluated in relation to the duration of the clinical trial and the preferred and usual lifestyle of the subject.
‡ Periodic abstinence (calendar, symptothermal, post-ovulation methods), withdrawal (coitus interruptus), spermicides only, and lactational amenorrhoea method (LAM) are not acceptable methods of contraception. Female condom and male condom should not be used together.

Treatment:

REGN1979 will be administered by IV infusion at an initial dose of 1 mg during week 1, an intermediate dose of 20 mg during week 2, and a nominal dose of 80 mg or 160 mg during subsequent administrations. For the initial dose, intermediate dose and first nominal dose (primary, secondary and tertiary doses, respectively), the treatments will be split into 2 separate infusions, each over 4 hours on each of 2 days that are preferably consecutive but no more than 3 days apart (e.g., week 1 day 1 and week 1 day 2). Subsequent treatments (maximum weekly doses; e.g., 320 mg) may be administered as a single infusion or as 2 separate infusions and may be administered over 1 to 4 hours depending on tolerability. Study treatment comprises 12 QW administrations followed by Q2W dosing for 86 weeks, for a total of 98 weeks of study drug dosing.

Endpoints:

The primary endpoint of the study is ORR from first dose until 194 weeks following the first dose, as measured by the Lugano Classification of response in malignant lymphoma (Cheson, 2014) and according to independent central review, in patients with FL that has relapsed or is refractory to at least 2 prior lines of systemic therapy, including an anti-CD20 antibody and an alkylating agent. The secondary endpoints are: (1) ORR according to the Lugano Classification as assessed by local investigator evaluation from first dose up to 194 weeks following the first dose; (2) CR rate from first dose until 194 weeks following the first dose, according to the Lugano Classification, as assessed by independent central review, and local investigator evaluation; (3) PFS from first dose until 194 weeks following the first dose, according to the Lugano Classification, as assessed by independent central review, and local investigator evaluation; (4) OS from first dose up to until 194 weeks following the first dose; (5) DOR from first dose until 194 weeks following the first dose, according to the Lugano Classification, as assessed by independent central review, and local investigator evaluation; (6) DCR from first dose until 194 weeks following first dose, according to the Lugano Classification, as assessed by independent central review, and local investigator evaluation; (7) DDC from first dose until 194 weeks following the first dose, according to the Lugano Classification, as assessed by independent central review, and local investigator evaluation; (8) Incidence and severity of treatment-emergent adverse events (TEAEs) from first dose until 194 weeks following the first dose; and (9) Changes in scores of patient-reported outcomes from first dose until 194 weeks following the first dose as measured by the validated instruments EORTC QLQ-C30 and EQ-5D-3L.

Procedures and Assessments:

For all patients, disease will be assessed radiologically using computed tomography (CT) or magnetic resonance imaging (MRI) and by $^{18}$F-fluorodeoxyglucose-positron emission tomography (FDG-PET) imaging. Tumor response according to the Lugano Classification criteria will be adjudicated by independent central radiology review. Bone marrow aspirate, bone marrow biopsy, and lymph node and/or tumor biopsy will be performed, and samples will be evaluated histologically and may be used for other studies, including for immunohistochemistry. Safety will be evaluated by the assessment of vital signs, physical examination, Eastern Cooperative Oncology Group (ECOG) performance status, electrocardiogram (ECG), incidence of AEs, and reporting of concomitant medications. Laboratory evaluations include complete blood count with differential, blood chemistry values, serum immunoglobulins G (IgG), serum pregnancy testing (if relevant), ferritin, and C-reactive protein (CRP). Blood samples for PK and anti-drug antibody (ADA) assessment will be collected. Peripheral blood samples will be collected to assess changes in biomarkers (e.g., cytokine production, serum levels of pro-inflammatory cytokines, and changes in lymphocyte subsets and activation status). In addition, these samples will permit tumor or somatic genetic analyses for variations that impact the clinical course of underlying disease or modulate treatment side effects. Quality of life assessments will be performed using the self-administered EORTC QLQ-C30 and EQ-5D-3L questionnaires.

Statistical Plan:

This study is designed to evaluate the efficacy and safety of REGN1979 for patients with FL that has relapsed or is refractory to at least 2 prior lines of systemic therapies. The analysis for the primary efficacy endpoint will be performed after all the patients completed 28 weeks of study treatment period to assessments and have had an assessment of tumor responses or have withdrawn from the study. Justification of Sample Size—a single-stage exact binomial design is adopted for the primary endpoint of ORR. The 2-sided 95% confidence intervals for the observed ORRs were calculated based on the sample size 100. With 100 patients, if the observed ORR is at least 60%, 66%, 70%, and 75%, the lower limit of 95% CI will exclude the ORR of 49%, 55%, 60%, and 65% respectively; ie, the ORR is significantly different from 49%, 55%, 60%, and 65% as shown in Table 10, below.

TABLE 10

The 2-sided 95% Exact Confidence Intervals for Observed ORR Given a Sample Size of 100 Patients

| Number of Responders | Observed ORR | 95% CI-lower | 95% CI-upper |
| --- | --- | --- | --- |
| 60 | 0.60 | 0.497 | 0.697 |
| 66 | 0.66 | 0.558 | 0.752 |
| 70 | 0.70 | 0.6002 | 0.788 |
| 75 | 0.75 | 0.653 | 0.831 |

With the sample size of 100 patients, if the true treatment effect of REGN1979 is 64%, 70%, 75%, or 80%, the probability is 82%, 83%, 89%, or 91% for observed lower bound of 95% CI to exclude 49%, 55%, 60%, or 65% respectively. The sample size will be further increased by 10% to account for patients who withdraw prematurely from the study. Hence, the total sample size will be 112 patients.

Statistical Methods:

Demographic and baseline characteristics will be summarized descriptively. The primary efficacy endpoint is the ORR according to the Lugano Classification based on independent central review. The ORR along with the 2-sided 95% confidence interval will be summarized. Patients who are not evaluable for the best overall response will be considered as non-responders. The secondary efficacy endpoints of ORR as determined by investigator review according to Lugano Classification, and the CR rate and DCR by local investigator evaluation and by independent central review according to the Lugano Classification will be summarized along with 2-sided 95% confidence interval. The other secondary efficacy endpoints, including DOR, DDC, PFS, and OS will be summarized by median and its 95% confidence interval using the Kaplan-Meier method according to Lugano Classification. Disease control rate will be summarized along with 2-sided confidence interval. Quality of life measured by validated instruments EORTC QLQ-C30 and EQ-5D-3L will be summarized by descriptive statistics. Safety observations and measurements including drug exposure, AEs, laboratory data, vital signs, and ECOG performance status will be summarized and presented in tables and listings.

Interim Analysis:

An interim analysis will be performed after the first 50 patients have completed tumor assessments at 28 weeks or have withdrawn from the study earlier. The ORR and associated 95% confidence interval will be summarized. As the primary objective of this interim analysis is point estimation on ORR and characterizing the precision of point estimation, there is no hypothesis testing associated with this interim analysis. Therefore, Type I error adjustment is not applicable for this planned interim analysis. For other efficacy endpoints, 2-sided 95% confidence interval will also be presented.

Additional efficacy investigations of REGN1979 may be included in the present study, or in additional studies, including in (a) patients with follicular lymphoma (grade 1-3a) as third line or greater (3L+) therapy, (b) patients with follicular lymphoma (grade 1-3a) that are fit for full dose chemotherapy as second line or greater (2L+) therapy, (c) patients with follicular lymphoma (grade 1-3a) that are unfit for full dose chemotherapy as 2L+ therapy, (d) patients with follicular lymphoma (grade 1-3a) that are previously untreated and fit for full dose chemo-immunotherapy, (e) patients with follicular lymphoma (grade 1-3a) that are previously untreated and unfit for full dose chemo-immunotherapy, (f) patients with follicular lymphoma (grade 1-3a) fit for full dose chemo-immunotherapy as first line (1L) therapy versus standard of care, (g) patients with follicular lymphoma (grade 1-3a) unfit for full dose chemo-immunotherapy as 1L therapy versus standard of care, (h) patients with follicular lymphoma (grade 1-3a) fit for full dose chemo-immunotherapy as 2L+ therapy versus standard of care, (i) patients with follicular lymphoma (grade 1-3a) unfit for full dose chemo-immunotherapy as 2L+ therapy versus standard of care, and/or (j) patients with follicular lymphoma in combination with standard of care.

Additional efficacy investigations of REGN1979 may be included in the present study, or in additional studies, including in (a) patients with diffuse large B-cell lymphoma (DLBCL) that is de novo or transformed as 3L+ therapy, (b) patients with DLBCL following failure of CAR-T therapy, (c) patients with DLBCL eligible for autologous HSCT (hematopoietic stem cell transplantation) as 2L+ therapy, (d) patients with DLBCL ineligible for HSCT as 2L+ therapy, (e) patients with DLBCL that are previously untreated, with poor molecular prognostic factors (non-germinal center B, double hit or triple hit) and fit for full dose chemo-immunotherapy, (f) patients with DLBCL that are previously untreated, poor molecular prognostic factors (non-germinal center B, double hit or triple hit) and unfit for full dose chemo-immunotherapy, (g) patients with DLBCL that are CAR-T naïve, (h) patients with DLBCL at a maximum weekly dose of 320 mg, (i) patients with DLBCL in combination with standard of care, (j) patients with DLBCL for full dose chemo-immunotherapy as 1L therapy versus standard of care, (k) patients with DLBCL unfit for full dose chemo-immunotherapy as 1L therapy versus standard of care, (l) patients with DLBCL that are eligible for auto-HSCT as 2L+ therapy versus standard of care, and/or (m) patients with DLBCL that are ineligible for auto-HSCT as 2L+ therapy versus standard of care.

Additional efficacy investigations of REGN1979 may be included in the present study, or in additional studies, including in (a) patients with mantle cell lymphoma (MCL) following BTK inhibitor failure as 2L+ therapy, (b) in patients with marginal zone lymphoma (MZL) as 2L+ therapy, and/or (c) in patients with lymphoblastic lymphoma, lymphoplasmacytic lymphoma, Burkitt lymphoma, or other B-NHL subtypes as 2L+ therapy.

Additional efficacy investigations of REGN1979 may be included in the present study, or in additional studies, including in (a) patients with a CD20+ B-cell malignancy that have received a single dose of rituximab one day prior to the first dose of REGN1979. In this rituximab lead-in cohort and expansion only, a single dose of rituximab (375 mg/m²) will be administered one day prior to the first dose of REGN1979 [i.e, on study day (−1)]. REGN1979 will be started on Week 1 Day 1, and the treatment period for REGN1979 will be 9 months. Patients will be treated with up to 24 doses of REGN1979: 4 weekly doses during a 4-week induction period, followed by an additional 8 weekly doses, and 12 doses administered Q2W during a 6-month maintenance period. In the first part of this rituximab lead-in cohort, REGN1979 will be administered using a step-up dose of 80 mg. Once an optimal dose regimen is identified, one additional dose group of 6 patients at a step-up dose of 320 mg REGN1979 will be evaluated with the optimal dose regimen. Dose groups with step-up doses of REGN1979 between 80 mg and 320 mg may be evaluated also. Subsequently, an additional 24 patients will be evaluated with this optimal dose regimen and optimal dose, and together with the 6 patients in the rituximab lead-in group treated at the optimal dose a total of 30 patients will be reviewed for safety and tolerability.

In any of the combination studies with standard of care, the combination may include REGN1979 plus CHOP (cyclophosphamide, doxorubicin, vincristine and prednisone), ICE (ifosfamide, carboplatin and etoposide), Gem-Ox (gemcitabine and oxaliplatin), lenalidomide, or lenalidomide plus rituximab.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A method of administering a therapeutic protein to a subject in a dosing regimen to mitigate adverse effects of cytokine release syndrome (CRS) or infusion-related reaction (IRR) in the treatment of a CD20-expressing B-cell malignancy, comprising:

administering fractions of a primary dose (D1) of the therapeutic protein in week 1 of the dosing regimen, wherein the primary dose comprises no more than 10 mg of the therapeutic protein, a first dose fraction (F1D1) comprises 40% to 60% of the total primary dose and is administered to the subject on day 1 of week 1, and a second dose fraction (F2D1) comprises the remaining 40% to 60% of the total primary dose and is administered to the subject from 12 to 96 hours following administration of the F1D1;

administering fractions of a secondary dose (D2) of the therapeutic protein in week 2 of the dosing regimen, wherein the secondary dose is greater than the primary dose and no more than one-half of a maximum weekly dose of the therapeutic protein, a first dose fraction (F1D2) comprises 40 to 60% of the total secondary dose, a second dose fraction (F2D2) comprises the remaining 40% to 60% of the total secondary dose, and the F2D2 is administered to the subject from 12 to 96 hours following administration of the F1D2 during week 2 of the dosing regimen; and administering the maximum weekly dose of the therapeutic protein to the subject as a single dose in a subsequent week of the dosing regimen, wherein the administration of the therapeutic protein to the subject in the dosing regimen reduces the prevalence or severity, or both the prevalence and severity, of CRR or IRR compared to a dosing regimen not including split administration of the primary dose and the secondary dose, and wherein the therapeutic protein is a bispecific antibody or antigen-binding fragment thereof comprising a first antigen-binding arm that binds human CD3 and comprises complementarity determining regions HCDR1-HCDR2-HCDR3-LCDR1-LCDR2-LCDR3 comprising the amino acid sequences, respectively, of SEQ ID NOs: 19-20-21-22-23-24, and a second antigen-binding arm that binds human CD20 and comprises complementarity determining regions HCDR1-HCDR2-HCDR3-LCDR1-LCDR2-LCDR3 comprising the amino acid sequences, respectively, of SEQ ID NOs: 16-17-18-22-23-24.

2. The method of claim 1, wherein the F2D1 is administered to the subject from 24 to 96 hours following administration of the F1D1.

3. The method of claim 1, wherein the F2D2 is administered to the subject from 24 to 96 hours following administration of the F1D2.

4. The method of claim 1, wherein the subsequent week is week 3 of the dosing regimen, the subsequent week is week 4 of the dosing regimen, or the subsequent week is week 14 of the dosing regimen.

5. The method of claim 1, further comprising:

administering fractions of a tertiary dose (D3) of the therapeutic protein in week 3 of the dosing regimen, wherein the tertiary dose is no less than one-half of the maximum weekly dose of the therapeutic protein and no more than the maximum weekly dose of the therapeutic protein, a first dose fraction (F1D3) comprises 40% to 60% of the total tertiary dose, a second dose fraction (F2D3) comprises the remaining 40% to 60% of the total tertiary dose, and the F2D3 is administered to the subject from 12 to 96 hours following administration of the F1D3 during week 3 of the dosing regimen; and administering the maximum weekly dose of the therapeutic protein to the subject as a single dose in a subsequent week of the dosing regimen.

6. The method of claim 5, wherein the F2D3 is administered to the subject from 24 to 96 hours following administration of the F1D3.

7. The method of claim 5, wherein the subsequent week is week 4 of the dosing regimen, or the subsequent week is any one of weeks 4 to 36 of the dosing regimen.

8. The method of claim 5, wherein the tertiary dose is 40 mg, 80 mg, 160 mg, or 320 mg.

9. The method of claim 5, wherein the F1D3 comprises 50% of the total tertiary dose, and the F2D3 comprises 50% of the total tertiary dose.

10. The method of claim 5, wherein the F2D3 is administered to the subject from 18 to 72 hours following administration of the F1D3.

11. The method of claim 5, wherein the tertiary dose is administered as a single dose in weeks 4 to 12 of the dosing regimen.

12. The method of claim 5, wherein the therapeutic protein is administered to the subject in combination with a second agent selected from a steroid, an anti-histamine, acetaminophen, a non-steroidal anti-inflammatory drug (NSAID), an IL-6 antagonist, or an IL-6R antagonist.

13. The method of claim 12, wherein the steroid is dexamethasone, or the NSAID is indomethacin.

14. The method of claim 13, wherein the dexamethasone is administered to the subject about one to three hours prior to at least one of the F1D3 and the F2D3.

15. The method of claim 1, wherein the maximum weekly dose of the therapeutic protein is administered to the subject as a single dose during a weekly phase of the dosing regimen.

16. The method of claim 1, further comprising administering the maximum weekly dose of the therapeutic protein to the subject as a single dose once every two weeks, one every three weeks, or one every four weeks during a maintenance phase of the dosing regimen, which follows completion of a weekly phase of the dosing regimen, wherein the maximum weekly dose is from 80 mg to 320 mg.

17. The method of claim 1, wherein the primary dose (D1) is 1 mg.

18. The method of claim 1, wherein the secondary dose (D2) is 20 mg.

19. The method of claim 1, wherein the F1D1 comprises 50% of the total primary dose, and the F2D1 comprises 50% of the total primary dose.

20. The method of claim 1, wherein the F1D2 comprises 50% of the total secondary dose, and the F2D2 comprises 50% of the total secondary dose.

21. The method of claim 1, wherein the maximum weekly dose of the therapeutic protein is from 5 mg to 320 mg.

22. The method of claim 1, wherein the maximum weekly dose is 80 mg, 160 mg, or 320 mg.

23. The method of claim 1, wherein the CD20-expressing B-cell malignancy is non-Hodgkin lymphoma, Hodgkin lymphoma, chronic lymphocytic leukemia, acute lymphoblastic leukemia, small lymphocytic lymphoma, diffuse large B-cell lymphoma, follicular lymphoma, mantle cell lymphoma, marginal zone lymphoma, Burkitt lymphoma, primary mediastinal B-cell lymphoma, lymphoblastic lymphoma, or Waldenstrom macroglobulinemia.

24. The method of claim 1, wherein the subject has been diagnosed with follicular lymphoma (FL).

25. The method of claim 24, wherein the FL is grade 1-3a.

26. The method of claim 1, wherein the subject has been diagnosed with diffuse large B-cell lymphoma (DLBCL).

27. The method of claim 26, wherein the subject has failed prior CAR-T therapy.

28. The method of claim 1, wherein the subject has been diagnosed with mantle cell lymphoma (MCL).

29. The method of claim 28, wherein the subject has failed prior Bruton tyrosine kinase (BTK) inhibitor therapy.

30. The method of claim 1, wherein the subject has been diagnosed with marginal zone lymphoma (MZL).

31. The method of claim 1, wherein the therapeutic protein is maintained at a serum concentration at or above about 2000 mcg/L, at or above about 2600 mcg/L, or at least about 3700 mcg/L following administration of the maximum weekly dose for the duration of the dosing regimen.

32. The method of claim 1, wherein the therapeutic protein is administered to the subject in combination with a second agent selected from a steroid, an anti-histamine, acetaminophen, a non-steroidal anti-inflammatory drug (NSAID), an IL-6 antagonist, or an IL-6R antagonist.

33. The method of claim 32, wherein the steroid is dexamethasone, or the NSAID is indomethacin.

34. The method of claim 33, wherein the dexamethasone is administered to the subject about one to three hours prior to at least one of the F1 D1, the F2D1, the F1D2, and the F2D2.

35. The method of claim 32, wherein the IL-6 antagonist is an anti-IL-6 antibody, or the IL-6R antagonist is an anti-IL-6R antibody, or the anti-IL-6R antagonist is sarilumab.

36. The method of claim 32, wherein administration of the second agent is eliminated following a first administration of the maximum weekly dose for the duration of the dosing regimen.

37. The method of claim 1, wherein the therapeutic protein is administered to the subject in combination with a second therapeutic agent, wherein the second therapeutic agent comprises at least one of rituximab, obinutuzumab, cyclophophamide, doxorubicin, vincristine, prednisone, prednisolone, bendamustine, lenalidomide, chlorambucil, ibritumomab tiuxetan, idelalisib, copanlisib, duvelisib, etoposide, methylprednisolone, cytarabine, cisplatin, mesna, ifosfamide, mitoxantrone, and procarbazine.

38. The method of claim 1, wherein the subject has been treated previously with an anti-cancer therapy.

39. The method of claim 38, wherein the subject is refractory to previous treatment or has relapsed after previous treatment.

40. The method of claim 38, wherein the subject has previously been treated with an anti-CD20 antibody therapy.

41. The method of claim 40, wherein the anti-CD20 antibody therapy comprises rituximab.

42. The method of claim 1, wherein the incidence of grade 3 CRS and IRR is less than 10%.

43. The method of claim 42, wherein the incidence of grade 3 CRS and IRR is less than 7.5% or less than 7%.

44. The method of claim 1, wherein the first antigen-binding arm that binds human CD3 comprises a heavy chain variable region (HCVR) comprising the amino acid sequence of SEQ ID NO: 14 and a light chain variable region (LCVR) comprising the amino acid sequence of SEQ ID NO: 15.

45. The method of claim 1, wherein the second antigen-binding arm that binds human CD20 comprises a heavy chain variable region (HCVR) comprising the amino acid sequence of SEQ ID NO: 13 and a light chain variable region (LCVR) comprising the amino acid sequence of SEQ ID NO: 15.

46. The method of claim 1, wherein the first antigen-binding arm that binds human CD3 comprises a heavy chain variable region (HCVR) comprising the amino acid sequence of SEQ ID NO: 14 and a light chain variable region (LCVR) comprising the amino acid sequence of SEQ ID NO: 15, and the second antigen-binding arm that binds human CD20 comprises a heavy chain variable region (HCVR) comprising the amino acid sequence of SEQ ID NO: 13 and a light chain variable region (LCVR) comprising the amino acid sequence of SEQ ID NO: 15.

47. The method of claim 1, wherein the therapeutic protein is a bispecific anti-CD3×anti-CD20 antibody.

48. The method of claim 47, wherein the bispecific anti-CD3×anti-CD20 antibody comprises a first heavy chain comprising the amino acid sequence of SEQ ID NO: 11 or an amino acid sequence comprising residues 1-448 of SEQ ID NO: 11, and a light chain comprising the amino acid sequence of SEQ ID NO: 12.

49. The method of claim 47, wherein the bispecific anti-CD3×anti-CD20 antibody comprises a second heavy chain comprising the amino acid sequence of SEQ ID NO: 10 or an amino acid sequence comprising residues 1-452 of SEQ ID NO: 10, and a light chain comprising the amino acid sequence of SEQ ID NO: 12.

50. The method of claim 47, wherein the bispecific anti-CD3×anti-CD20 antibody comprises a first heavy chain comprising the amino acid sequence of SEQ ID NO: 11 or an amino acid sequence comprising residues 1-448 of SEQ ID NO: 11, a second heavy chain comprising the amino acid sequence of SEQ ID NO: 10 or an amino acid sequence comprising residues 1-452 of SEQ ID NO: 10, and a common light chain comprising the amino acid sequence of SEQ ID NO: 12.

51. The method of claim 1, wherein the F2D1 is administered to the subject from 18 to 72 hours following administration of the F1D1.

52. The method of claim 1, wherein the F2D2 is administered to the subject from 18 to 72 hours following administration of the F1D2.

53. The method of claim 1, wherein the subsequent week is any one of weeks 4 to 36 of the dosing regimen.

* * * * *